United States Patent [19]
Cama et al.

[11] Patent Number: 6,140,318
[45] Date of Patent: *Oct. 31, 2000

[54] CARBAPENEM ANTIBACTERIAL COMPOUNDS, COMPOSITIONS CONTAINING SUCH COMPOUNDS AND METHODS OF TREATMENT

[75] Inventors: Lovji D. Cama, Tenafly; Robert R. Wilkening, Maplewood; Ronald W. Ratcliffe, Matawan; Kenneth J. Wildonger, Bridgewater; Wanying Sun, Edison, all of N.J.

[73] Assignee: Merck & Co., Inc., Rahway, N.J.

[*] Notice: This patent is subject to a terminal disclaimer.

[21] Appl. No.: 09/168,622

[22] Filed: Oct. 8, 1998

Related U.S. Application Data

[60] Provisional application No. 60/063,240, Oct. 23, 1997, and provisional application No. 60/067,935, Dec. 8, 1997.

[51] Int. Cl.[7] ............... A61K 31/395; A01N 43/60; C07D 487/00; C07D 413/00
[52] U.S. Cl. ............... 514/210.09; 514/254.02; 540/302; 544/368
[58] Field of Search ............ 540/302; 514/210.09, 514/254.02; 544/368

[56] References Cited

U.S. PATENT DOCUMENTS

| | | | |
|---|---|---|---|
| 4,309,438 | 1/1982 | Christensen et al. | 424/274 |
| 4,479,947 | 10/1984 | Christensen | 424/203 |
| 5,756,725 | 5/1998 | Wilkening et al. | 540/302 |

FOREIGN PATENT DOCUMENTS

WO 97/40048  10/1997  WIPO .

OTHER PUBLICATIONS

S. M. Schmitt et al. *J. Antibiotics*, 41(6), pp 780–787 (1988).

T. W. Green, *Protective Group Inorganic Synethesis*, Wiley, NY (1991).

*Primary Examiner*—Mukund J. Shah
*Assistant Examiner*—Tamthom N. Truong
*Attorney, Agent, or Firm*—James M. Hunter, Jr.; Sylvia A. Ayler; Mark R. Daniel

[57] ABSTRACT

Compounds of formula I are disclosed.

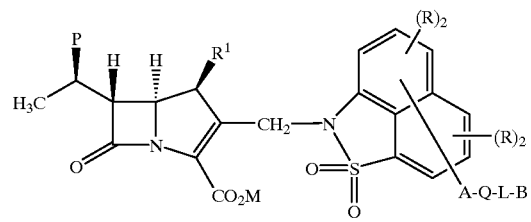

as well as pharmaceutically acceptable salts thereof.

The naphthosultam is substituted with various substituent groups including at least one cationic group -A-Q-L-B.

The carbapenems of the invention are effective against susceptible bacterial organisms, including methicillin resistant *Staphylococcus aureus* (MRSA), methicillin resistant *Staphylococcus epidermidis* (MRSE), and methicillin resistant coagulase negative Staphylococci (MRCNS).

10 Claims, No Drawings

CARBAPENEM ANTIBACTERIAL COMPOUNDS, COMPOSITIONS CONTAINING SUCH COMPOUNDS AND METHODS OF TREATMENT

RELATED APPLICATION

This application claims the benefit of U.S. Provisional Application No. 60/063,240, filed Oct. 23, 1997 and U.S. Provisional Application No. 60/067,935, filed Dec. 8, 1997.

BACKGROUND OF THE INVENTION

The present invention relates to carbapenem antibacterial agents in which the carbapenem nucleus is substituted at the 2-position with a naphthosultam linked through a $CH_2$ group. The naphthosultam is further substituted with various substituent groups including at least one cationic group -A-Q-L-B.

The carbapenems of the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS), and are also active against Gram negative bacteria. There is an increasing need for agents effective against such pathogens (MRSA/MRCNS) which are at the same time relatively free from undesirable side effects. The antibacterial compounds of the present invention thus comprise an important contribution to therapy for treating infections caused by these difficult to control pathogens.

SUMMARY OF THE INVENTION

The compounds of the invention are represented by formula I:

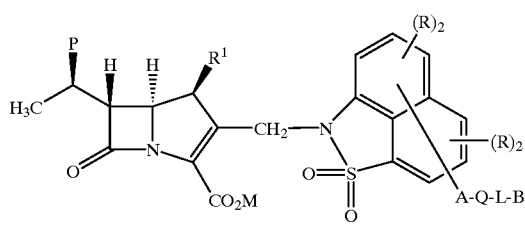

as well as pharmaceutically acceptable salts thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

A-Q-L-B represents a side chain wherein:

A is a $C_{1-6}$ alkylene group, straight or branched, and optionally interrupted or terminated by 1–2 of —O—, —S—, $NR^a$—, —C(O)— and —CH=CH—;

Q is selected from:

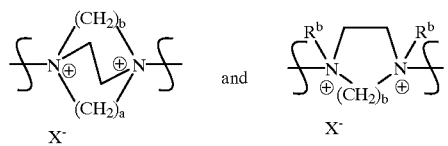

in which:

a is 1, 2 or 3;

b is 2 or 3;

and X— is a monovalent or divalent charge balancing counterion;

L represents a bond or a $C_{1-8}$ alkylene group, unsubstituted or substituted with 1–3 $R^c$ groups, uninterrupted, interrupted or terminated by 1–3 of —CH=CH—, —C(O)—, —C(O)$NR^d$—, —Het($R^e$)—, —C(O)—Het($R^e$)—, —C(O)$NR^a$—Het($R^e$)—, —O—, —S—, —S(O)—, —$SO_2$—, —$CO_2$—, —$NR^a$—, —$N^+(R^1)_2$—,

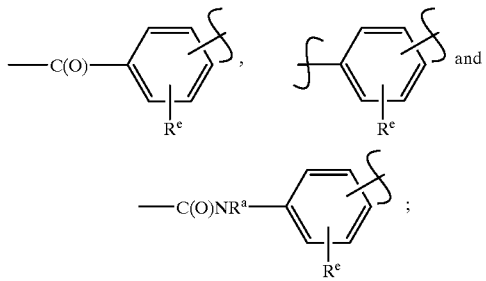

Het is a heteroaryl group;

B represents a member selected from the group consisting of:

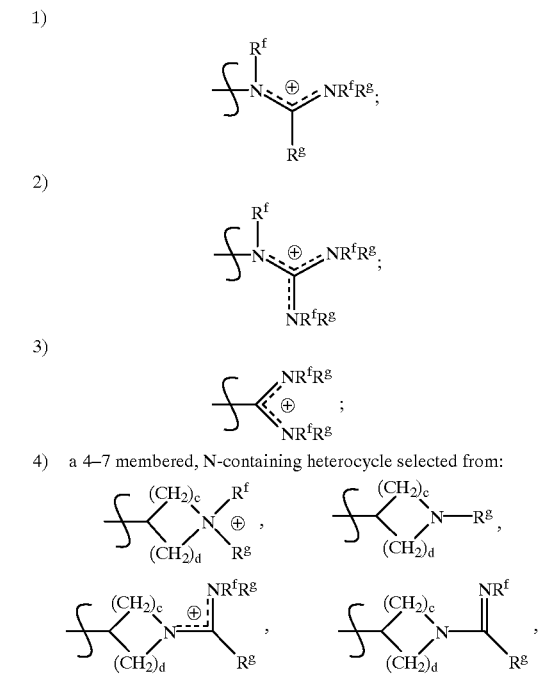

-continued

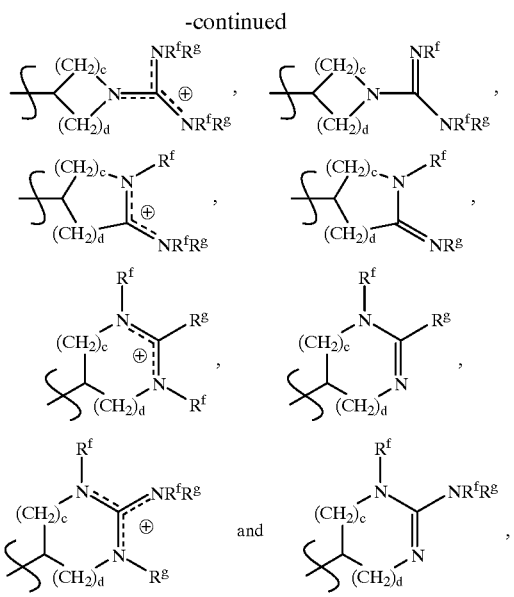

wherein c and d are independently 0–4, such that c+d equals from 2–5, and said heterocycle is optionally substituted on carbon atoms with 1–2 $R^f$ or $R^g$ groups, and is optionally interrupted by O, S, $NR^f$ or $NR^g$;

5)

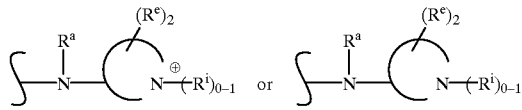

wherein

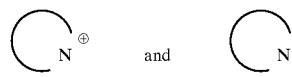

represent quaternary and non-quaternary 5–10 membered mono- or bicyclic, N-containing heteroaryl groups, respectively, optionally containing 1–4 additional heteroatoms selected from O, S and N; and

6)

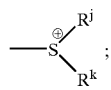

$R^a$ is H or $C_{1-6}$ alkyl;
$R^b$ is independently selected from $NH_2$ and $C_{1-6}$ alkyl unsubstituted or substituted with 1–3 groups selected from halo, OH, CN and $C(O)NH_2$;
$R^c$ is independently selected from halo, $OR^a$, $SR^a$, $OC(O)R^a$, $CO_2R^a$, CN, $C(O)N(R^a)_2$ and $C(O)R^a$,
$R^d$ is H or $C_{1-3}$ alkyl, or $R^c$ and $R^d$ taken together with any intervening atoms represent a 4–6 membered ring;
$R^e$ is H; $R^c$; $NO_2$, $N(R^a)_2$, $SO_2N(R^a)_2$ or $C_{1-4}$ alkyl, unsubstituted or substituted with 1–3 groups selected from halo, OH and $C(O)NH_2$
$R^f$, $R^g$ and $R^h$ are independently selected from H; $C_{1-6}$ straight or branched chain alkyl, unsubstituted or substituted with 1–3 $R^c$ groups; $C_{3-6}$ cycloalkyl, unsubstituted or substituted with 1–3 $R^c$ groups; phenyl, unsubstituted or substituted with 1–3 $R^e$ groups and Het, unsubstituted or substituted with 1–3 $R^e$ groups,
or
$R^f$ and $R^g$ taken together with the intervening N atom form a 4–6 membered ring, optionally interrupted by 1–2 of O, S, C(O) or $NR^h$, and optionally substituted by 1–3 $R^c$ groups;
$R^i$ is H or $R^b$;
$R^j$ and $R^k$ are $C_{1-4}$ alkyl or $R^j$ and $R^k$ taken together with the intervening S atom are a 5–6 membered ring;
and each R independently represents H; $R^c$; $NO_2$; $N(R^a)_2$; $SO_2N(R^a)_2$ or $C_{1-4}$ alkyl, unsubstituted or substituted with 1–3 groups selected from halo, OH and $C(O)NH_2$,
or
R together with A of the group -A-Q-L-B and any intervening atoms represent a 5–6 membered carbocyclic ring.

Pharmaceutical compositions and methods of treatment are also included.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 15 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^c$, $R^f$ and $R^g$, or as otherwise defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" (Het) refers to a monocyclic aromatic hydrocarbon group having 5 or 6 ring atoms, or a bicyclic aromatic group having 8 to 10 atoms, containing at least one heteroatom, O, S or N, and in which 1–2 additional carbon atoms are optionally replaced by a heteroatom selected from O or S, and in which from 1–3 additional carbon atoms are optionally replaced by N, said heteroaryl group being optionally substituted as described herein. Examples include the following:

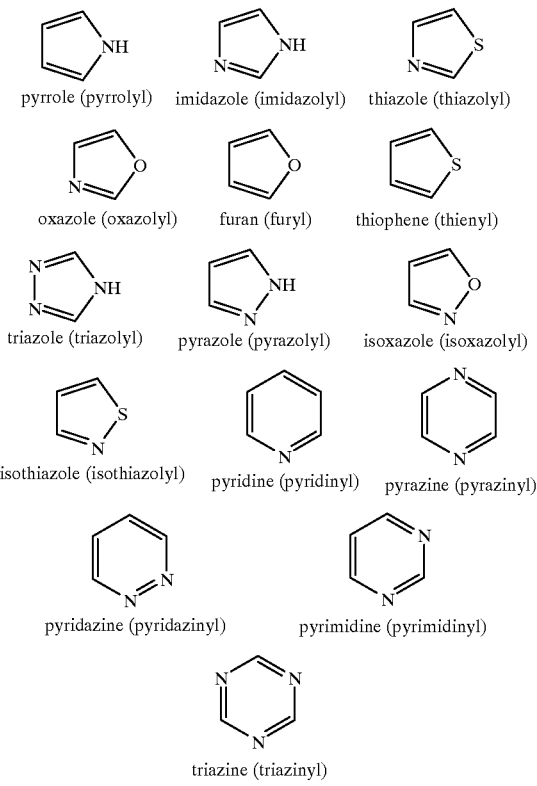

Heteroarylium refers to heteroaryl groups bearing a quaternary or protonated atom and thus a positive charge. Examples include the following:

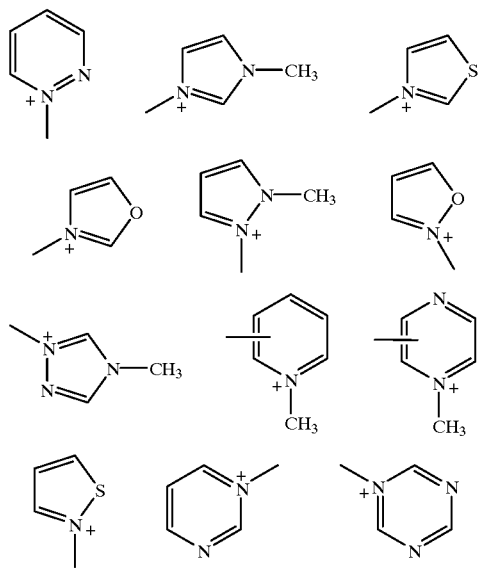

-continued

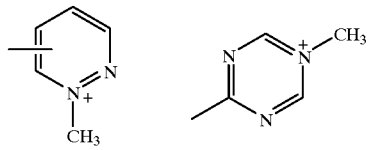

When a charge is shown on a particular nitrogen atom in a ring or in a nitrogen containing non-ring moiety which contains one or more additional nitrogen atoms, it is understood that the charge may reside on a different nitrogen atom than that shown in a particular drawing by virtue of charge resonance that occurs.

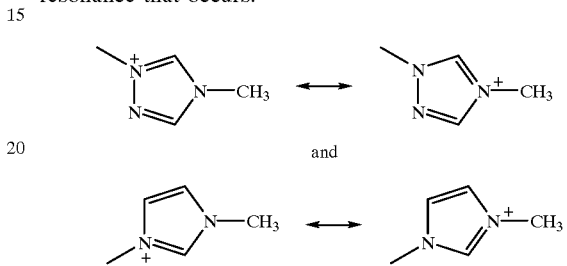

For example,

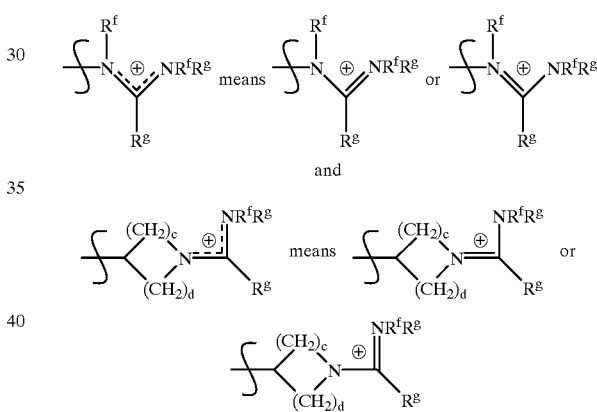

Likewise, when a basic nitrogen containing moiety is provided at an appropriately acidic pH, the moiety becomes protonated due to acid base reactivity. Both the protonated and non-protonated forms of the compounds of formula I are included in the present invention.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "substituted", unless otherwise indicated, this means that the group contains from 1 to 4 substituents thereon.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the carbapenem compounds of the present invention, M is a readily removable carboxyl protecting group, and/or P represents a hydroxyl which is protected by a hydroxyl-protecting group. Such conventional protecting groups consist of groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable hydroxyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form—COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Acid addition salts of the compounds of formula I are likely protonated at physiological pH, as mentioned above. Compounds such as those containing a basic N-containing moiety are capable of protonation in water at or near pH 7, so that the moiety can exist in its neutral form or as an acid addition (protonated) form.

X— is a charge balancing group.

For the purposes of this invention, all compounds which have one or more cations are balanced with one or more, as necessary, of a charge balancing group $X^-$. Examples of cases where a charge balancing group is required are quarternized substituents such as heteroarylium. Additionally, all compounds having one or more anions are counter balanced with one or more, as necessary, charge balancing counterions.

When a group is interrupted by 2–3 of O, S, or N they cannot form O—O, O—O—O, O—S, O—S—O, S—S, or S—S—S bonds. This is exemplified in the case when A is an alkylene interrupted or terminated by 1–2 of O, S, $NR^a$, . . . and the like.

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

X⁻ can be present or absent as necessary to maintain the appropriate charge balance. When present, these represent pharmaceutically acceptable counterions. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when more than one negative charge is necessary to maintain charge neutrality, the counterion indicator X— represents a specie with more than one negative charge, such as malonate, tartrate or ethylenediaminetetraacetate (EDTA), or when a multivalent negatively charged counterion is present with a carbapenem which bears a net single positive charge, an appropriate number of carbapenem molecules can be found in association therewith to maintain the overall charge balance and neutrality.

Numbering and nomenclature using in naming the naphthosultams are as follows:

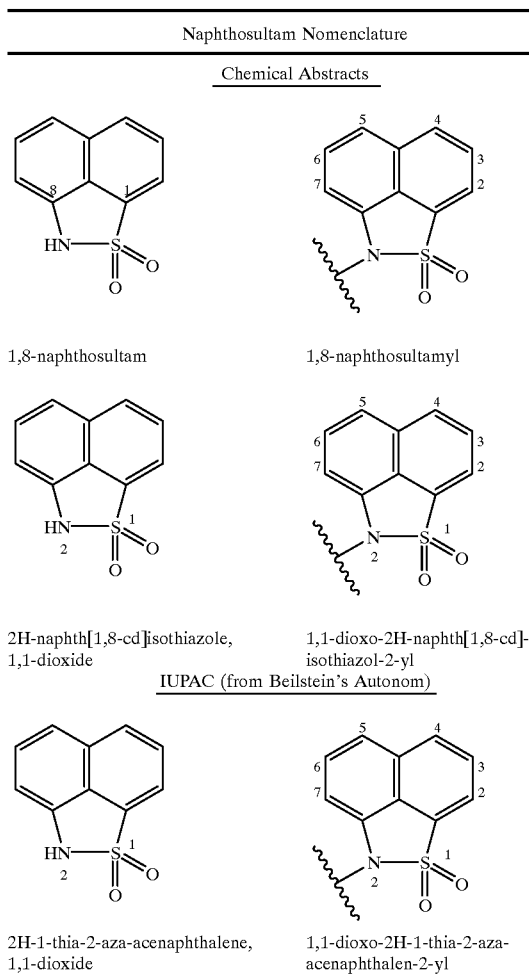

| Naphthosultam Nomenclature | |
|---|---|
| Chemical Abstracts | |
| 1,8-naphthosultam | 1,8-naphthosultamyl |
| 2H-naphth[1,8-cd]isothiazole, 1,1-dioxide | 1,1-dioxo-2H-naphth[1,8-cd]-isothiazol-2-yl |
| IUPAC (from Beilstein's Autonom) | |
| 2H-1-thia-2-aza-acenaphthalene, 1,1-dioxide | 1,1-dioxo-2H-1-thia-2-aza-acenaphthalen-2-yl |

The —A— portion of the side chain is a $C_{1-6}$ alkylene group which is straight or branched, and is optionally interrupted or terminated by 1–2 of O, S, $NR^a$, C(O), and —CH=CH—. The interrupting groups can be separate or together, and can terminate the $C_{1-6}$ alkylene group. Also, the interrupting or terminating moiety can be between the alkylene group and the naphthosultam or —Q—. For example, A can represent —O—$C_{1-6}$ alkyl—, —$C_{1-6}$ alkyl-O—, —NRa—$_{1-6}$ alkyl— and the like.

The variable L represents a bond or a $C_{1-8}$ alkylene group, which is unsubstituted or substituted with 1–3 $R^c$ groups. The $C_{1-8}$ alkylene moiety can be interrupted or terminated by 1–3 of the following:
—CH=CH—, —C(O)—, —C(O)$NR^d$—, —Het($R^e$)—, —C(O)—Het($R^e$)—, —C(O)$NR^a$—Het($R^e$)—, —O—, —S—, —S(O)—, —$SO_2$—, —$CO_2$—,

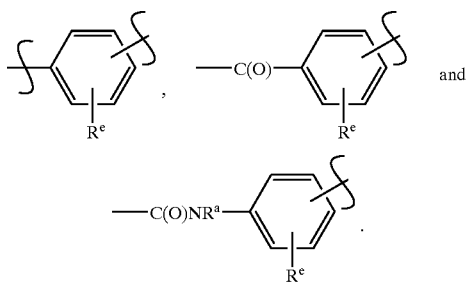

These interrupting or terminating moieties can be separate or together. As described above with respect to A, the moieties can be at the ends of the $C_{1-8}$ alkylene group, and between the $C_{1-8}$ alkylene moiety and Q or B.

B can be selected from groups 1)–6) shown above. These include positively charged as well as neutral moieties, many of which become positively charged at neutral to acidic pH. All are included in the present invention.

When $R^b$ represents $C_{1-6}$ alkyl, it may be unsubstituted or substituted with 1–3 groups selected from halo, OH, CN and C(O)NH$_{22}$.

When $R^c$ and $R^d$ both appear, they may be taken in combination with any intervening atoms to form a 4–6 membered ring.

When $R^f$ and $R^g$ are both present, they can be taken together with the intervening atoms to form a 4–6 membered ring, which is optionally interrupted by 1–2 of O, S, C(O) and $NR^h$. The ring can be unsubstituted or substituted with 1–3 $R^c$ groups.

When $R^j$ and $R^k$ are taken together with the S atom, they represent a 5–6 membered ring.

When one of the R groups is taken in combination with A from the side chain A-Q-L-B, along with the intervening atoms, it represents a 5–6 membered carbocyclic ring.

A subset of compounds of formula I which is of interest relates to those compounds where $R^1$ represents methyl. Within this subset, all other variables are as originally defined.

Another subset of compounds of formula I which is of interest relates to those compounds where $CO_2M$ represents a carboxylate anion. Hence, M in this instance represents a negative charge which is balanced by a positively charged group, such as in the positively charged Q group. Likewise, if the positively charged Q group contains more than one positive charge, a negatively charged counterion may be present which in combination with the carboxylate anion, provides overall charge neutrality.

Another subset of compounds of formula I that is of interest relates to those compounds where P represents hydroxyl or hydroxyl protected by a hydroxyl protecting group. Within this subset, all other variables are as originally defined.

Another subset of compounds of formula I that is of interest relates to compounds of formula I wherein A represents $C_{1-3}$ alkylene. Within this subset, all other variables are as originally defined.

Another subset of compounds of formula I that is of interest relates to compounds where Q represents

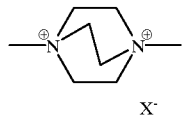

wherein X— represents a charge balancing group. Within this subset, all other variables are as originally defined.

Another subset of compounds of formula I that is of interest relates to compounds where L is a bond or $C_{1-5}$ alkylene, optionally interrupted or terminated by —C(O)NR$^d$—, —C(O)NR$^a$—Het(R$^e$)—, —NR$^a$—, —N$^+$(R$^a$)$_2$ or

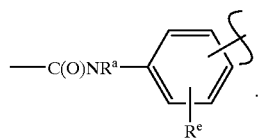

Within this subset, all other variables are as originally defined.

Another subset of compounds of formula I that is of interest relates to compounds where B is selected from:

1)

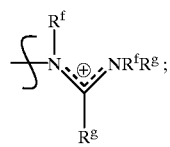

2)

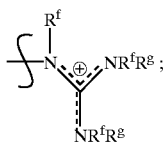

3)

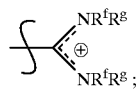

4) a 4–7 membered, N-containing heterocycle selected from:

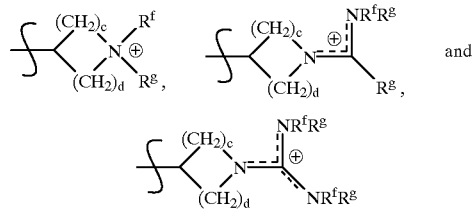

wherein c and d are independently 0–4, such that c+d equals from 2–4, and said heterocycle is optionally substituted on carbon atoms with 1–2 R$^f$ or R$^g$ groups, and is optionally interrupted by NR$^f$ or NR$^g$;

and

5)

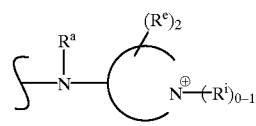

wherein

represents a quaternary 5–10 membered mono- or bicyclic, N-containing heteroaryl group, optionally containing 1–4 additional heteroatoms selected from O, S and N. Within this subset, all other variables are as originally defined.

A preferred subset of compounds of formula I which is of interest relates to those compounds wherein:

R$^1$ represents methyl;

CO$_2$M represents a carboxylate anion;

P represents hydroxyl or hydroxyl protected by a hydroxyl protecting group;

A represents $C_{1-3}$ alkylene;

Q represents

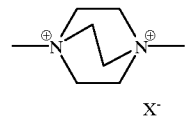

wherein X— represents a charge balancing;

L represents a bond or $C_{1-5}$ alkylene, optionally interrupted or terminated by —C(O)NR$^d$—, —C(O)NR$^a$—Het(R$^e$)—, —NR$^a$—, —N+(R$^a$)$_2$ or

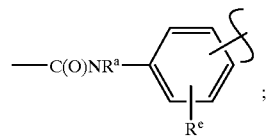

B is selected from:

1)

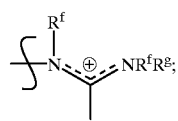

2)

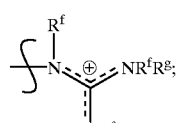

3) 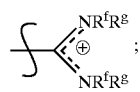

4) a 4–7 membered, N-containing heterocycle selected from:

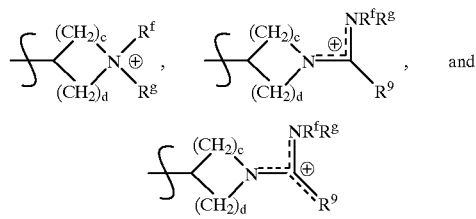

wherein c and d are independently 0–4, such that c+d equals from 2–4, and said heterocycle is optionally substituted on carbon atoms with 1–2 $R^f$ or $R^g$ groups, and is optionally interrupted by $NR^f$ or $NR^g$;

and

5)

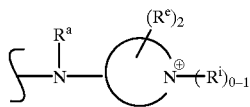

wherein

represents a quaternary 5–10 membered mono- or bicyclic, N-containing heteroaryl group, optionally containing 1–4 additional heteroatoms selected from O, S and N, and all other variables are as originally defined.

Representative examples of compounds of the invention are found in Tables I–III.

TABLE I

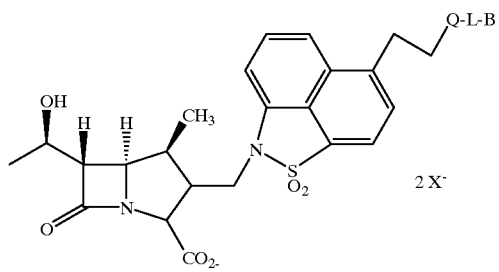

Q-L-B =

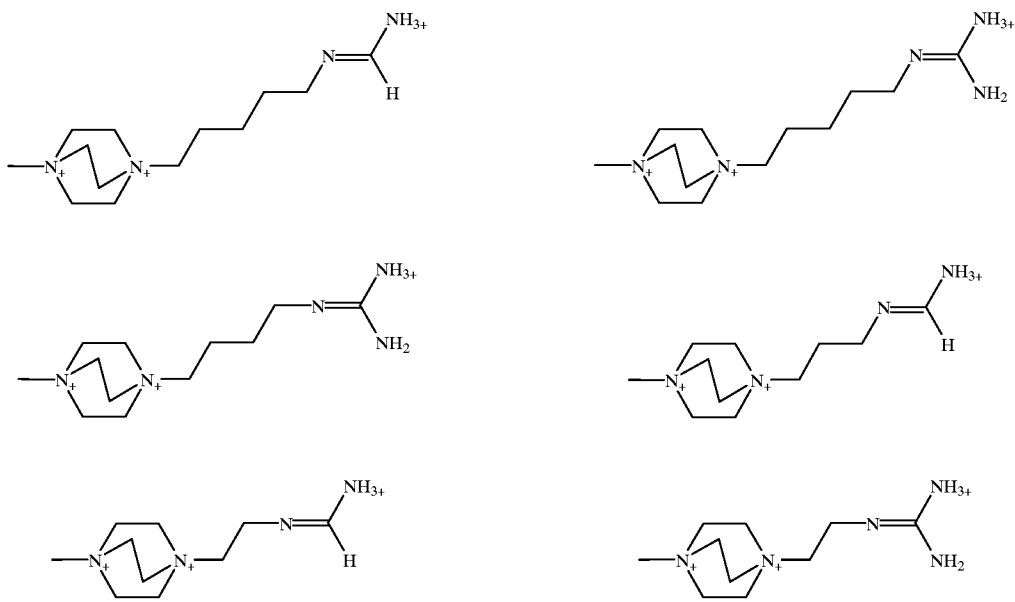

TABLE I-continued
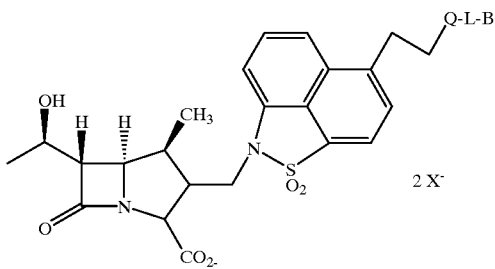
2 X⁻
Q-L-B =
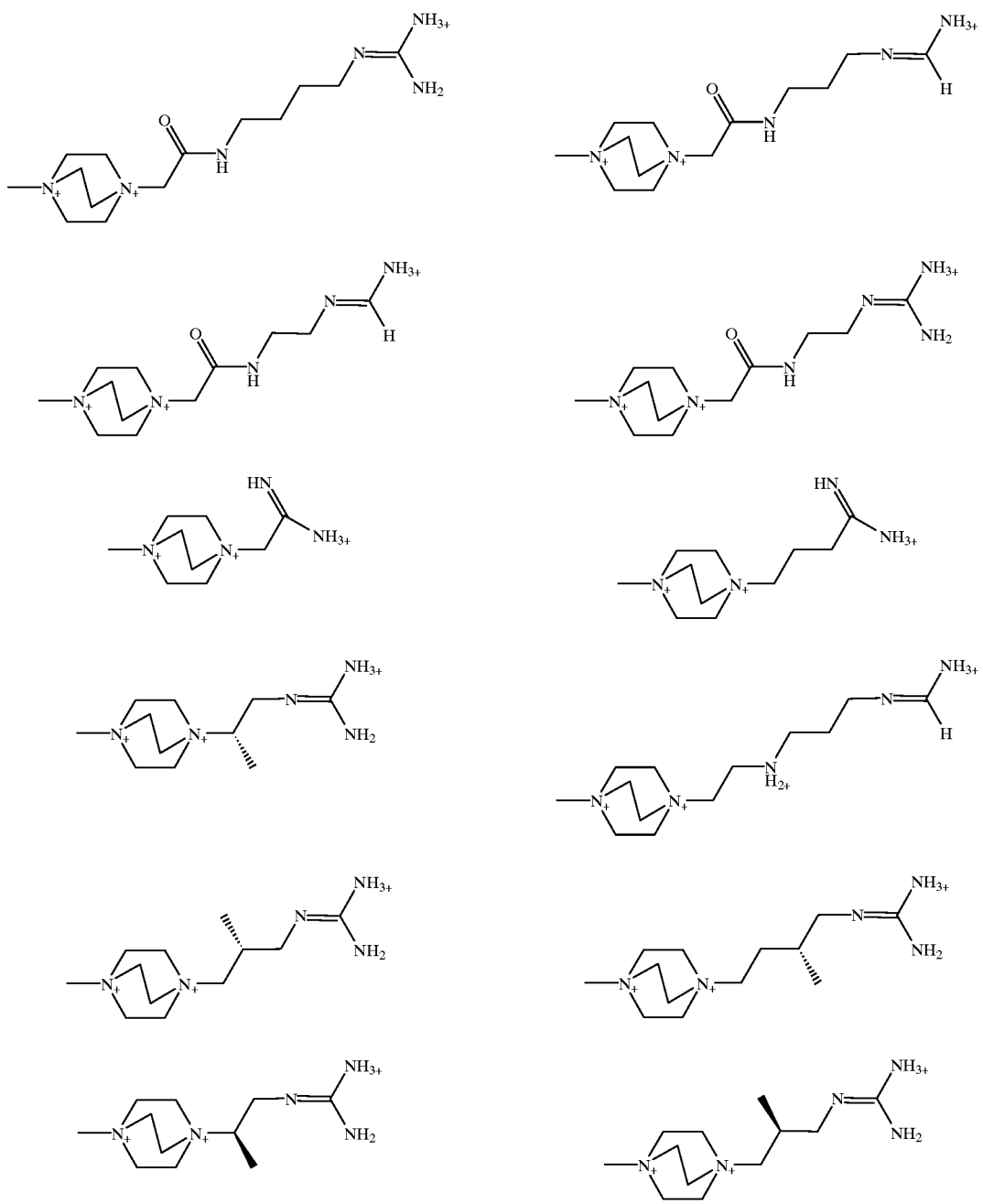

TABLE I-continued
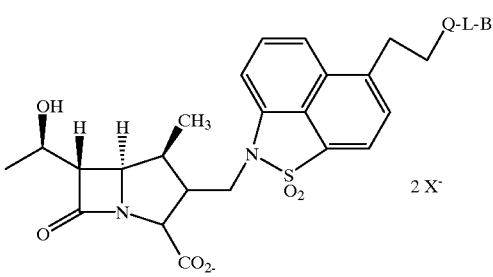
Q-L-B =
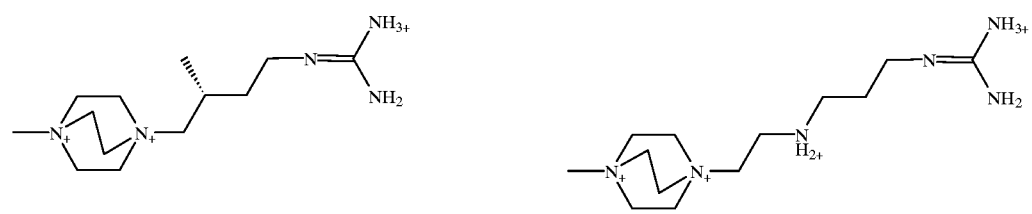
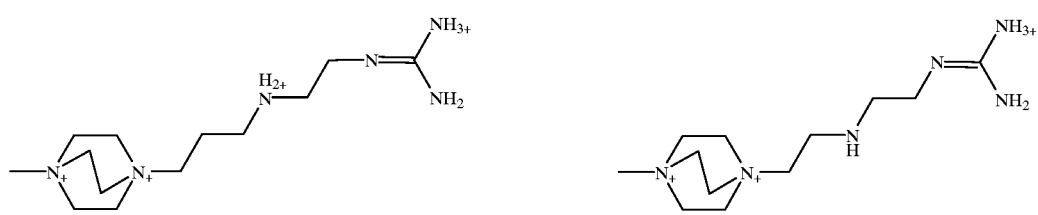
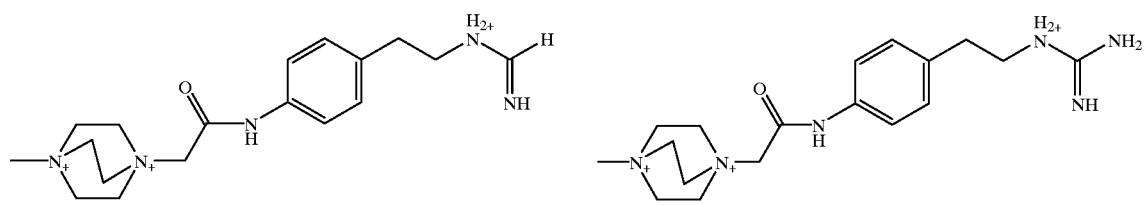

TABLE I-continued
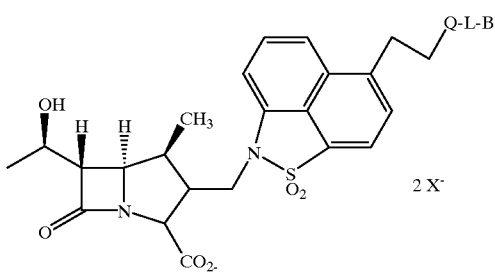
Q-L-B =
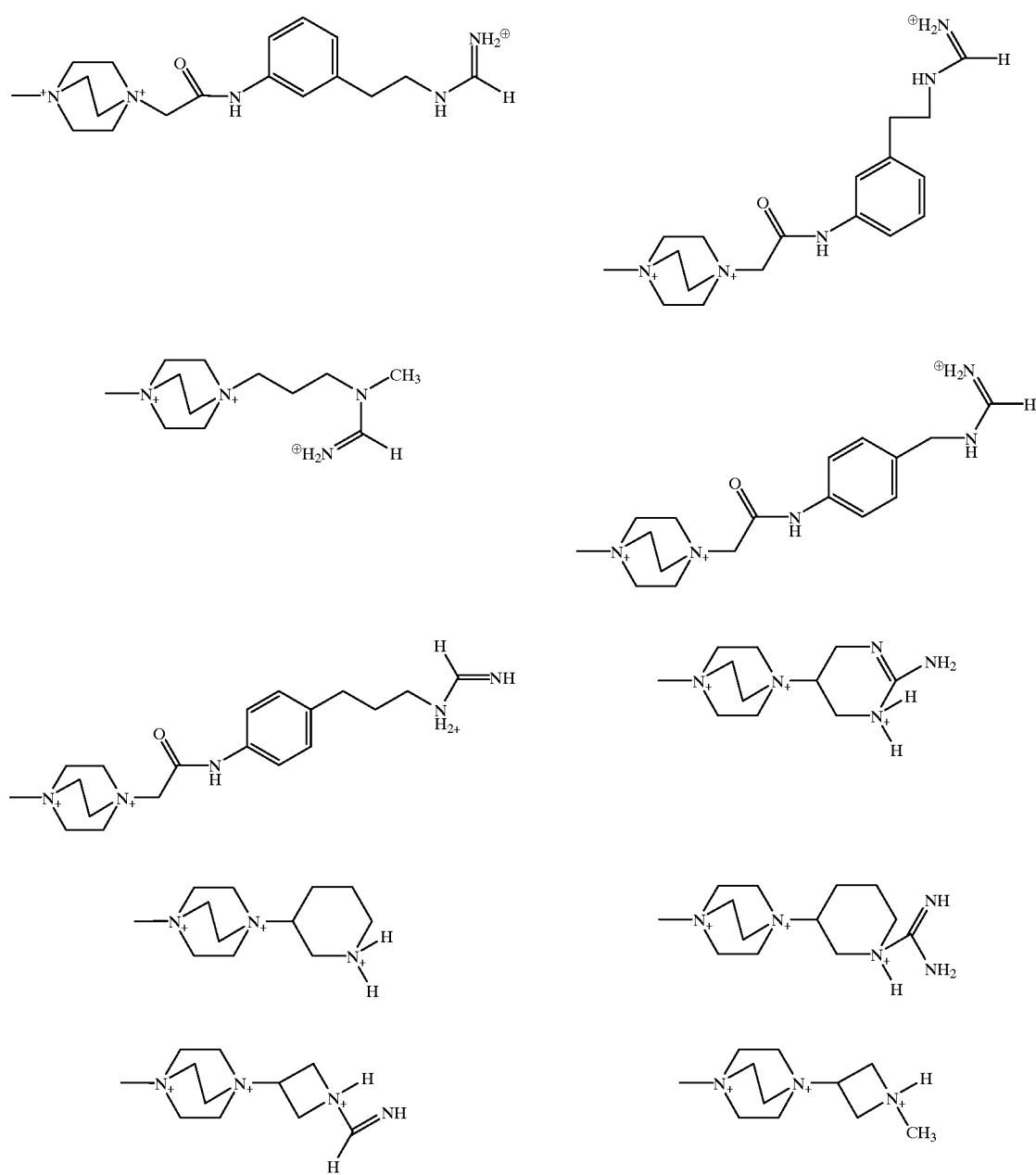

TABLE I-continued
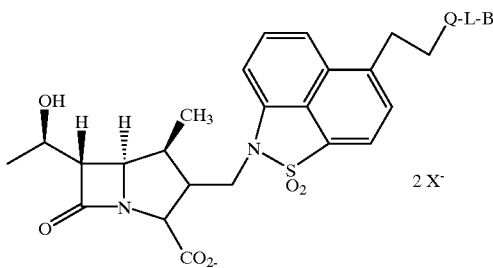
Q-L-B =
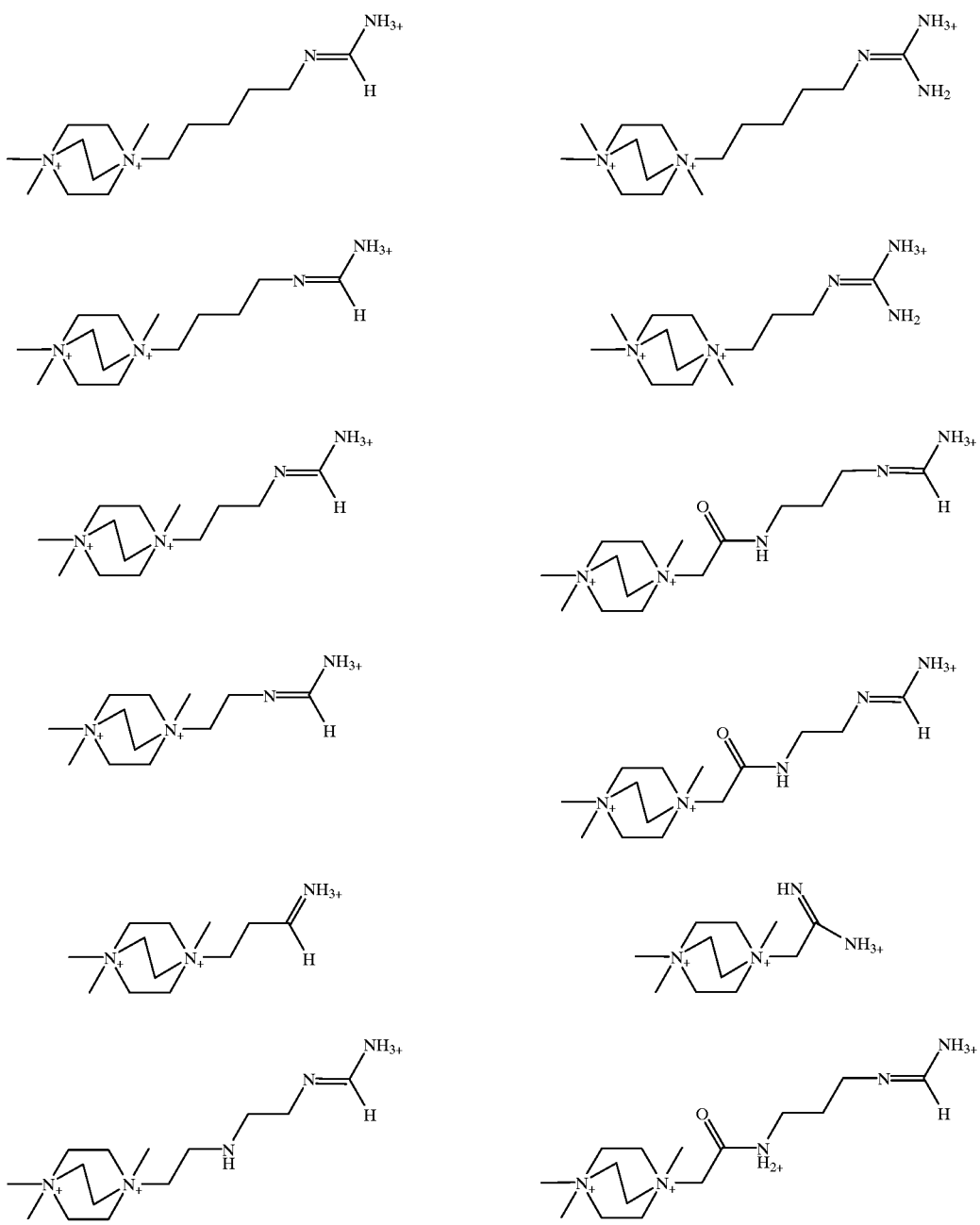

TABLE I-continued
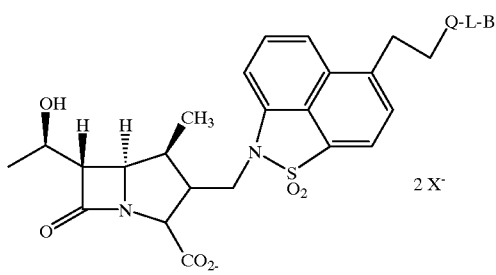
Q-L-B =
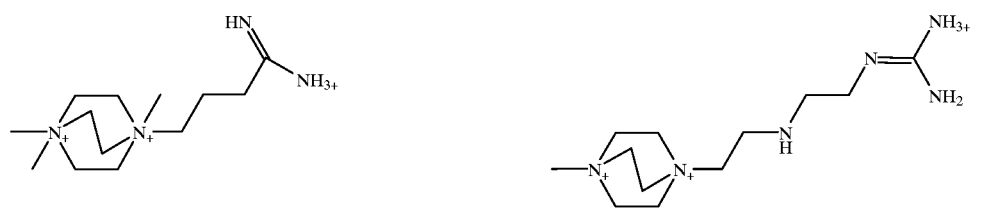
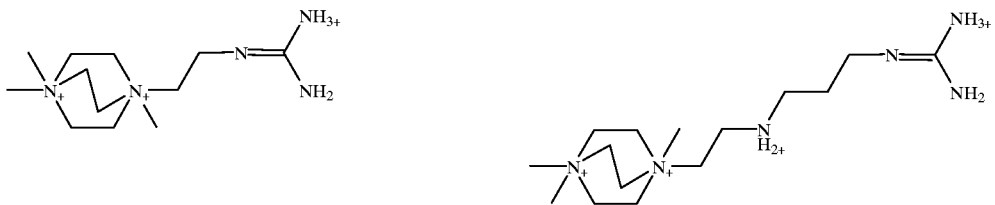
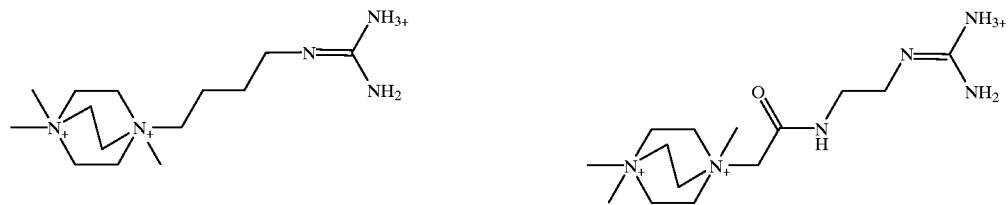
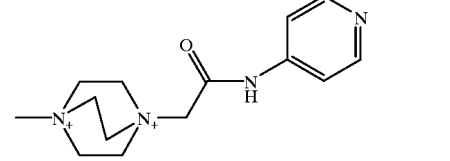

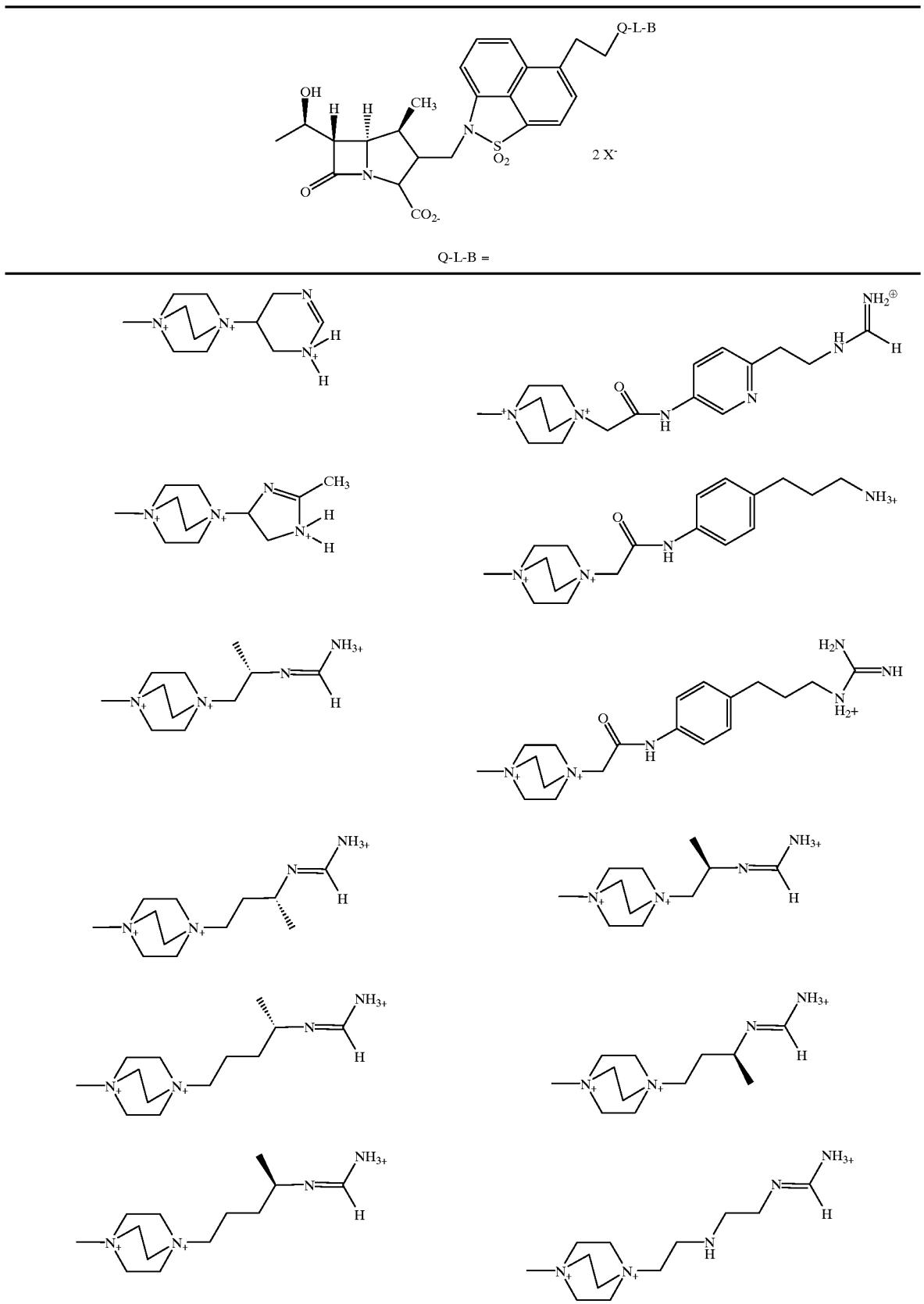

TABLE I-continued
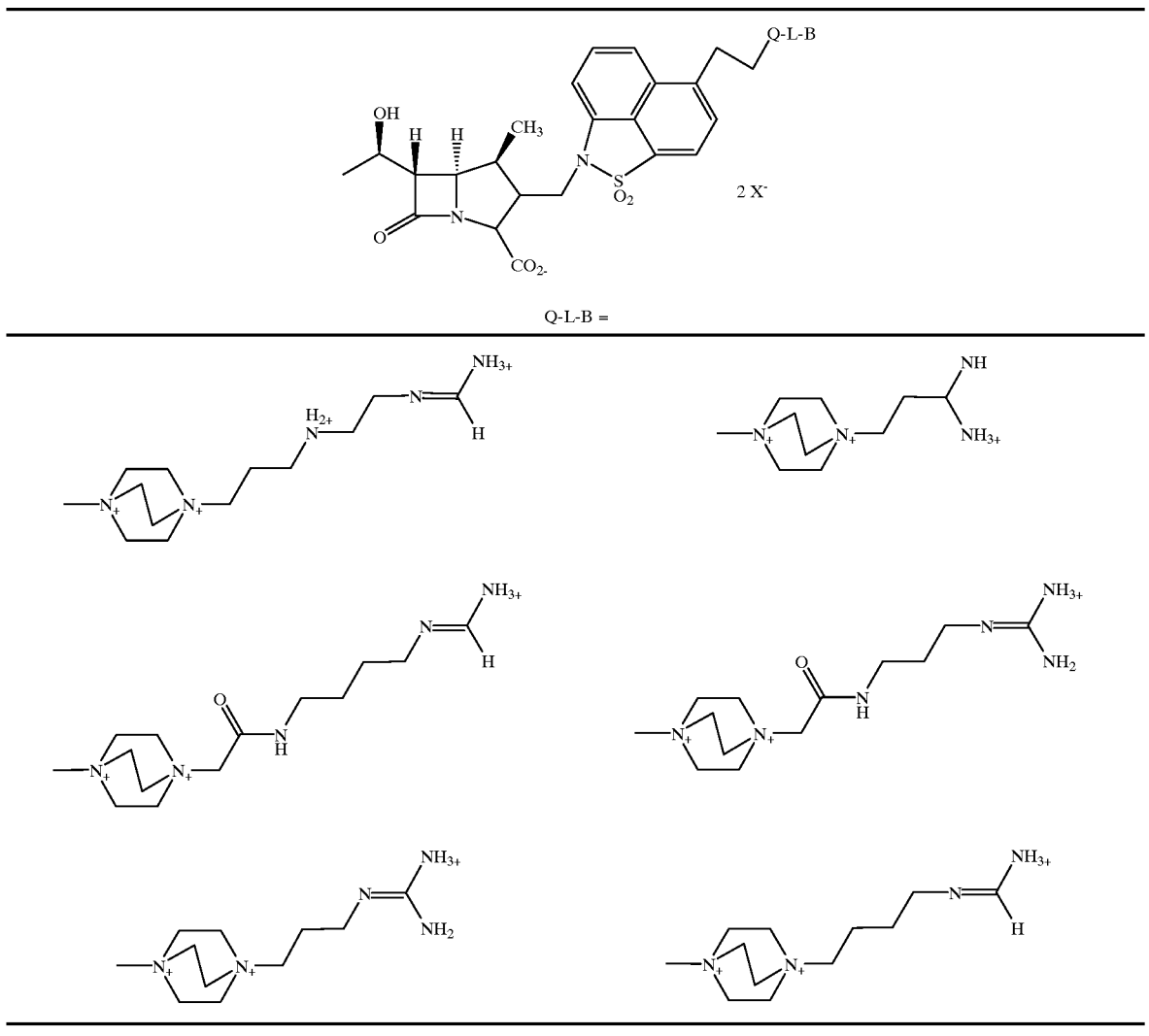
TABLE II
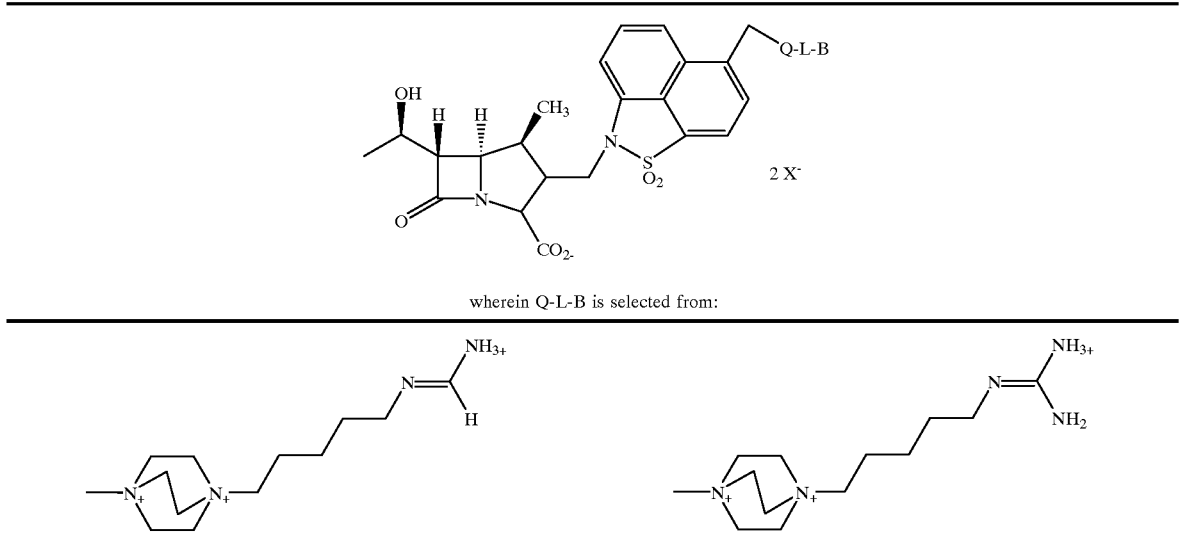
wherein Q-L-B is selected from:

TABLE II-continued
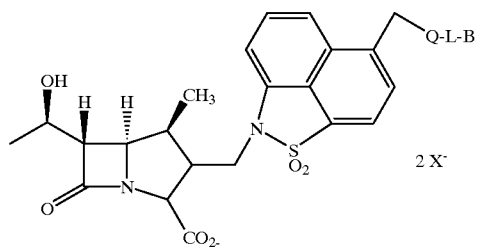
2 X⁻
wherein Q-L-B is selected from:
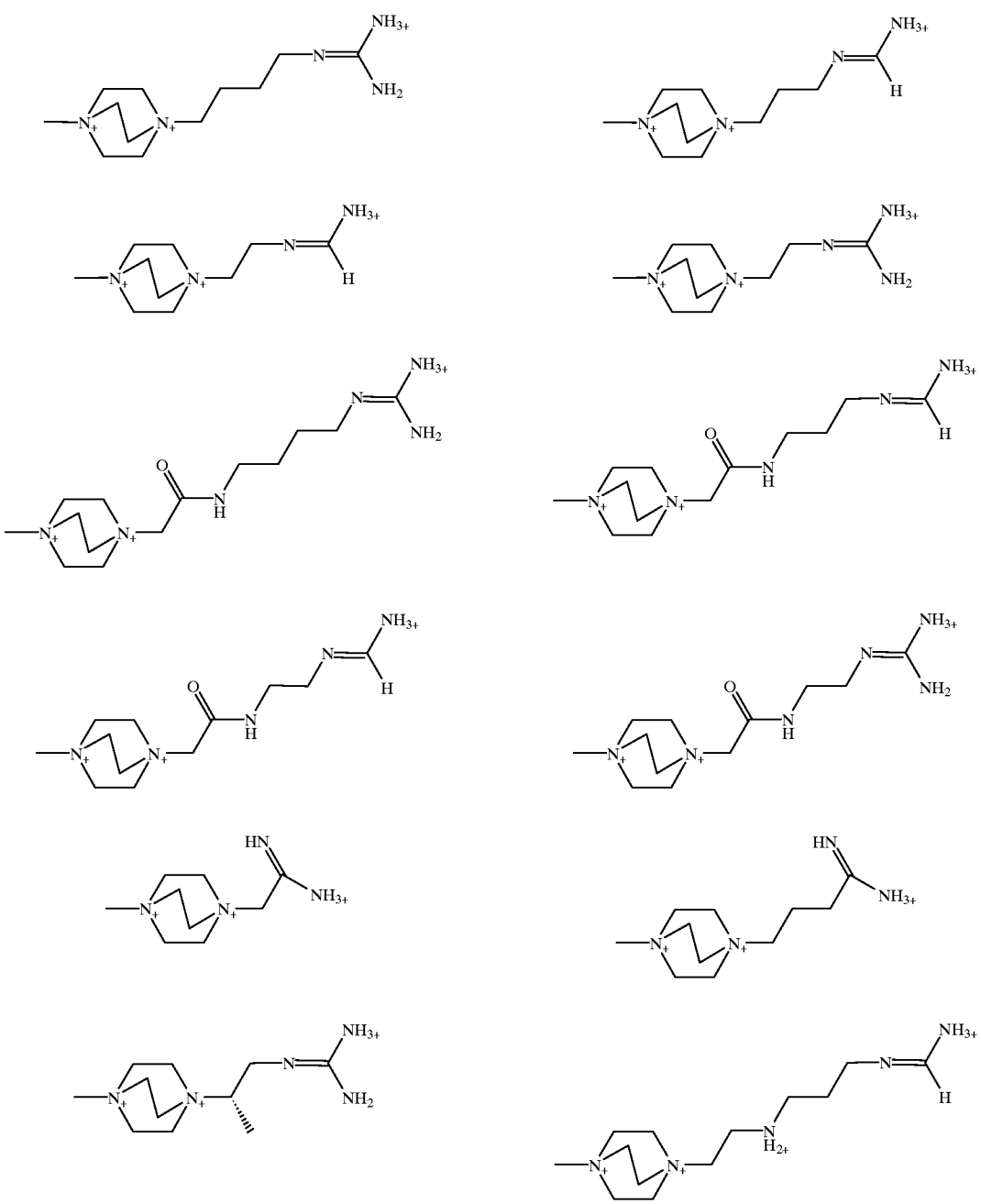

TABLE II-continued
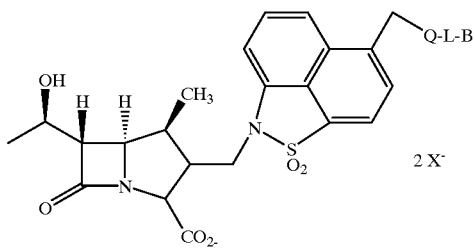
wherein Q-L-B is selected from:
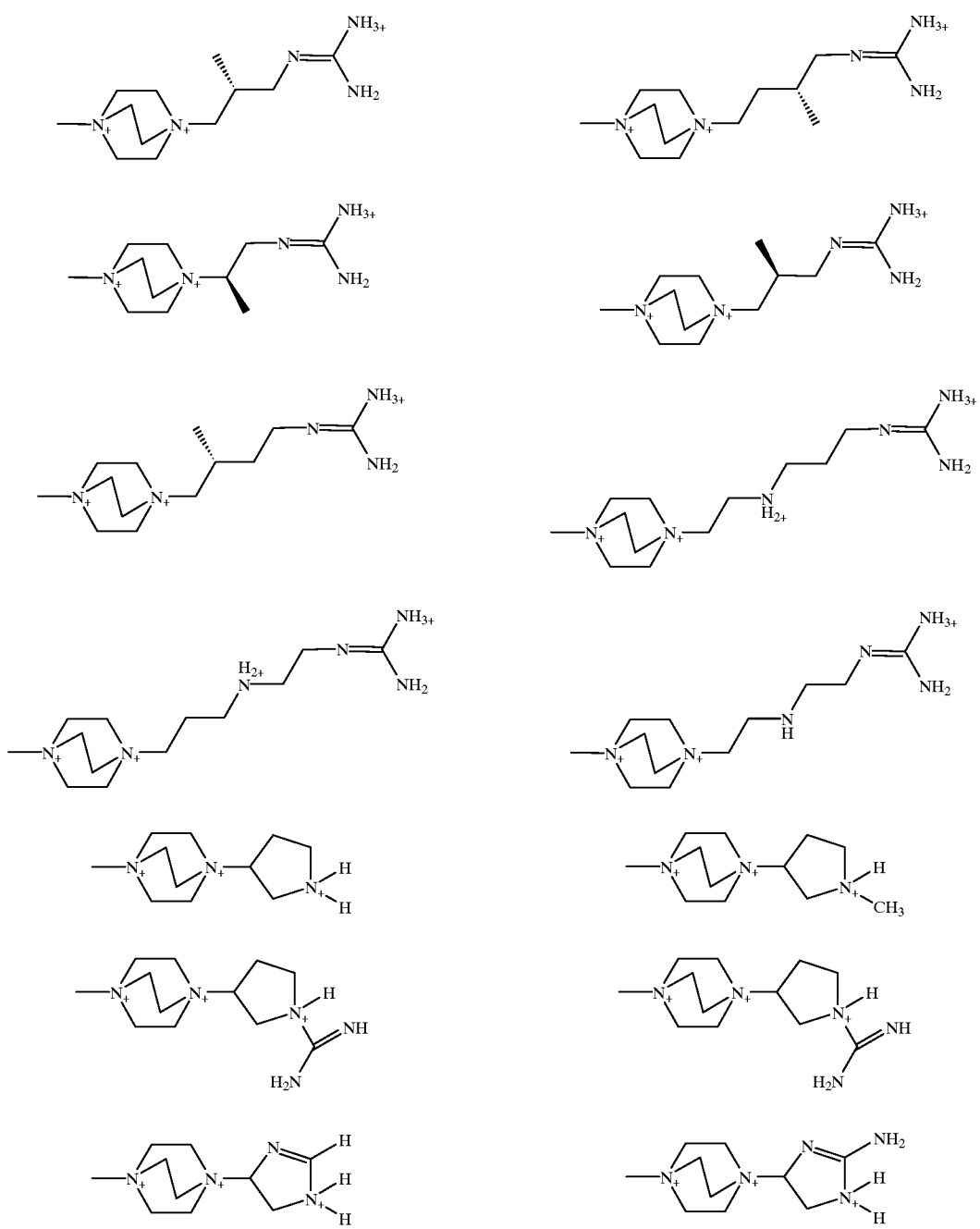

TABLE II-continued
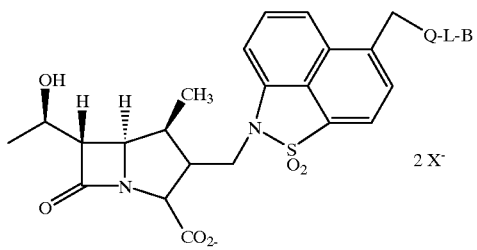
wherein Q-L-B is selected from:
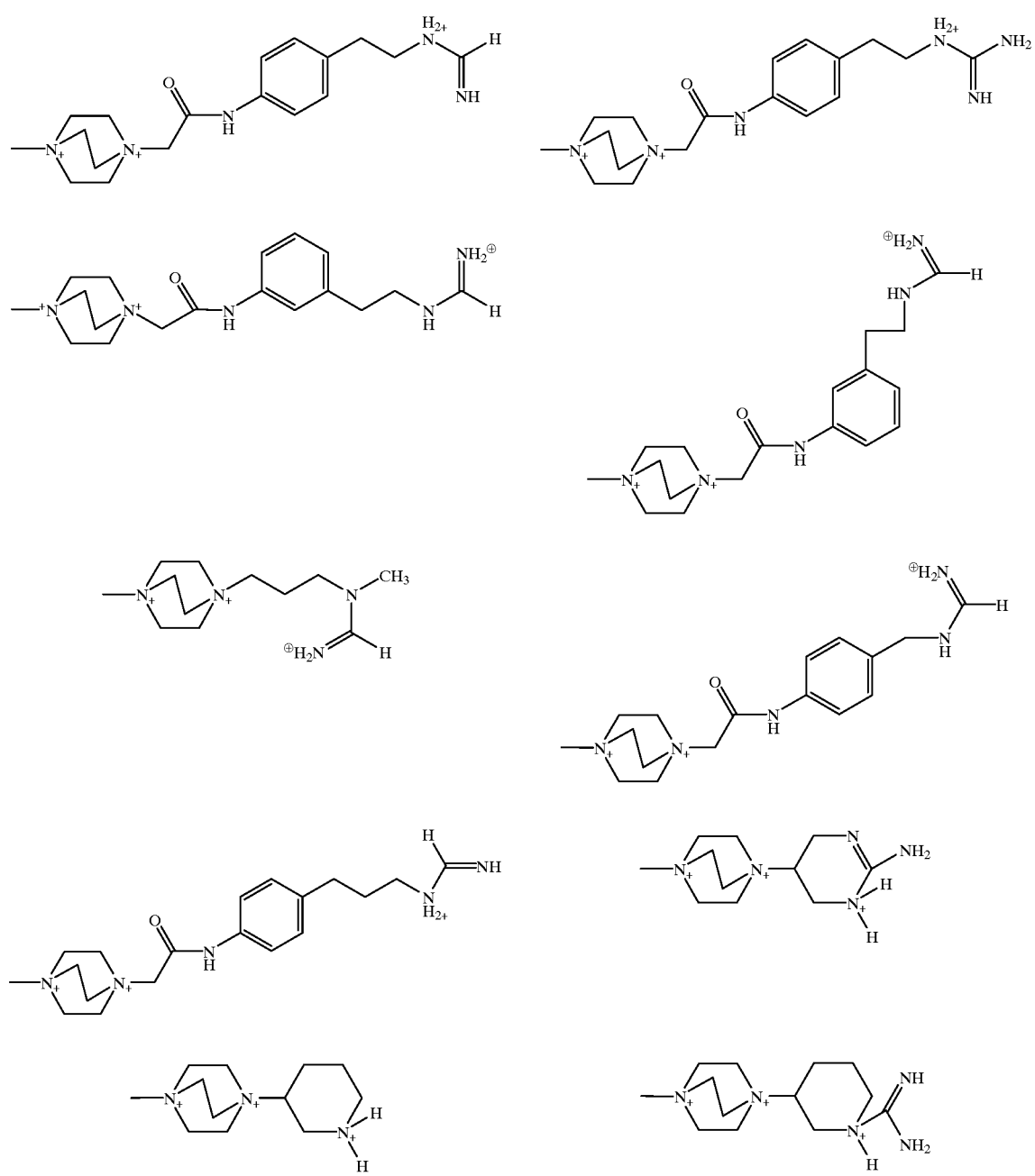

TABLE II-continued
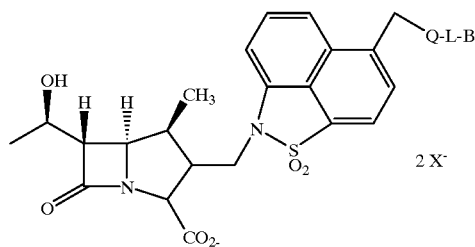
wherein Q-L-B is selected from:
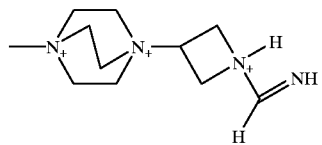 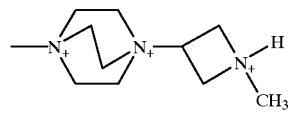
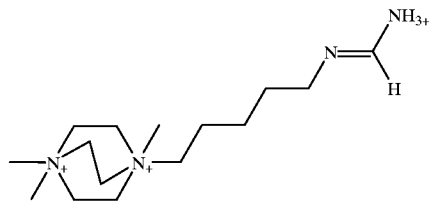 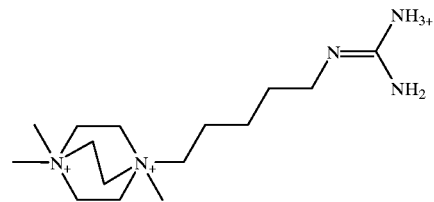
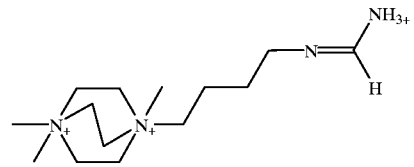 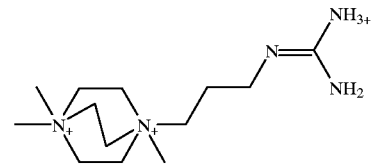
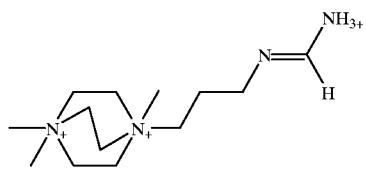 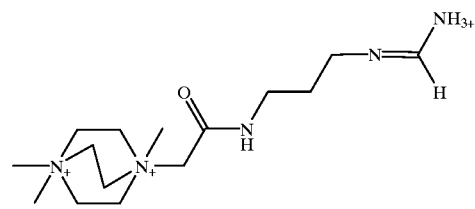
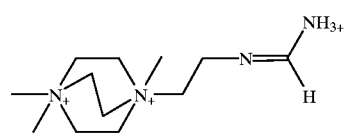 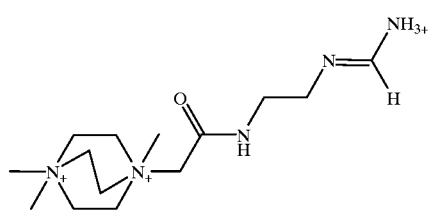
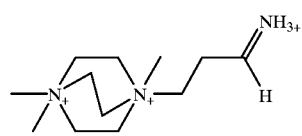 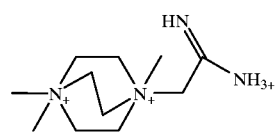

TABLE II-continued
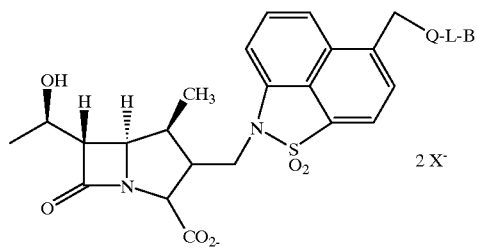
wherein Q-L-B is selected from:
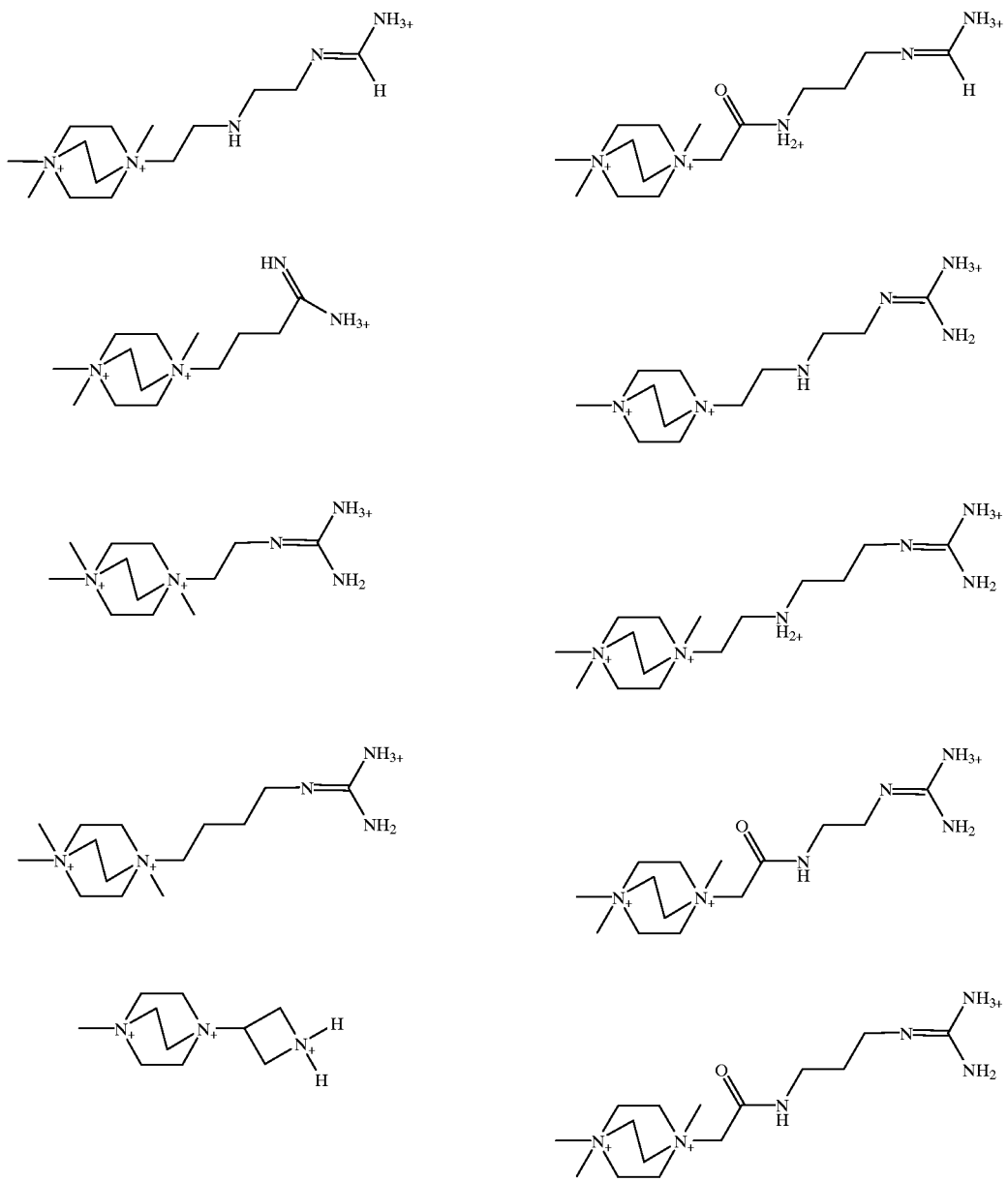

TABLE II-continued
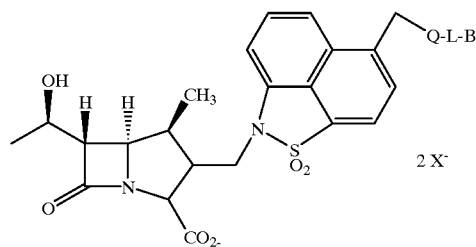
wherein Q-L-B is selected from:
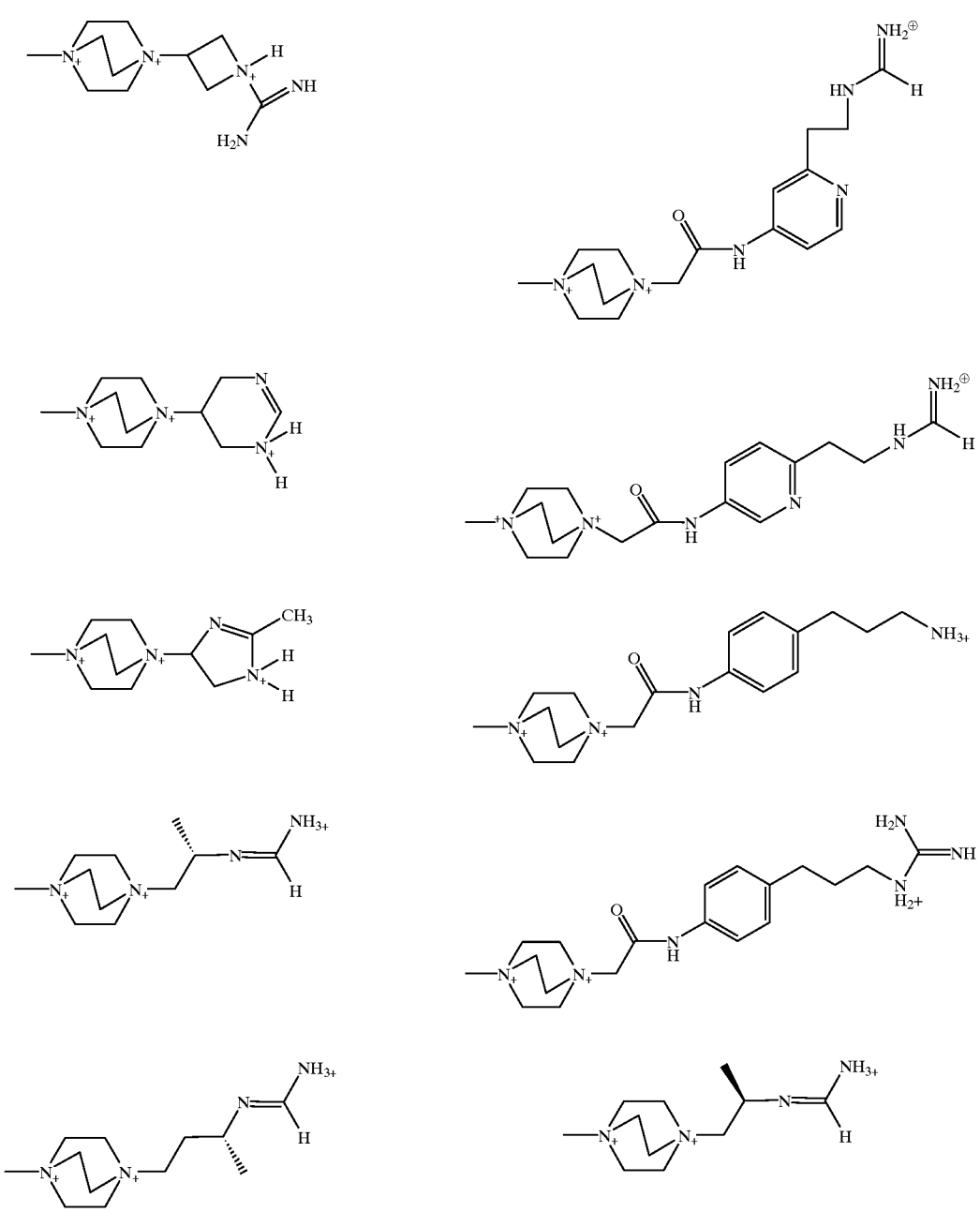

TABLE II-continued
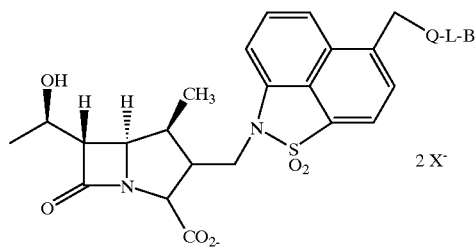
wherein Q-L-B is selected from:
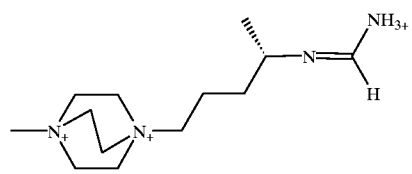 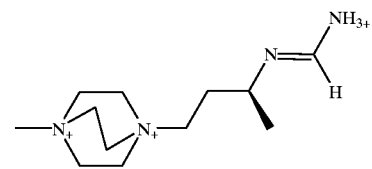
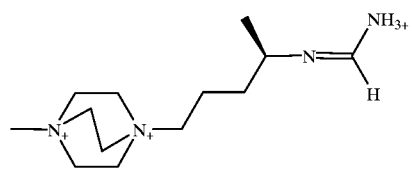 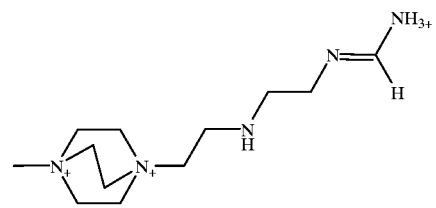
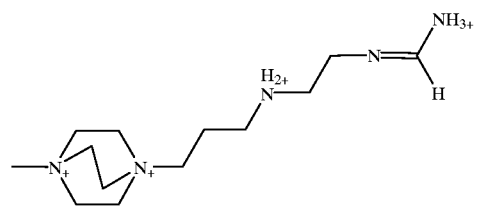 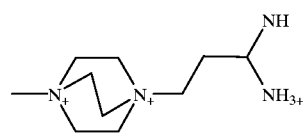
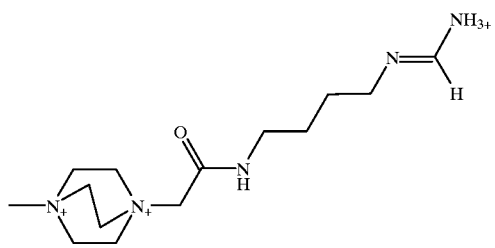 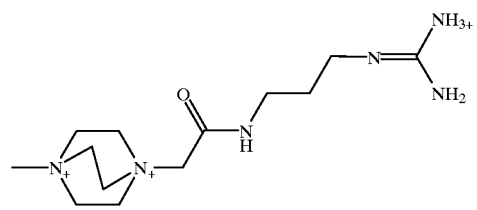
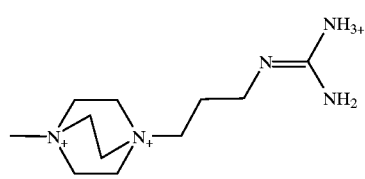 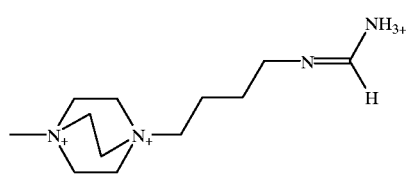

TABLE III
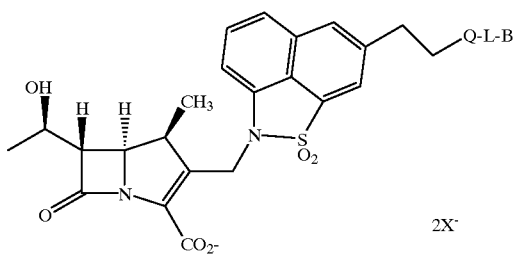
wherein Q-L-B is selected from:
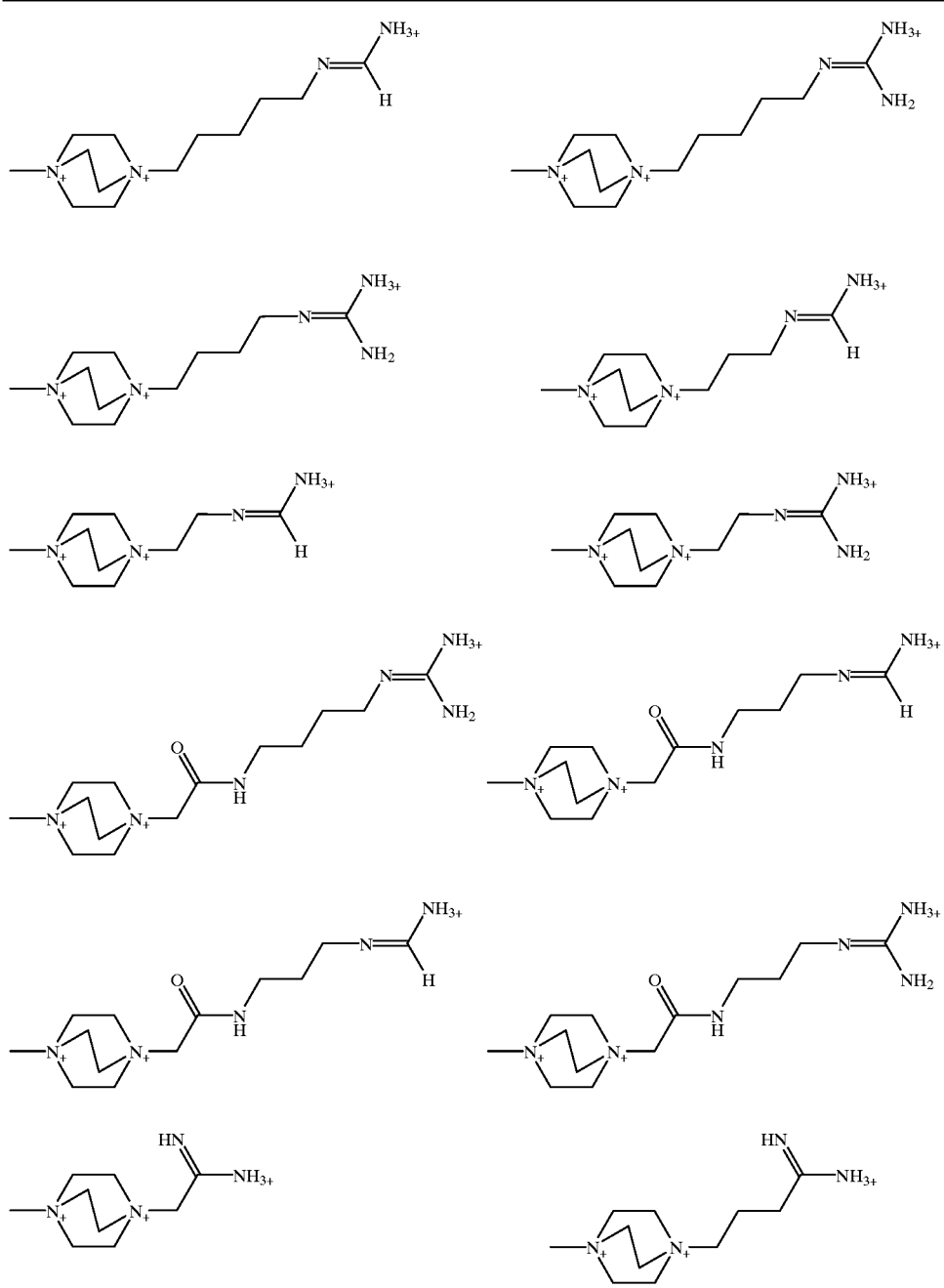

TABLE III-continued
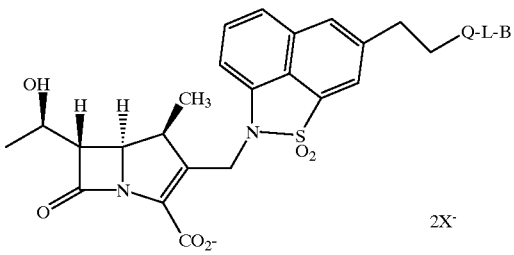
wherein Q-L-B is selected from:
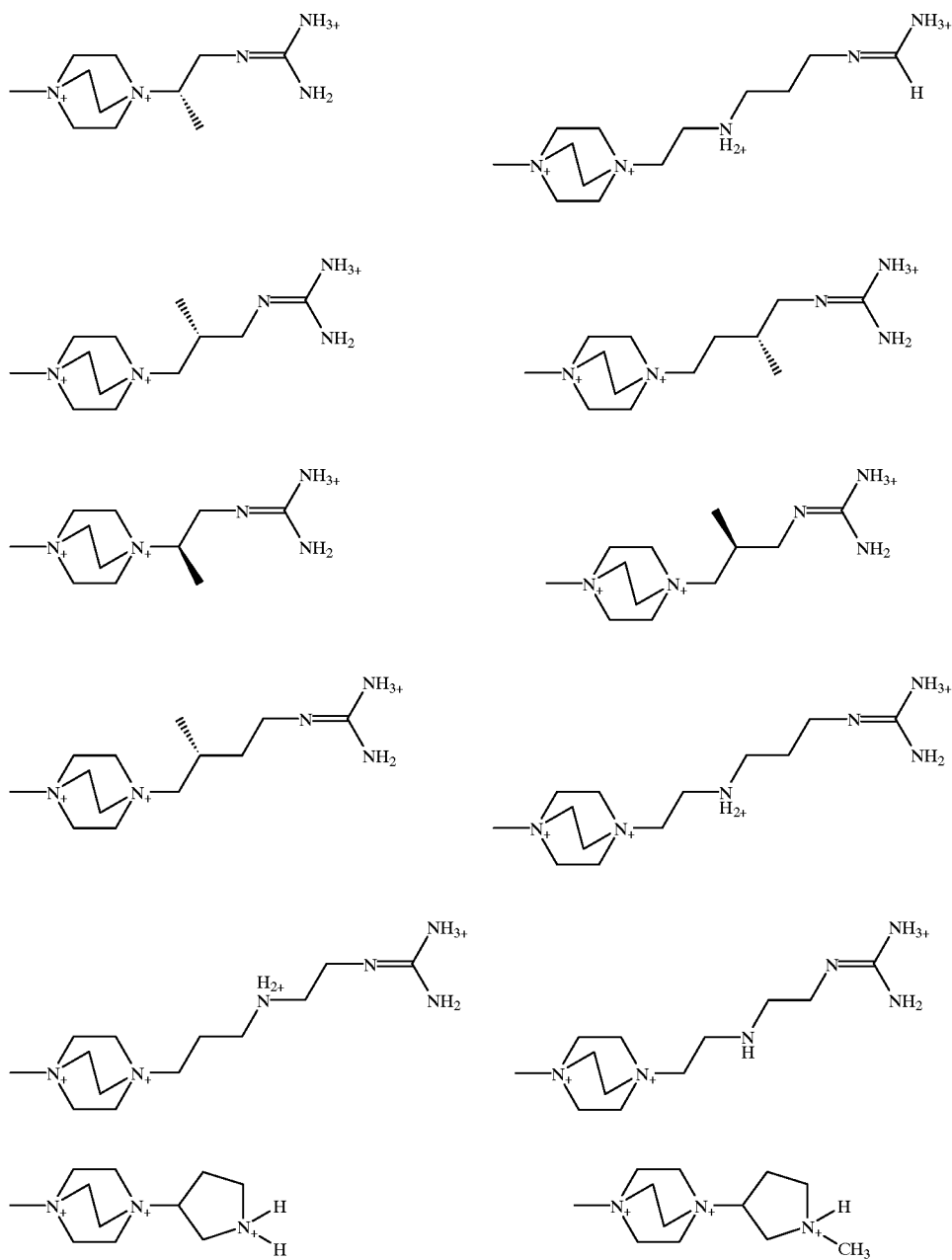

TABLE III-continued
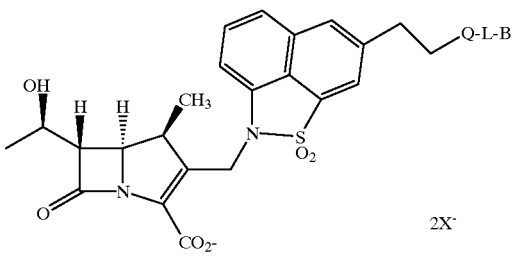
2X⁻
wherein Q-L-B is selected from:
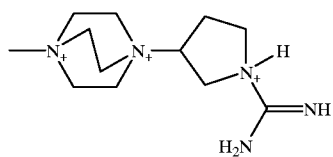 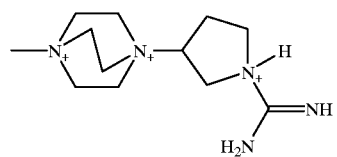
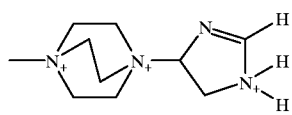 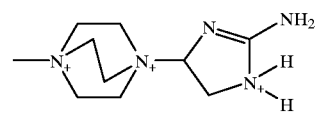
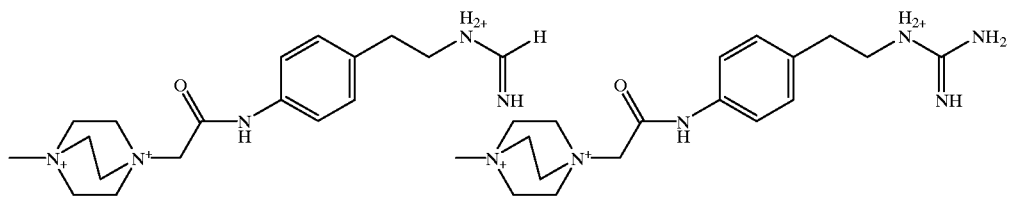
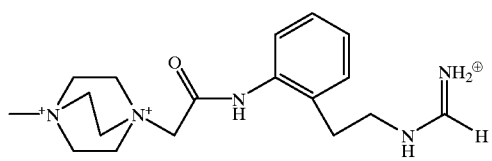
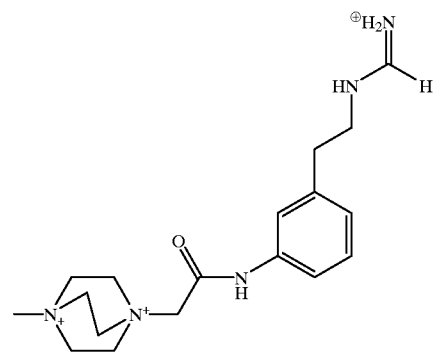
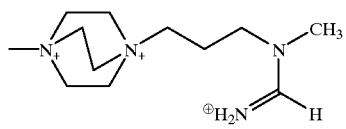
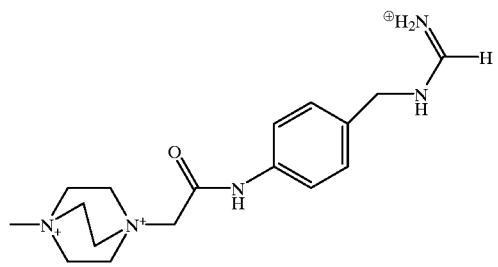

TABLE III-continued
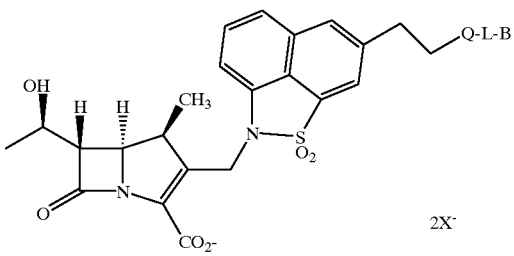
wherein Q-L-B is selected from:
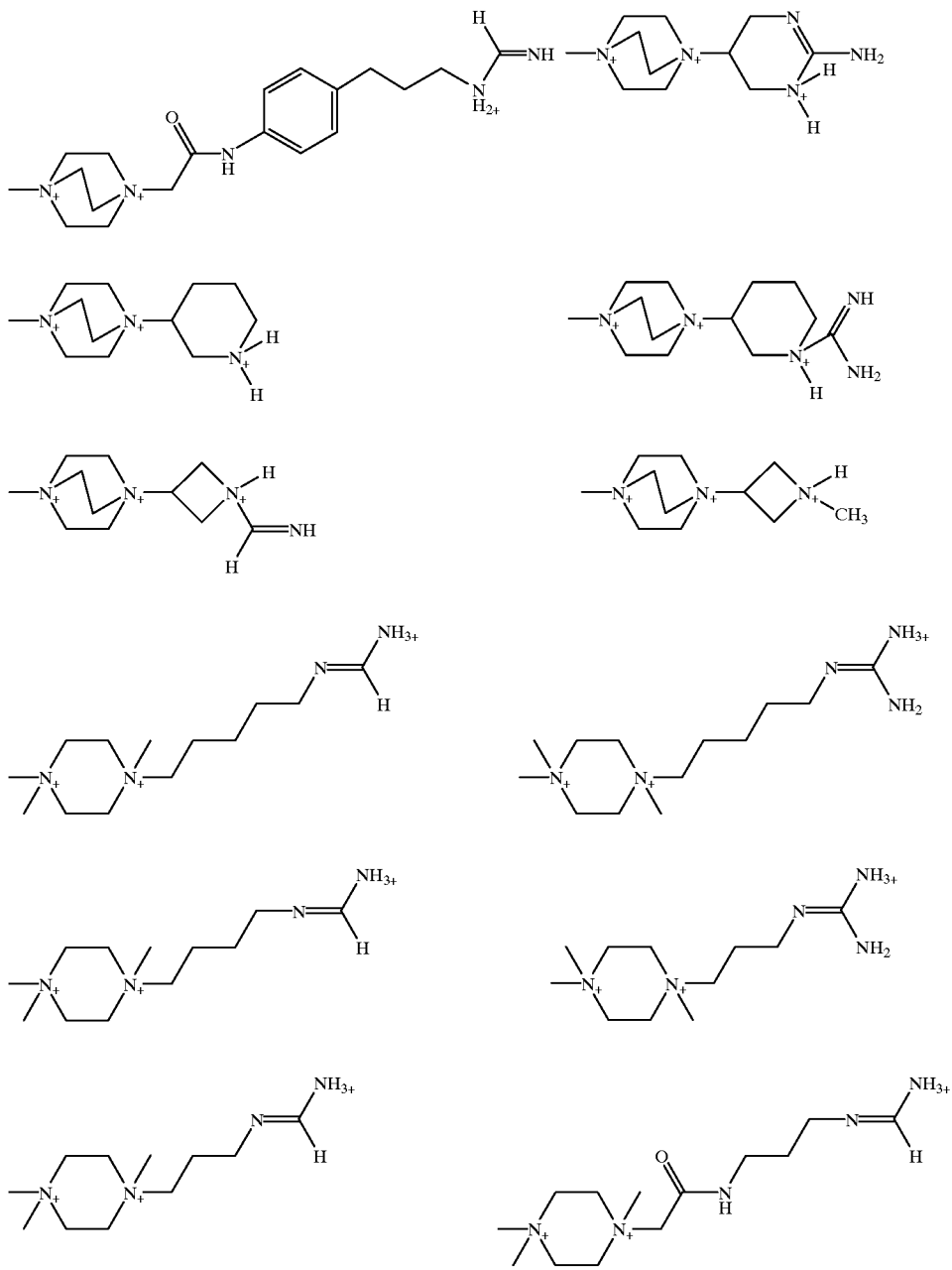

TABLE III-continued
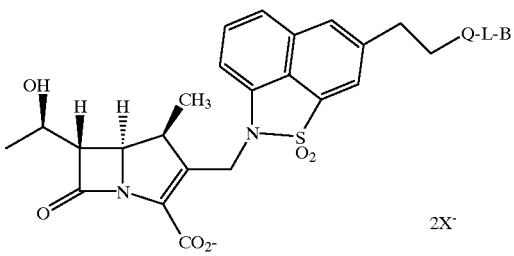
wherein Q-L-B is selected from:
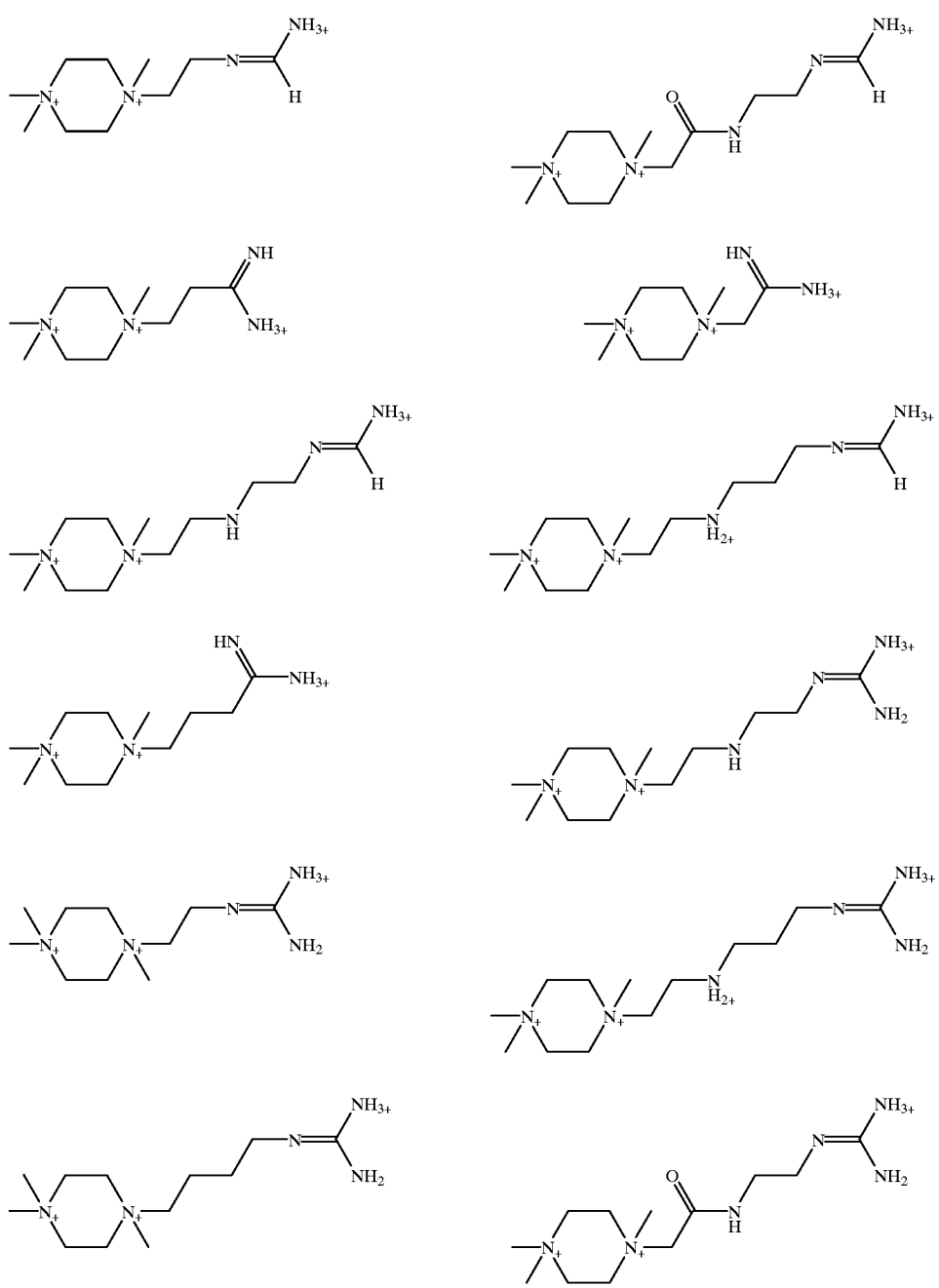

TABLE III-continued
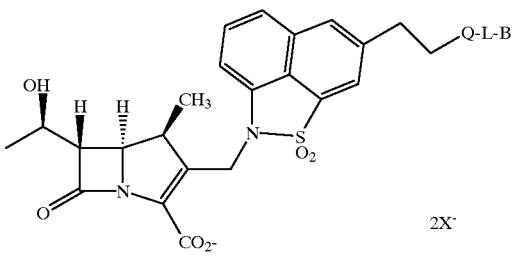
wherein Q-L-B is selected from:
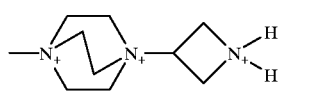
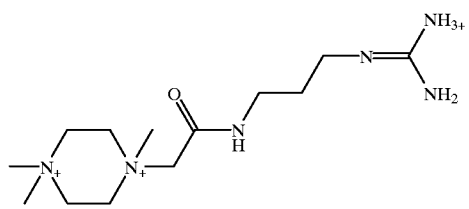
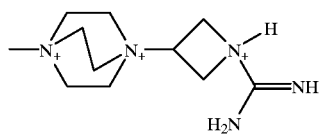
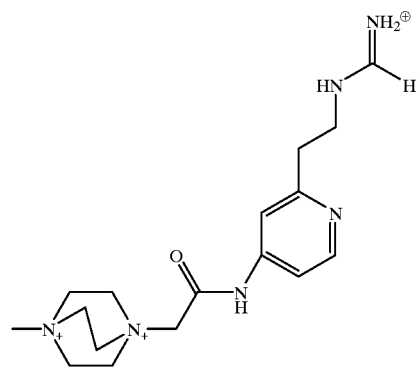
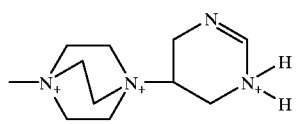
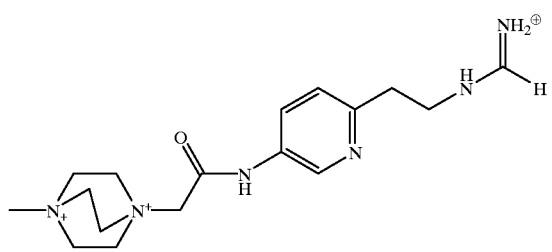
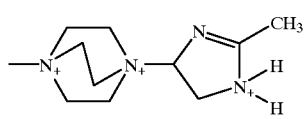
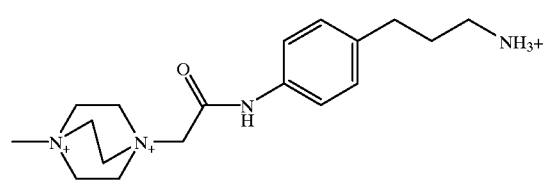
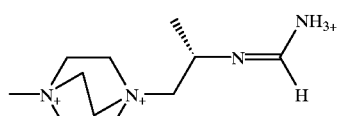
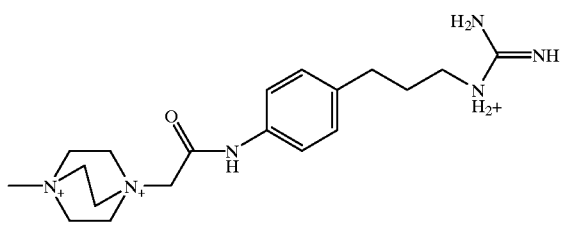

TABLE III-continued
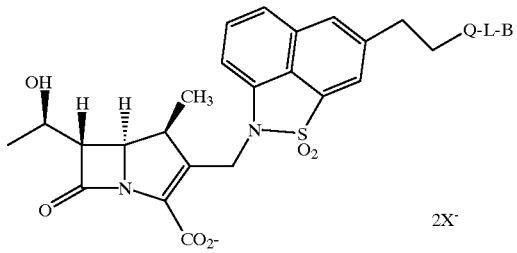
wherein Q-L-B is selected from:
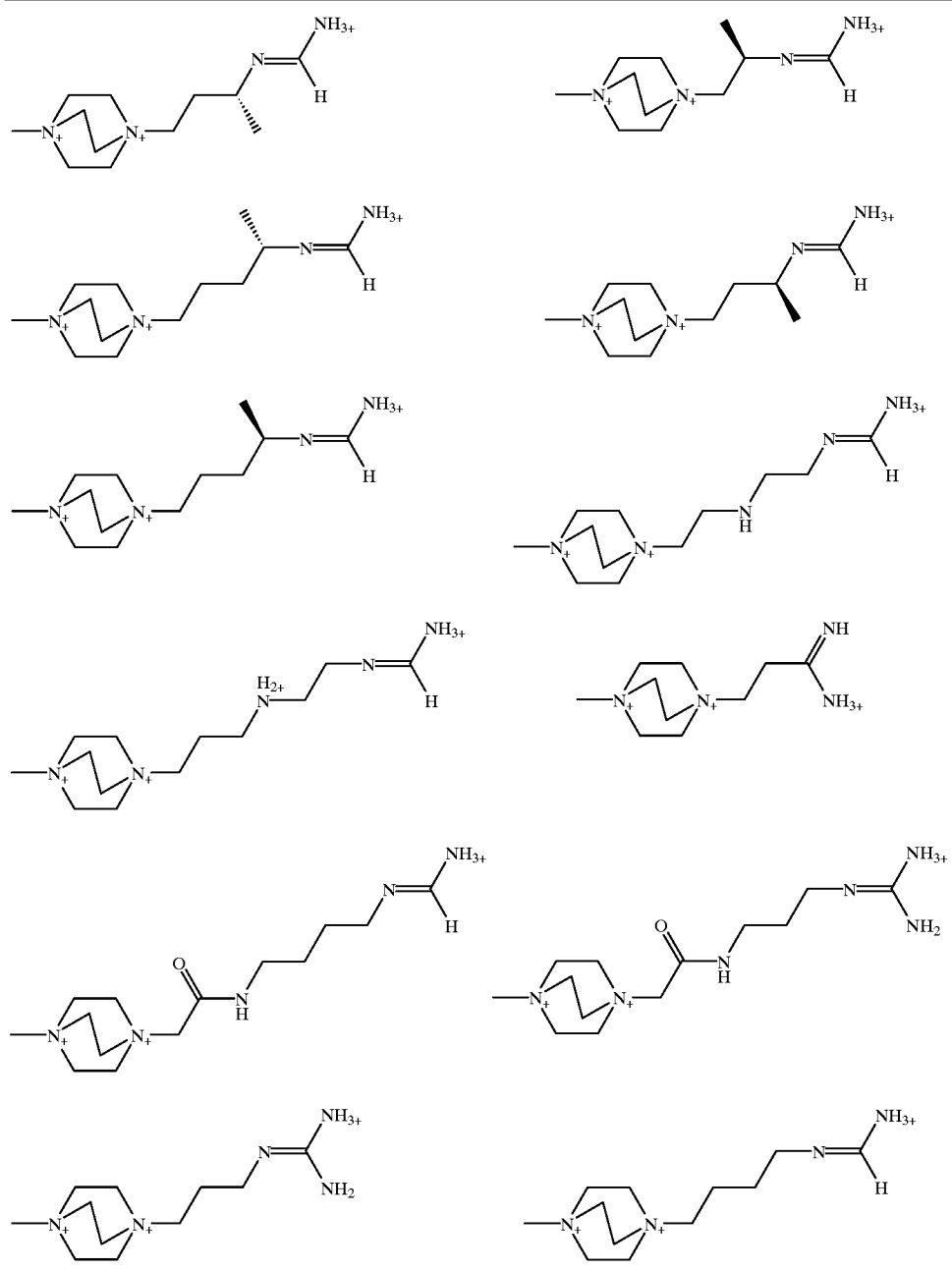

The process is illustrated by the following generic scheme:

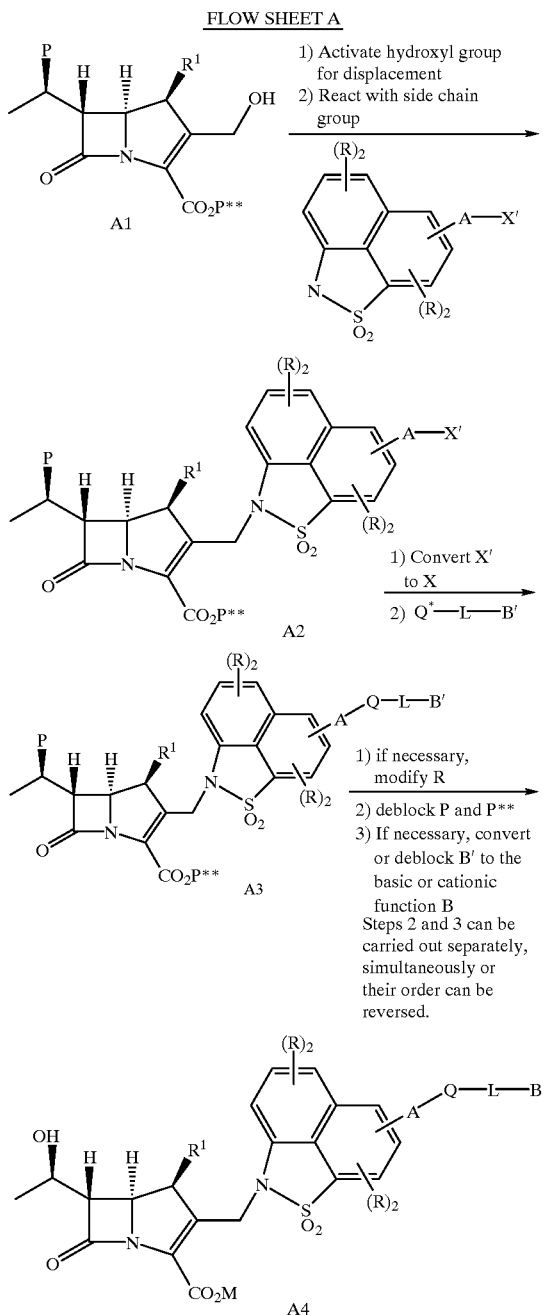

FLOW SHEET A

P = OH or hydroxyl protecting group
P** = carboxyl protecting group
X' = Precursor to X
X = a leaving group on A
Q* = monoalkylated monocationic precursor
 to the dialkylated, dicationic group Q
R, A, Q, L and B as defined in the scope of the invention
B' is a protected form of B, a precursor to B, or B' = B With reference to Flow Sheet A above, P, $R^1$, R, and M, are as defined with respect to the compounds of formula I.

P** represents a carboxyl protecting group.

Q*-L-B' represents a group which reacts with intermediate A2 (upon activation of A2) in a manner which results in the incorporation in the final product of a member of the group defined as Q-L-B above, thus Q*-L-B' may be viewed as a precursor for Q-L-B.

The naphthosultam side chain group used in the synthesis of the compounds of the present invention have, in some cases, been described in the chemical literature. In other cases, precursor compounds which may be readily converted to the requisite naphthosultam have been described in the literature. In cases where the requisite naphthosultam is not known in the literature it is neceessary to synthesize the naphthosultam by a newly developed synthesis. One skilled in the art can adapt a previously published synthesis of an analogous naphthosultam to prepare the requisite compound in a straightforward manner without undue experimentation. Examples of naphthosultam synthesis are described herein (see below).

The naphthosultam side chain group is initially reacted with a suitably protected carbapen-2-em-3-carboxylate having an activated hydroxymethyl group at the 2-position.

The carbapenem nucleus having a —$CH_2OH$ substituent at position 2 can be obtained in accordance with Schmitt, S. M. et al., *J. Antibiotics* 41(6): 780–787 (1988), the teachings of which are incorporated herein by reference. The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

The addition of the naphthosultam side chain group to the carbapenem is accomplished by treating a solution of the hydroxymethyl-carbapenem and the naphthosultam side chain group in a suitable solvent such as tetrahydrofuran (THF), ether, acetonitrile, dimethylformamide (DMF), benzene, dimethylsulfoxide (DMSO), and the like with a (premixed) suitable activating reagent such as diethyl azodicarboxylate (DEAD) / triphenylphosphine, diisopropyl azodicarboxylate (DIAD) / tributylphosphine, and the like, at a temperature between about −20° C. and 35° C. for about 5 to 90 minutes.

Alternatively, the naphthosultam and carbapenem can be mixed together with either the azodicarboxylate or the phosphine reagent in a suitable solvent and the other component of the activating reagent (the phosphine or the azodicarboxylate, respectively) can be added to that mixture. Once the naphthosultam, carbapenem, and activating reagent(s) have been mixed, the reaction is allowed to proceed at a temperature between about −20° C. and 35° C. for about 5 to 90 minutes.

The resulting mixture is then subjected to a standard work-up procedure familiar to those skilled in the art to afford a crude 2-naphthosultam-methyl substituted carbapenem which is purified, if necessary, by recrystallization or by chromatography on silica gel, eluting with a suitable solvent or mixture of two or more solvents, such as hexane, ethyl acetate, ether, benzene, dichloromethane, chloroform, acetone, methanol and the like.

Modification of the naphthosultam side chain of compounds A2, which is generally necessary to introduce the charged substituent of A4, is best accomplished before removal of the protecting groups. For compounds which contain a hydroxyl group (X') in the side chain, a positively charged substituent may be introduced into the side chain by first activating the hydroxyl group by converting it to a suitable leaving group (X) such as a triflate, mesylate, tosylate, iodide, chloride, bromide, and the like, and then displacing the resulting leaving group with a compound Q*, such as a suitably substituted diazabicyclooctane or a suitably substituted N,N-dimethylpiperazine. Alternatively, in some cases, the charged substituent may be incorporated in the naphthosultam side chain before addition of the naphthosultam to the carbapenem or may be introduced after deprotection of A2. However, introduction of the charged substituent by modification of A2 before deprotection is greatly preferred.

In some cases, activation of the hydroxyl group and displacement by Q* to produce A3 may be accomplished in a single step by taking advantage of the basic character of compound Q* and using it as a base in the activation reaction.

The conversion of the hydroxyl group to a suitable leaving group is accomplished by treating the hydroxyl substituted compound in a suitable solvent such as dichloromethane, tetrahydrofuran, ether, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, tributylamine, diisopropylethylamine, and the like at a temperature between about −100° C. and 0° C. for about 5 to 120 minutes. The intermediate thus obtained contains a leaving group, which may be converted to an alternative leaving group, iodide, by treating a solution of the intermediate in a suitable solvent such as acetone, methyl ethyl ketone, and the like at about −10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting the activated intermediate with reagent Q*. In some cases, activation and displacement of the hydroxyl group may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO, and the like as described in the preceding paragraphs. The resulting activated intermediate is treated with 1–3 molar equivalents of compound Q* at a temperature between about −78° C. and 50° C. for about 15 to 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q* is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q*. A silver salt of a non-nucleophilic acid, such as silver trifluoromethanesulfonate, silver tetrafluoroborate and the like is then added. Although the reaction will proceed in the absence of the silver salt, the reaction proceeds more rapidly in the presence of the silver salt. In addition, the silver salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

The synthesis of the target compound is completed by removing any protecting groups which are present in the penultimate intermediate using standard techniques which are well known to those skilled in the art. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable antibacterial agents active against various Gram-positive and Gram-negative bacteria, and accordingly find utility in human and veterinary medicine.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The invention is illustrated with the following non-limiting examples.

PREPARATIVE EXAMPLE 1

SYNTHESIS OF 4-(2-TRIETHYLSILANYLOXY-ETHYL)-1,8-NAPHTHOSULTAM

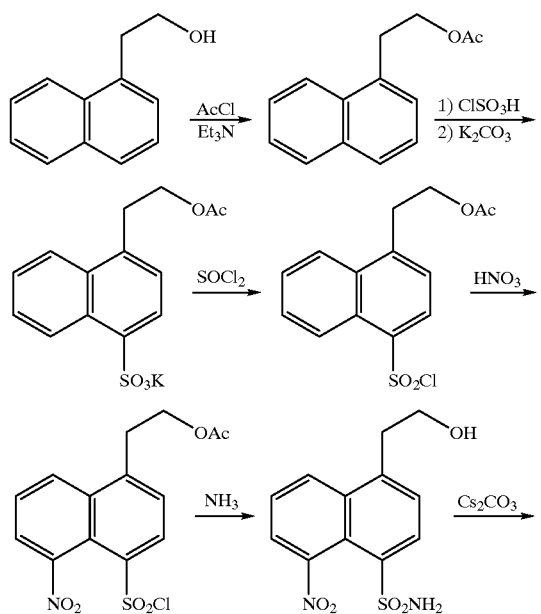

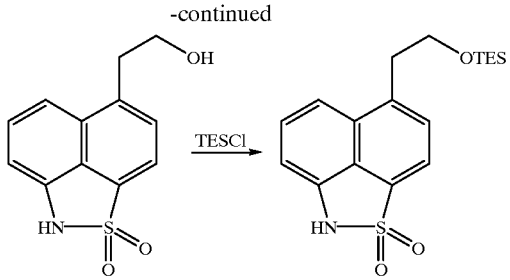

Step 1: 1-(2-Acetoxy-ethyl)-naphthalene

Triethylamine (691 mL, 4.96 mol) was added to an ice cold solution of 1-(2-hydroxy-ethyl)-naphthalene (569 g, 3.30 mol) in dichloromethane (2.2 L). Acetyl chloride (282 mL, 3.97 mol) was added dropwise over 90 minutes. After the addition was complete, the reaction mixture was stirred for an additional 30 minutes with ice-bath cooling. The reaction mixture was washed sequentially with water (2×1 L), 1N HCl (1 L, 500 mL), water (1 L), 5% aqueous $NaHCO_3$ (500 mL), water (1 L), and brine (500 mL), then dried over magnesium sulfate, filtered, and evaporated to afford 1-(2-acetoxy-ethyl)-naphthalene (723.2 g) as a yellow oil that slowly crystallized.

Step 2: Potassium 4-(2-acetoxy-ethyl)-naphthalene-1-sulfonate

Chlorosulfonic acid (69.3 g, 590 mmol) was added dropwise over 17 minutes to a solution of 1-(2-acetoxy-ethyl)-naphthalene (105.5 g, 490 mmol) in dichloromethane (200 mL). The reaction was exothermic and periodic ice-bath cooling was employed to maintain the internal temperature at 25–30° C. Approximately 10 minutes into the $CLSO_3H$ addition, voluminous evolution of HCl gas was observed. Mter the addition was complete, the reaction mixture was stirred at room temperature for 3 hours then cautiously added to ice (400 g). After shaking, the layers were separated. The aqueous layer was washed with dichloromethane then slowly neutralized by addition of a solution of potassium carbonate (77 g, 560 mmol) in water (200 mL). The precipitate was collected by filtration, washed with cold water (100 mL), then dried under vacuum at 60° C. to afford potassium 4-(2-acetoxy-ethyl) naphthalene sulfonate (102.39 g) as a white solid. This material contained ca. 6% of the isomeric potassium 5-(2-acetoxy-ethyl)-1-naphthalene sulfonate as determined by 1H NMR. The filtrate was concentrated under vacuum to afford a white suspension (355 g) which was stored in a refrigerator overnight. The solid was collected by filtration, washed with cold water (100 mL), then dried under vacuum at 60° C. to afford a second crop of potassium 4-(2-acetoxy-ethyl)-naphthalene-1-sulfonate (10.67 g) as a white solid. The second crop contained ca. 14% of the isomeric potassium 5-(2-acetoxy-ethyl)-1-naphthalene sulfonate as determined by 1H NMR.

Step 3: 4-(2-Acetoxy-ethyl)-naphthalene-1-sulfonyl chloride

Potassium 4-(2-acetoxy-ethyl)-naphthalene-1-sulfonate (102.3 g, 308 mmol) was added in portions over 15 minutes to a room temperature solution of dimethylformamide (2.4 mL, 31 mmol) in thionyl chloride (112 mL, 1.54 mol). The reaction mixture was gradually brought to 80° C. (oil bath temperature) over 30 minutes and heated at 80° C. for 90 minutes, then cooled to room temperature and stirred at room temperature for 60 minutes. The reaction mixture was partitioned between ice water (500 mL) and ethyl acetate (500 mL). The organic layer was washed with water (200 mL) and brine (200 mL), dried over magnesium sulfate, filtered, and evaporated under vacuum to a cream colored solid. The crude product was triturated with pet ether to afford 4-(2-acetoxy-ethyl)-naphthalene-1-sulfonyl chloride as a pale tan solid (77.47 g).

Step 4: 4-(2-Acetoxy-ethyl)-8-nitro-naphthalene-1-sulfonyl chloride 4-(2-Acetoxy-ethyl)-naphthalene-1-sulfonyl chloride (76.96 g, 246 mmol) was added portionwise over 12 minutes to 90% nitric acid (154 mL, 3.278 mol) cooled in an ice-methanol bath (−20° C.). After the addition was complete, the reaction mixture was stirred at −20° C. for an additional 15 minutes. The reaction mixture was partitioned between ice water (800 mL) and chloroform (800 mL). The aqueous layer was extracted with chloroform (100 mL). The combined organic layers were washed with brine (400 mL, 200 mL), then dried over magnesium sulfate, filtered, and evaporated to a golden oil. Diethyl ether (300 mL) was added to the crude product and the mixture was shaken vigorously to afford an off-white solid. The solid was collected by filtration, washed with ether (2×50 mL), and dried under vacuum to afford 4-(2-acetoxy-ethyl)-8-nitro-naphthalene-1-sulfonyl chloride (41.85 g) as an off-white solid.

Step 5: 4-(2-Hydroxy-ethyl)-8-nitro-naphthalene-1-sulfonamide

Solid 4-(2-acetoxy-ethyl)-8-nitro-naphthalene-1-sulfonyl chloride (39.64 g, 111 mmol) was added to an ice-cold, 6.8 M solution of ammonia in methanol (408 mL, 277 mmol). The cooling bath was removed, the reaction flask was stoppered, and the reaction was stirred at room temperature. After 4 days, the dark amber solution was concentrated under vacuum to a dark gum. The residue was triturated vigorously shaken with water (300 mL) to give a solid which was washed with water (150 mL) then ether (150 mL) and dried under vacuum. The resulting brown solid was recrystallized from isopropanol (300 mL) to afford 4-(2-hydroxy-ethyl)-8-nitro-naphthalene-1-sulfonamide (27.79 g) as tan flakes.

Step 6: 4-(2-Hydroxy-ethyl)-1,8-naphthosultam

Powdered cesium carbonate (76.8 g, 236 mmol) was added to a solution of 4-(2-hydroxy-ethyl)-8-nitro-naphthalene-1-sulfonamide (30.77 g, 94.3 mmol) in anhydrous dimethylformamide (470 mL). The mixture was placed under a nitrogen atmosphere, sonicated for 10 minutes, then stirred at room temperature for 20 minutes. The mixture was then placed in a 100° C. oil bath and stirred vigorously. After 3.5 hours, the reaction mixture was removed from the heating bath, allowed to cool to room temperature, and left at room temperature overnight. The mixture was then filtered and the collected solid was washed with dimethylformamide. The combined filtrate and washings were evaporated to a dark oil. This material was dissolved in water (400 mL), treated with activated charcoal (5 g), and the resulting mixture was heated on a hot water bath for 5 minutes. The mixture was cooled slightly then filtered through a pad of super-cel. The filtrate was diluted with 2-butanone (450 mL), brine (300 mL), and 1M pH 1 aqueous phosphate (150 mL). The mixture was shaken vigorously and the layers were separated. The aqueous layer was extracted with 2-butanone (2×150 mL). The combined organic layers were washed with brine (2×300 mL), dried over magnesium sulfate, filtered and evaporated to a brown solid (21.4 g). The solid was treated with ethyl acetate (100 mL), sonicated for 15 minutes and filtered. The collected solid was washed with cold ethyl acetate (50 mL) and dried under vacuum to afford 4-(2-hydroxy-ethyl)-1,8-naphthosultam as a pale brown powder (16.68 g).

$^1$H NMR (DMSO-d$_6$, 500 MHz) δ3.25 (t, ArCH$_2$CH$_2$OH), 3.73 (m, ArCH$_2$CH$_2$OH), 4.77 (t, ArCH$_2$CH$_2$OH), 6.90 (d, H-7), 7.58 (dd, H-6), 7.69 (d, H-5), 7.69 (d, H-3), and 8.03 (d, H-2).

Step 7: 4-(2-Triethylsilanyloxy-ethyl)-1,8-naphthosultam

Chlorotriethylsilane (13.57 mL, 80.86 mmol) was added dropwise over 1 minute to a vigorously stirred suspension of 4-(2-hydroxy-ethyl)-1,8-naphthosultam (17.53 g, 70.32 mmol) and imidazole (5.99 g, 87.90 mmol) in dichloromethane (351 mL). The reaction mixture was stirred under a nitrogen atmosphere at room temperature for 15 minutes, then water (350 mL) was added. The organic layer was washed sequentially with 0.2 N HCl (350 mL) and water (350 mL) then dried over magnesium sulfate, filtered, and evaporated under vacuum to a dark oil (29.07 g). The crude product was purified by flash column chromatography on silica gel (5×27 cm column, eluted with 4:1 hexanes-EtOAc followed by 3:1 hexanes-EtOAc) to afford a deep red oil (23.9 g). The oil was mixed with hexanes (225 mL), sonicated to start crystallization, and stirred at room temperature. The mixture was filtered and the collected solid was washed with hexanes (3×15 mL) and vacuum dried to afford 4-(2-triethylsilyloxy-ethyl)-1,8-naphthosultam (19.78 g) as a light pink-white solid.

$^1$H NMR (CDCl$_3$, 500 MHz) δ0.54 (q, SiCH$_2$CH$_3$), 0.88 (t, SiCH$_2$CH$_3$), 3.34 (t, ArCH$_2$CH$_2$O), 3.95 (t, ArCH$_2$CH$_2$O), 6.89 (d, H-7), 7.14 (s, NH), 7.50 (dd, H-6), 7.62 (d, H-3), 7.66 (d, H-5), 7.89 (d, H-2)

mp 68.5–70.0° C.

PREPARATIVE EXAMPLE 2

SYNTHESIS OF ALLYL (1S,5R,6S)-6-[(1R)-(ALLYLOXYCARBONYLOXY)-ETHYL]-1-METHYL-2-{4-[2-(TRIFLUOROMETHANESULFONYLOXY)-ETHYL]-1,8-NAPHTHOSULTAMYL-METHYL}-CARBAPEN-2-EM-3-CARBOXYLATE

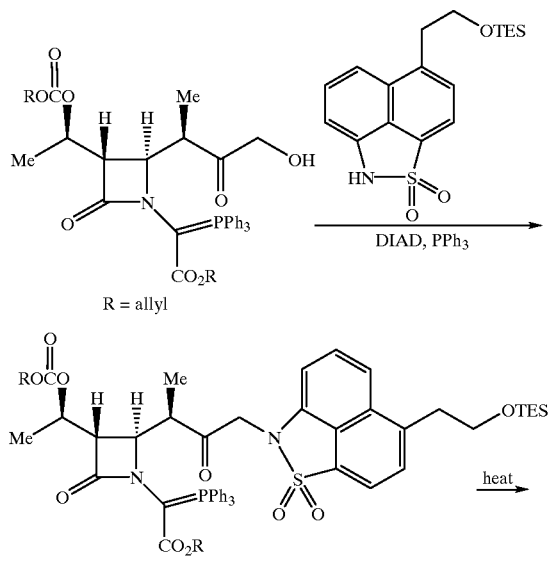

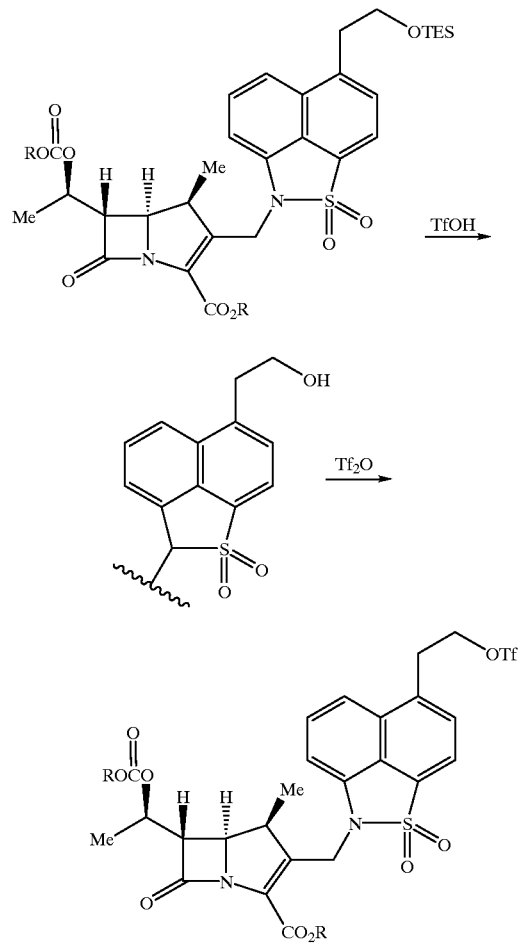

Step 1: Allyl {3-[1(R)-(allyloxycarbonyloxy)-ethyl]-2-{1(R)-methyl-2-oxo-3-[4-(2-triethylsilanyloxy-ethyl)-1,8-naphthosultamyl]-propyl}-(2R,3S)-4-oxo-azetidin-1-yl}-(triphenylphosplhoranylidene)-acetate A solution of allyl {3-[1(R)-(allyloxycarbonyloxy)-ethyl]-2-[3-hydroxy-1(R)-methyl-2-oxo-propyl]-(2R,3S)-4-oxo-azetidin-1-yl)-(triphenylphosphoranylidene)-acetate (74.8 g, 116.2 mmol), 4-(2-triethylsilanyloxy-ethyl)-1,8-naphthosultam (38.03 g, 104.6 mmol), and triphenylphosphine (45.72 g, 174.3 mmol) in anhydrous tetrahydrofuran (582 mL) was placed under a nitrogen atmosphere and cooled in an ice bath. Diisopropyl azodicarboxylate (34.3 mL, 174.3 mmol) was added over one minute. The resulting solution was sirred at 0° C. for 60 minutes followed by 30 minutes at room temperature. The mixture was filtered to remove a small amount of solid. The filtrate was diluted with ethyl acetate (300 mL) and washed with brine (300 mL). The organic phase was dried over magnesium sulfate, filtered and evaporated under vacuum to a dark red oil (220.1 g). The crude product was purified by chromatography on silica gel (5 kg), eluting with 7:3 hexane-ethyl acetate followed by 1:1 hexane-ethyl acetate. The product containing fractions were combined and evaporated under vacuum to afford the title compound (94.7 g) as a viscous oil. In order to determine an accurate yield for the reaction, an aliquot of this material (508.8 mg of 263.5 g of a solution of the product in toluene) was lyophilized from benzene to afford an off-white fluffy solid (144.1 mg). The actual yield of product was calculated as 74.62 g.

Step 2: Allyl (1S,5R,6S)-6-[(1R)-(allyloxccarbonyloxy)-ethyl]-1-methyl-2-[4-(2-triethylsilanyloxy-ethyl)-1,8-naphthosultamyl-methyl]-carbapen-2-em-3-carboxylate A solution of allyl {3-[1(R)-(allyloxycarbonyloxy)-ethyl]-2-{1(R)-methyl-2-oxo-3-[4-(2-triethylsilanyloxy-ethyl)-1,8-naphthosultamyl]-propyl}-(2R,3S)-4-oxo-azetidin-1-yl}-(triphenylphosphoranylidene)-acetate (74.6 g, 75.4 mmol, see step 1) in toluene (750 mL) was placed under a nitrogen atmosphere and refluxed for 2.5 hours. The reaction mixture was allowed to cool to room temperature and evaporated to a paste which was stored overnight in the freezer as a suspension in dichloromethane. The crude product was purified by chromatography on silica gel (1.8 kg), eluting with 85:15 hexane-ethyl acetate followed by 4:hexane-ethyl acetate. The product containing fractions were combined and evaporated under vacuum to afford the title compound (42.4 g) as a viscous tan oil.

IR (thin film on NaCl) 2955, 2876, 1784, 1746, 1716, 1258, and 661 cm$^{-1}$ $^1$H NMR (CDCl$_3$, 500 MHz) δ0.52 (q, SiC$\underline{H}_2$CH$_3$), 0.88 (t, SiCH$_2$C$\underline{H}_3$) 1.29 (d, 1-CH$_3$), 1.43 (d, C$\underline{H}_3$CHOCO$_2$), 3.34 (t, ArC$\underline{H}_2$CH$_2$O), 3.37 (dq, H-1), 3.43 (dd, H-6), 3.94 (t, ArCH$_2$C$\underline{H}_2$O), 4.14 (dd, H-5), 4.56–4.60 (m, OCO$_2$CH$_2$), 4.67 (d, 2-C$\underline{H}$aHb), 4.81 and 4.92 (two dd, CO$_2$CH$_2$), 5.11 (dq, CH$_3$C$\underline{H}$OCO$_2$), 5.24 (d, vinyl-H) 5.30–5.34 (m, 2 vinyl-H), 5.37 (d, 2-CHa$\underline{H}$b), 5.50 (d, vinyl-H), 5.86–5.89 (m, vinyl-H), 6.00–6.04 (m, vinyl-H), 6.69 (d, Ar H-7), 7.50 (t, Ar H-6), 7.61 (d, Ar H-5), 7.63 (d, Ar H-3), 7.90 (d, Ar H-2)

HRMS (FAB) calculated for C$_{36}$H$_{47}$N$_2$O$_9$SiS (MH$^+$) 711.2771; found 711.2690.

Step 3: Allyl (1S 5R,6S)-6-[(1R)-(allyloxycarbonyloxy)-ethyl]-2-[4-(2-hydroxy-propyl)-1,8-naphthosultamyl-methyl]-1-methyl-carbapen-2-em-3-carboxylate A solution of allyl (1S,5R,6S)-6-[(1R)-(allyloxycarbonyloxy)-ethyl]-1-methyl-2-[4-(2-triethylsilanyloxy-ethyl)-1,8-naphthosultamyl-methyl]-carbapen-2-em-3-carboxylate (45.2 g, 63.6 mmol) in tetrahydrofuran (500 mL) was diluted with water (125 mL) and treated with 1M aqueous trifluoromethanesulfonic acid (6.4 mL, 6.4 mmol). The resulting mixture was stirred at room temperature for 15 minutes, then partitioned between 5% aqueous sodium bicarbonate (200 mL), brine (25 mL), and ethyl acetate (500 mL). The organic phase was washed with dilute brine (200 mL), dried over magnesium sulfate, filtered and evaporated under vacuum to an oil (50.2 g). The oil was evaporated under vacuum from toluene (3×50 mL) to afford the title compound (42.9 g) as a tacky foam. This material was used without purification in the next step.

$^1$H NMR (CDCl$_3$) δ1.31 (d, 1-CH$_3$), 1.45 (d, C$\underline{H}_3$CHOCO$_2$), 3.41 (t, ArC$\underline{H}_2$CH$_2$OH), 3.41 (dq, H-1), 3.45 (dd, H-6), 4.04 (dt, ArCH$_2$C$\underline{H}_2$OH), 4.16 (dd, H-5), 4.59 (m, OCO$_2$CH$_2$), 4.69 (d, 2-C$\underline{H}$aHb), 4.89 (m, CO$_2$CH$_2$), 5.14 (dq, CH$_3$C$\underline{H}$OCO$_2$), 5.26, 5.33, 5.35 and 5.53 (four m, 4 vinyl-H), 5.41 (d, 2-CHa$\underline{H}$b), 5.91 and 6.05 (two m, 2 vinyl-H), 6.73 (d, Ar H-7), 7.54 (dd, Ar H-6), 7.63 (d, Ar H-5), 7.68 (d, Ar H-3), 7.95 (d, Ar H-2)

Step 4: Allyl (1S,5R,6S)-6-[(1R)-(allyloxycarbonyloxy)-ethyl]-1-methyl-2-{-4-[2-(trifluoromethanesulfonyloxy)-ethyl]-1,8-naphthosultamyl-methyl}-carbapen-2-em-3-carboxylate A solution of allyl (1S,5R,6S)-6-[(1R)-(allyloxycarbonyloxy)-ethyl]-2-[4-(2-hydroxy-propyl)-1,8-naphthosultamyl-methyl]-1-methyl-carbapen-2-em-3-carboxylate (63.58 mmol, amount teoretically present in the unpurified product of the previous step) in anhydrous methylene chloride (750 mL) was placed under a nitrogen atmosphere, cooled in an ice-methanol bath (–15° C.), and treated with 2,6-lutidine (22.2 mL, 190.7 mmol). The resulting mixture was aged at –15° C. for 8 minutes then trifluoromethanesulfonic anhydride (16.0 mL, 95.4 mmol) was added over a period of 4 minutes. After 30 minutes at –15° C., the reaction mixture was diluted with methylene chloride (1.25 L) and washed sequentially with water (1.8 L), 0.2N hydrochloric acid (2×1.8 L) and water (1.8 L), then dried over magnesium sulfate, filtered, and evaporated under vacuum to give the title compound as an oil.

$^1$H NMR (CDCl$_3$, 500 MHz) δ1.31 (d, 1-C$\underline{H}_3$), 1.44 (d, C$\underline{H}_3$CHOH), 3.39 (m, H-1), 3.45 (dd, H-5), 3.67 (C$\underline{H}_2$CH$_2$OTf), 4.16 (m, H-6), 4.58 (t, CH$_2$OTf), 4.67 (d, 2-CHaHb), 4.82 (m, C$\underline{H}_2$CH=CH$_2$), 4.93 (m, CH$_2$CH=C$\underline{H}_2$), 5.12 (m, C$\underline{H}$CH$_3$O), 5.24 (d, C$\underline{H}_2$CH=CH$_2$), 5.32 (m, CH$_2$CH=C$\underline{H}_2$), 5.41 (d, CH$_2$N), 5.52 (d, C$\underline{H}_2$CH=CH$_2$), 5.88 (m, CH$_2$C$\underline{H}$=CH$_2$), 6.03 (m, CH$_2$C$\underline{H}$=CH$_2$), 6.77 (d, ArH-7), 7.54 and 7.58 (2 m's, ArH-5 and Ar H-6), 7.67 (d, Ar H-2), 7.96 (d, Ar H-4).

PREPARATIVE EXAMPLE 3

SYNTHESIS OF 3-(2-TRIETHYLSILANYLOXY-ETHYL)-1,8-NAPHTHOSULTAM

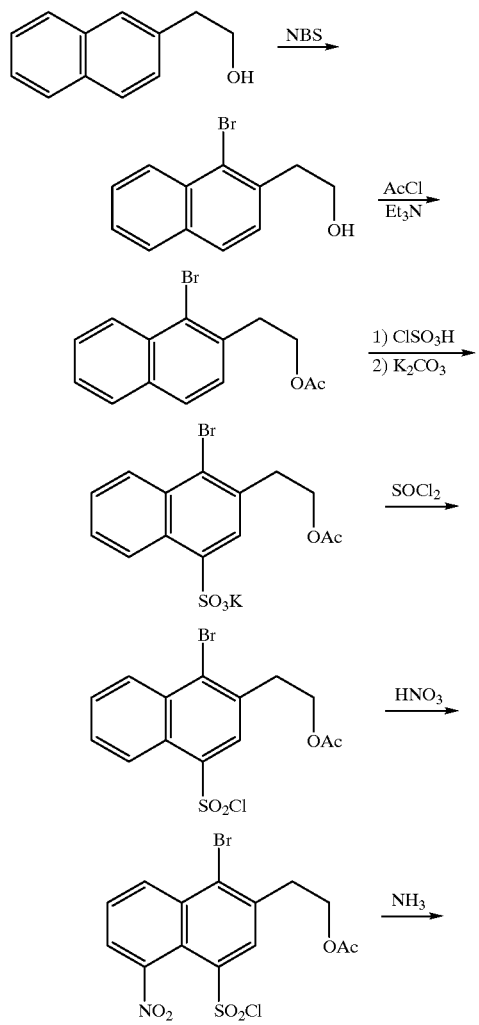

-continued

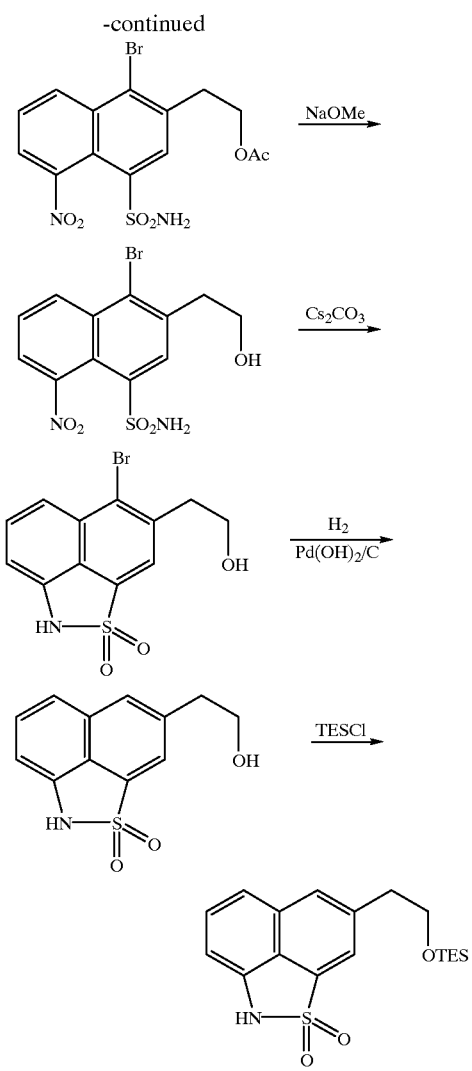

Step 1: 1-Bromo-2-(2-hydroxy-ethyl)-naphthalene

A solution of 2-(2-hydroxy-ethyl)-naphthalene (58.5 g, 0.34 mol) in anhydrous acetonitrile (500 mL) was treated with N-bromo-succinimide (66.5 g, 0.37 mol). The resulting solution was stirred at room temperature under a nitrogen atmosphere and protected from light for 30 minutes, then heated in an oil bath at 50° C. for 2 hours. After cooling to room temperature, the reaction mixture was evaporated under vacuum to a viscous oil. The oil in diethyl ether (350 mL) was washed with water (350 mL), dilute aqueous sodium thiosulfate (300 mL), water (300 mL) and brine (200 mL), dried over magnesium sulfate, filtered, and evaporated under vacuum to an oil (89.5 g) that solidified on standing. The crude product was chromatographed on a column of EM silica gel 60, eluting with methylene chloride, to afford a yellow solid (78.2 g). Recrystallization of this material from carbon tetrachloride provided the title compound (46.5 g) as a pale yellow solid.

Step 2: 2-(2-Acetoxy-ethyl)-1-bromo-naphthalene

A solution of 1-bromo-2-(2-hydroxy-ethyl)-naphthalene (46.5 g, 0.185 mol) in methylene chloride (370 mL) was placed under a nitrogen atmosphere, cooled in an ice bath, and stirred. Triethylamine (32.3 mL, 0.232 mol) was added followed by acetyl chloride (15.8 mL, 0.222 mol) dropwise over 5 minutes. The reaction mixture was removed from the ice bath and stirred at room temperature for 15 minutes. The reaction mixture was washed with water (300 mL), 1N hydrochloric acid (200 mL) and water (250 mL), dried over magnesium sulfate, filtered, and evaporated under vacuum to afford the title compound as an oil (55.1 g).

Step 3: Potassium 3-(2-acetoxy-ethyl)-4-bromo-naphthalene-1-sulfonate

A solution of 2-(2-acetoxy-ethyl)-1-bromo-naphthalene (32.5 g, 0.111 mol) in trifluoroacetic acid (111 mL) was stirred under a nitrogen atmosphere and cooled in an ice bath while chlorosulfonic acid (8.9 mL, 0.130 mol) was added dropwise over 5 minutes. The resulting solution was heated in an oil bath at 50° C. for 90 minutes then cooled to room temperature and evaporated under vacuum to dark oil. The oil was partitioned between methylene chloride (150 mL) and water (150 mL). The aqueous phase was washed with methylene chloride (150 mL), briefly pumped under vacuum, then brought to pH 8 with 3M aqueous potassium hydroxide (30 mL) followed by 4M aqueous potassium carbonate (35 mL). The resulting mixture was stirred in a cold room (5° C.) for 2 hours and filtered to remove the product. The recovered white solid was vacuum dried to afford the title compound (11.21 g).

Step 4: 3-(2-Acetoxy-ethyl)-4-bromo-naphthalene-1-sulfonyl chloride

Potassium 3-(2-acetoxy-ethyl)-4-bromo-naphthalene-1-sulfonate (17.75 g, 43.2 mmol) was added at room temperature to a stirred solution of N,N-dimethylformamide (0.334 mL, 4.31 mmol) in thionyl chloride (63 mL, 863 mmol). The resulting mixture was placed in an oil bath at 70° C. and stirred. After 10 minutes, additional thionyl chloride (20 mL) was added to facilitate stirring. After 40 minutes at 70°, the reaction flask was fitted with a distillation head and excess thionyl chloride was removed under vacuum. The residual brown solid was mixed with diethyl ether (300 mL) and added to an ice-cold, stirred mixture of water (100 mL) and ether (100 mL). The organic phase was separated, washed with water (200 mL) and brine (100 mL), dried over magnesium sulfate, filtered, and evaporated under vacuum to afford the title compound (14.63 g).

Step 5: 3-(2-Acetoxy-ethyl)-4-bromo-8-nitro-naphthalene-1-sulfonyl chloride

An ice-cold, stirred solution of 3-(2-acetoxy-ethyl)-4-bromo-naphthalene-1-sulfonyl chloride (17.66 g, 45.1 mmol) in trifluoroacetic acid (150 mL) was treated with 96% sulfuric acid (12.5 mL, 225 mmol) and with 90% nitric acid (2.65 mL, 56.4 mmol) added dropwise over 3 minutes. The reaction mixture was removed from the ice bath, stirred at room temperature for 15 minutes, re-cooled in an ice bath, and treated with water (850 mL) added dropwise. The resulting mixture was filtered through a celite pad to collect the solid which was washed with water (100 mL) and dissolved in methylene chloride (350 mL). The methylene chloride solution was washed with water (500 mL) containing brine (100 mL), dried over magnesium sulfate, and evaporated under vacuum to an oil (21.23 g). This material was shown to be a 42:58 mixture of the 5-$NO_2$ to 8-$NO_2$ products by $^1$H NMR). The crude product was mixed with ethyl acetate (20 mL) and sonicated to provide a crystalline precipitate. This material was collected, washed with ethyl acetate, and dried under vacuum to afford the title compound (8.11 g) as an off-white solid. The mother liquors yielded an additional 1.47 g of the title compound following flash chromatography on silica gel (eluting with 30–35% ethyl acetate in hexane) and crystallization from diethyl ether.

Step 6: 3-(2-Acetoxy-ethyl)-4-bromo-8-nitro-naphthalene-1-sulfonamide

Solid 3-(2-acetoxy-ethyl)-4-bromo-8-nitro-naphthalene-1-sulfonyl chloride (5.00 g, 11.45 mmol) was added at room temperature to 0.5M ammonia in dioxane (92 mL, 46 mmol). After stirring at room temperature for 40 minutes, the mixture was evaporated under vacuum to a residue which was mixed with water (100 mL), sonicated, and filtered. The collected pale-yellow solid was washed with water (2×20 mL) and vacuum dried to afford the title compound (4.75 g).

Step 7: 4-Bromo-3-(2-hydroxy-ethyl)-8-nitro-naphthalene-1-sulfonamide

Sodium methoxide in methanol (23.7 mL of a 0.5M solution, 11.8 mmol) was added to a suspension of 3-(2-acetoxy-ethyl)-4-bromo-8-nitro-naphthalene-1-sulfonamide (4.70 g, 11.3 mmol) in methanol (33 mL). The mixture was stirred under a nitrogen atmosphere at room temperature for 90 minutes, then concentrated under vacuum to approximately half volume, diluted with ethyl acetate (200 mL), and washed with 2N hydrochloric acid. The oganic solution was washed with water (100 mL) and brine (50 mL), dried over magnesium sulfate, filtered, and left to stand at room temperature. The organic solution deposited a solid which was collected by filtration, washed with ethyl acetate (2×15 mL), and vacuum dried to give the title comound (1.78 g). Additional poduct (1.88g) was obtained from the mother liquors after concentration under vacuum and crystallization from diethyl ether.

Step 8: 4-Bromo-3-(2-hydroxy-ethyl)-1,8-naphthosultam

A solution of 4-bromo-3-(2-hydroxy-ethyl)-8-nitro-naphthalene-1-sulfonamide (3.61 g, 9.62 mmol) in anhydrous N,N-dimethylformamide (96 mL) was treated with cesium carbonate (7.84 g, 24.1 mmol). The resulting mixture placed under a nitrogen atmospere, sonicated at room temperature for 10 minutes, stirred at room temperature for 5 minutes, and then heated in an oil bath at 100° C. for 2 hours. The mixture was evaporated under vacuum to a brown residue which was partitioned between ethyl acetate (100 mL) and 2N hydrocloric acid (20 mL). The organic phase was washed with water (20 mL) and brine (20 mL), dried over magnesium sulfate, filtered, and evaporated under vacuum to a solid (2.83 g). This material was mixed with diethyl ether (30 mL), sonicated, stirred, and filtered. The collected solid was washed with ether (20 mL) and vacuum dried to give the title compound (2.21 g) as a tan powder.

Step 9: 3-(2-Hydroxy-ethyl)-1,8-naphthosultam

A solution of 4-bromo-3-(2-hydroxy-ethyl)-1,8-naphthosultam (2.10 g, 6.4 mmol) in ethanol (105 mL) was treated with triethylamine (2.68 mL, 19.2 mmol) and 20% palladium hydroxide on carbon (0.84 g). The mixture was hydrogenated (45–50 psi $H_2$) on a Parr shaker for 6.5 hours at room temperature, then filtered through a celite pad to remove the catalyst which was washed with additional ethanol (3×5 mL). The filtrate and washings were evaporated under vacuum to a residue which was partitioned between ethyl acetate (60 mL) and 1N hydrochloric acid (50 mL). The organic phase was washed with brine (25 mL), dried over magnesium sulfate, filtered, and evaporated under vacuum to afford the title compound (1.32 g) as a brown solid.

Step 10: 3-(2-Triethylsilanyloxy-ethyl)-1,8-naphthosultam

A mixture of 3-(2-hydroxy-ethyl)-1,8-naphthosultam (1.44 g, 5.78 mmol) and imdazole (0.495 g, 7.27 mmol) in anhydrous methylene chloride (39 mL), at room temperature and under a nitrogen atmosphere, was treated with chlorotriethylsilane (1.12 mL, 6.69 mmol). After stirring at room temperature for 30 minutes, the mixture was diluted with methylene chloride (60 mL), washed with water (100 mL), 0.2N hydrochloric acid (50 mL) and water (100 mL), dried over magnesium sulfate, filtered, and evaporated under vacuum to a dark oil (2.15 g). The oil was purified by flash chromatography on EM silica gel 60 (4×15 cm column), using 3:1 hexane-ethyl acetate as eluting solvent, to give an oil (2.09 g). This material was mixed with hexane (10 mL) and sonicated to afford a crystalline solid. The solid was collected, washed with hexane (3 mL), and dried to afford the title compound (1.73 g).

MP. 97.5–98.0° C.

$^1$NMR (CDCl$_3$) δ0.54 (q, SiCH$_2$CH$_3$), 0.88 (t, SiCH$_2$CH$_3$), 3.08 (t, ArCH$_2$), 3.90 (t, CH$_2$O), 6.84 (m, H-7), 7.24–7.47 (m, H-5 and H-6), 7.84 and 7.90 (two d's, H-2 and H-4).

PREPARATIVE EXAMPLE 4

SYNTHESIS OF ALLYL (1S,5R,6S)-6-[(1R)-(ALLYLOXYCARBONYLOXY)-ETHYL]-1-METHYL-2-{3-[2-(TRIFLUOROMETHANESULFONYLOXY)-ETHYL]-1,8-NAPHTHOSULTAMYL-METHYL}-CARBAPEN-2-EM-3-CARBOXYLATE

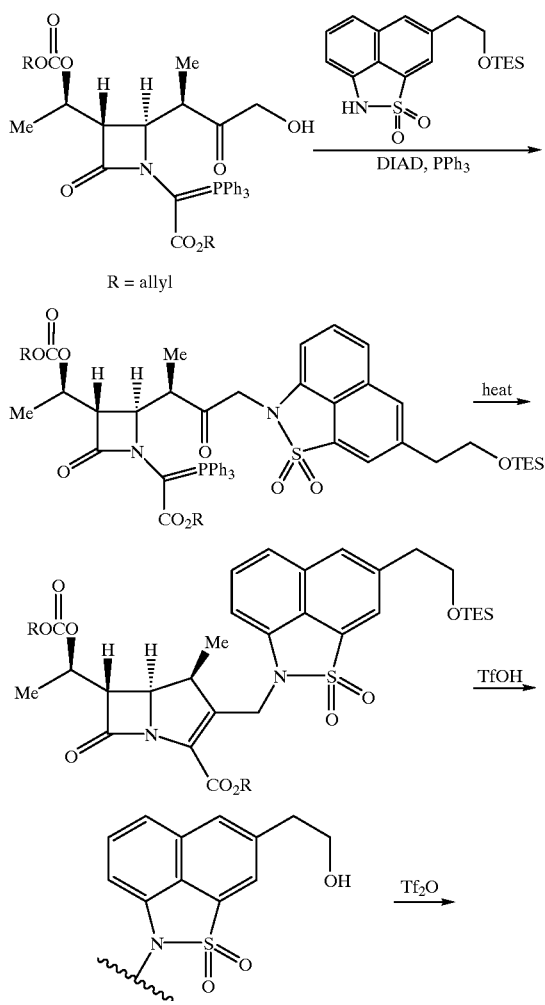

-continued

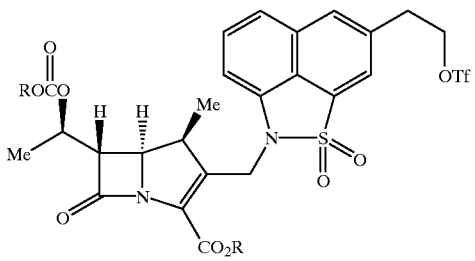

Step 1: Allyl {3-[1(R)-(allyloxycarbonyloxy)-ethyl]-2-{1 (R)-methyl-2-oxo-3-[3-(2-triethylsilanyloxy-ethyl)-1,8-naphthosultamyl]-propyl}-(2R,3S)-4-oxo-azetidin-1-yl}-(triphenylphosphoranylidene)-acetate A solution of allyl {3-[1(R)-(allyloxycarbonyloxy)-ethyl]-2-[3-hydroxy-1(R)-methyl-2-oxo-propyl]-(2R,3S)-4-oxo-azetidin-1-yl}-(triphenylphosphoranylidene)-acetate (3.81 g, 5.91 mmol), 3-(2-triethylsilanyloxy-ethyl)-1,8-naphthosultam (1.72 g, 4.73 mmol), and triphenylphosphine (2.32 g, 8.87 mmol) in anhydrous tetrahydrofuran (30 mL) was placed under a nitrogen atmosphere and cooled in an ice bath. Diisopropyl azodicarboxylate (1.75 mL, 8.87 mmol) was added over one minute. The resulting solution was sirred at 0° C. for 60 minutes followed by 30 minutes at room temperature, then diluted with ethyl acetate (100 mL) and washed with brine (50 mL). The organic phase was dried over magnesium sulfate, filtered and evaporated under vacuum to a viscous, dark oil. The crude product was purified by flash chromatography on EM silica gel 60 (5×19 cm column), eluting with 2:1 hexane-ethyl acetate. The product containing fractions were combined and evaporated under vacuum to afford the title compound (3.48 g) as a foam.

Step 2: Allyl (1S,5R,6S)-6-[(1R)-(allyloxycarbonyloxy)-ethyl]-1-methyl-2-[3-(2-triethylsilanyloxy-ethyl)-1,8-naphthosultamyl-methyl]-carbapen-2-em-3-carboxylate A solution of allyl {3-[1(R)-(allyloxycarbonyloxy)-ethyl]-2-{1(R)-methyl-2-oxo-3-[3-(2-triethylsilanyloxy-ethyl)-1,8-naphthosultamyl]-propyl}-(2R,3S)-4-oxo-azetidin-1-yl}-(triphenylphosphoranylidene)-acetate (3.47 g, 3.50 mmol) in anhydrous toluene (35 mL) was placed under a nitrogen atmoshere and heated at reflux for 3.5 hours. The solution was concentrated under vacuum to 10 mL and applied to a column (4×20 cm) of EM silica gel 60. The column was eluted with 3:1 hexane-ethyl acetate (28× 20 mL fractions) followed by 2:1 hexane-ethyl acetate (20 mL fractions). The product containing fractions were combined and concentrated under vacuum. The residue was lyophilized from benzene to give the title compound (1.894 g) as a gum.

$^1$H NMR (CDCl$_3$) δ0.57 (q, SiC$\underline{H}_2$CH$_3$), 0.92 (t, SiCH$_2$C$\underline{H}_3$), 1.31 (d, 1-CH$_3$), 1.45 (d, C$\underline{H}_3$CHOCO$_2$), 3.11 (t, ArC$\underline{H}_2$CH$_2$O), 3.41 (dq, H-1), 3.45 (dd, H-6), 3.93 (t ArCH$_2$C$\underline{H}_2$O), 4.17 (dd, H-5), 4.59 (m, OCO$_2$CH$_2$), 4.67 (d, 2-C$\underline{H}$aHb), 4.81–4.95 (m, CO$_2$CH$_2$), 5.14 (dq, CH$_3$C$\underline{H}$OCO$_2$), 5.25–5.36 (m, 3 vinyl-H), 5.39 (d, 2-CHa$\underline{Hb}$), 5.50–5.54 (m, vinyl-H), 5.88–5.93 (m, vinyl-H), 6.01–6.07 (m, vinyl-H), 6.66 (d, Ar H-7), 7.43 (d, Ar H-5), 7.48 (dd, Ar H-6), 7.90 and 7.93 (two s, Ar H-2 and Ar H-4).

Step 3: Allyl (1S,5R,6S)-6-[(1R)-(allyloxycarbonyloxy)-ethyl]-2-[3-(2-hydroxy-propyl)-1,8-naphthosultamyl-methyl]-1-methyl-carbapen-2-em-3-carboxylate A solution of allyl (1S,5R,6S)-6-[(1R)-(allyloxycarbonyloxy)-ethyl]-1-methyl-2-[3-(2-triethylsilanyloxy-ethyl)-1,8-naphthosultamyl-methyl]-carbapen-2-em-3-carboxylate (0.502 g, 0.706 mmol) in tetrahydrofuran (5.6 mL) was diluted with water (1.4 mL) and treated with 1M aqueous trifluoromethanesulfonic acid (0.071 mL, 0.071 mmol). After stirring at room temperature for 15 minutes, the solution was treated with 2% aqueous sodium bicarbonate (5 mL) and extracted with ethyl acetate (25 mL). The organic phase was washed with brine (25 mL), dried over magnesium sulfate, filtered and evaporated under vacuum to provide the title compound (0.473 g) as an oil.

1H NMR (CDCl$_3$) δ1.31 (d, 1-CH$_3$), 1.45 (d, C$\underline{H}_3$CHOCO$_2$), 3.16 (t, ArC$\underline{H}_2$CH$_2$OH), 3.40 (dq, H-1), 3.45 (dd, H-6), 4.01 (q, ArCH$_2$C$\underline{H}_2$OH), 4.16 (dd, H-5), 4.59 (m, OCO$_2$CH$_2$), 4.67 (d, 2-C$\underline{H}$aHb), 4.81–4.95 (m, CO$_2$CH$_2$), 5.13 (dq, CH$_3$C$\underline{H}$OCO$_2$), 5.25–5.36 (m, 3 vinyl-H), 5.40 (d, 2-CHa$\underline{Hb}$), 5.50–5.54 (m, vinyl-H), 5.88–5.93 (m, vinyl-H), 6.02–6.07 (m, vinyl-H), 6.68 (d, Ar H-7), 7.45 (d, Ar H-5), 7.50 (dd, Ar H-6), 7.91 and 7.96 (two s's, Ar H-2 and Ar H-4).

Step 4: Allyl (1S,5R,6S)-6-[(1R)-(allyloxycarbonyloxy)-ethyl]-1-methyl-2-[3-[2-(trifluoromethanesulfonyloxy)-ethyl]-1,8-naphthosultamyl-methyl]-carbapen-2-em-3-carboxylate A solution of allyl (1S,5R,6S)-6-[(1R)-(allyloxycarbonyloxy)-ethyl]-2-[3-(2-hydroxy-propyl)-1,8-naphthosultamyl-methyl]-1-methyl-carbapen-2-em-3-carboxylate (0.706 mmol) and 2,6-lutidine (0.246 mL, 2.12 mmol) in anhydrous methylene chloride (9.4 mL) was placed under a nitrogen atmosphere and cooled in a CCl$_4$-dry ice bath (−23° C.).

Trifluoromethanesulfonic anhydride (0.178 mL, 1.06 mmol) was added and the resulting solution was stirred in the cold for 30 minutes. The solution was diluted with methylene chloride (20 mL) and water (20 mL) and shaken. The organic phase was separated, washed with 0.2N hydrochloric acid (20 mL) and water (20 mL), dried over magnesium sulfate, filtered and evaporated under vacuum to give the title compound as a foam (0.531 g).

$^1$H NMR (CDCl$_3$) δ1.32 (d, 1-CH$_3$), 1.46 (d, C$\underline{H}_3$CHOCO$_2$), 3.41 (dq, H-1), 3.44 (t, ArC$\underline{H}_2$CH$_2$O), 3.45 (dd, H-6), 4.18 (dd, H-5), 4.56–4.64 (m, OCO$_2$CH$_2$), 4.63 (d, 2-C$\underline{H}$aHb), 4.83 (t, ArCH$_2$C$\underline{H}_2$O), 4.8–4.96 (m, CO$_2$CH$_2$), 5.14 (dq, CH$_3$C$\underline{H}$OCO$_2$), 5.25–5.36 (m, 3 vinyl-H), 5.42 (d, 2-CHa$\underline{Hb}$), 5.51–5.54 (m, vinyl-H), 5.86–5.95 (m, vinyl-H), 6.02–6.09 (m, vinyl-H), 6.73 (d, Ar H-7), 7.48 (d, Ar H-5), 7.55 (dd, Ar H-6), 7.86 and 7.97 (two s's, Ar H-2 and Ar H-4).

PREPARATIVE EXAMPLE 5

SYNTHESIS OF 4-(TRIETHYLSILYLOXY-METHYL)-1,8-NAPHTHOSULTAM

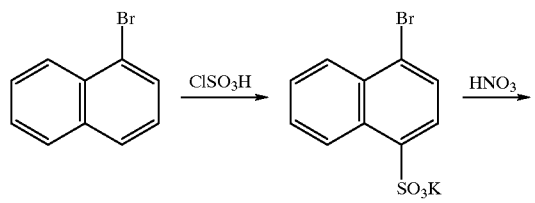

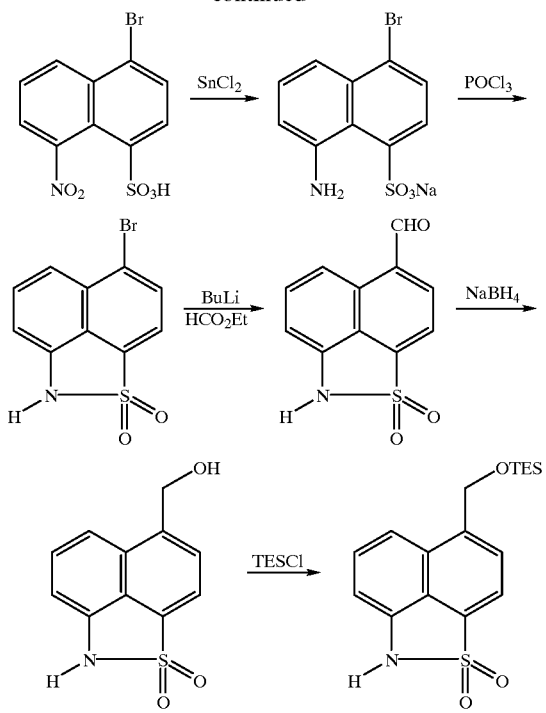

Step 1: Potassium 4-bromo-naphthalene-1-sulfonate

A solution of 1-bromonaphthalene (19 mL, 137 mmol) in carbon tetrachloride (24 mL) was cooled in an ice bath under nitrogen. Chlorosulfonic acid (9.1 mL, 137 mmol) was added dropwise over 20 minutes. After an additional 5 minutes, the heavy grey suspension was removed from the ice bath and was stirred at room temperature for 16 hours to give a grey paste. The mixture was partitioned between methylene chloride (100 mL) and water (300 mL). The aqueous layer was made basic with potassium carbonate and the resulting suspension was filtered. The collected solid was washed with methylene chloride (50 mL) and water (50 mL), and dried under vacuum to give the title compound as a white solid (30 g).

$^1$H NMR (DMSO-d$_6$) δ7.61 (m, ArH), 7.65 (m, ArH), 7.82 (m, 2ArH), 8.14 (dd, ArH), and 8.90 (dd, ArH).

Step 2: 4-Bromo-8-nitro-naphthalene-1-sulfonic acid

Potassium 4-bromo-naphthalene-1-sulfonate (1.38 g, 4.24 mmol) was added portionwise over 20 minutes to 90% nitric acid (2 mL), which was cooled in a methanol/ice bath to approximately −15° C. After 1.5 hours, the mixture was placed in a refrigerator for 20 hours. Diethyl ether (20 mL) was added and the precipitated solid was filtered, washed with ether (100 mL) and isopropanol (20 mL), and dried under a stream of nitrogen to give the title compound as an approximately 4:1 mixture of the 5- and 8-nitro isomers (1.25 g).

$^1$H NMR (D$_2$O) δ7.70 (dd, ArH), 8.09 (d, ArH), 8.20 (d, ArH), 8.21 (dd, ArH), and 8.63 (d, ArH).

Step 3: Sodium 4-bromo-8-amino-naphthalene-1-sulfonate

4-Bromo-8-nitro-naphthalene-1-sulfonic acid (1 g, 3.01 mmol) and tin chloride dihydrate (1.83 g, 8.1 mmol) were suspended in a mixture of water (10 mL) and ethanol (10 mL). The resulting mixture was heated for 3 hours in a 100° C. oil bath. The mixture was cooled to room temperature and filtered. The collected solid was suspended in water (20 mL) and the mixture was made basic with sodium carbonate then placed on a CG-161 amberchrom resin column (3×9 cm). The column was washed with water (300 mL) and was eluted with 25% MeCN/H$_2$O, collecting 12 mL fractions. Fractions 17–19 were combined and evaporated to give the title compound as a solid (0.33 g).

$^1$H NMR (D$_2$O) δ7.07 (dd, ArH), 7.49 (t, ArH), 7.83 (d, ArH), 7.85 (dd ArH) and 8.08 (d, ArH).

Step 4: 4-Bromo-1,8-naphthosultam

Sodium 4-bromo-8-amino-naphthalene-1-sulfonate (1.2 g, 3.70 mmol) was suspended in phosphorous oxychloride (10 mL, 107 mmol) and the mixture was refluxed for 1 hour to give a thin suspension. The mixture was cooled to room temperature and was added to ice (100 mL). The precipitate was collected and washed with water (20 mL) then dried under vacuum (0.675 g). A second crop was obtained from the filtrate (0.186 g). The combined solids were dissolved in 5% methanol in methylene chloride and were placed on a silica gel column (29×3.5cm, packed and eluted with 5% methanol in methylene chloride), collecting 8 mL fractions. Fractions 27–39 were combined and evaporated to give the title compound as a solid (0.55 g).

$^1$H NMR (0.14 mL CDCl$_3$ and 0.01 mL CD$_3$OD) δ6.89 (d, ArH), 7.58 (dd ArH), 7.68 (d, ArH), 7.73 (d, ArH) and 7.95 (d, ArH).

Step 5: 4-Formyl-1,8-naphthosultam

A solution of 4-bromo-1,8-naphthosultam (0.24 g, 0.845 mmol) in anhydrous tetrahydrofuran (5 mL) was cooled in a dry ice/acetone bath under nitrogen. n-Butyllithium (1.32 mL of a 1.6 M solution in hexanes, 2.11 mmol) was added and the mixture was stirred for 5 minutes. Ethyl formate (1 mL, 12.4 mmol) was then added, and after an additional 5 minutes, 2N aqueous hydrochloric acid (3 mL) was added. The flask was removed from the bath and the yellow solution was partitioned between ethyl acetate (30 mL) and water (30 mL). The ethyl acetate layer was washed with saturated aqueous sodium chloride (20 mL), dried over magnesium sulfate, filtered, and evaporated. The residual oil was purified on preparative silica gel plates (3×1000 micron/ developed and eluted with 5% methanol/methylene chloride) to give the title compound as a red solid (0.035 g).

$^1$H NMR (CDCl$_3$) δ7.09 (d, ArH), 7.78 (dd, ArH), 8.12 (d, ArH), 8.30(d, ArH), 8.70 (d, ArH) and 10.5 (s, CHO).

Step 6: 4-Hydroxymethyl-1,8-naphthosultam

A solution of 4-formyl-1,8-naphthosultam (0.035 g, 0.15 mmol) in anhydrous methanol (1 mL) was cooled in an ice bath under nitrogen. Sodium borohydride (0.011 g, 0.3 mmol) was added and the solution was stirred for 30 minutes. The mixture was partitioned between methylene chloride (10 mL) and 0.2N aqueous hydrochloric acid (10 mL). The aqueous layer was extracted with 5% methanol in methylene chloride (2×10 mL), and the combined organic layers were evaporated to give the title compound as a yellow solid (0.032 g).

$^1$H NMR (0.14mLCDCl$_3$ and 0.01 mL CD$_3$OD) δ5.13 (s, CH$_2$OH), 6.85 (d, ArH), 7.50 (dd, ArH), 7.57 (d, ArH), 7.82 (d, ArH) and 7.88 (d, ArH).

Step 7: 4-(Triethylsilyloxy-methyl)-1,8-naphthosultam

A mixture of 4-hydroxymethyl-1,8-naphthosultam (2.92 g, 8.7 mmol), imidazole (0.74 g, 10.9 mmol), and triethylsilyl chloride (1.68 mL, 10.0 mmol) in dichloromethane (40 mL) was stirred at room temperature under a nitrogen atmosphere for 30 minutes. The reaction mixture was then washed with 0.1 N HCl (80 mL), water (40 mL), and brine (40 mL), then dried over MgSO$_4$ and concentrated to a brown oil. The oil was stored at 0° C. for 72 hours. The crude product was purified by flash chromatography on EM silica gel 60 (5×15 cm) eluting with 4:1 hexane-ethyl acetate (200 mL) followed by 2:1 hexane-ethyl acetate (1000 mL). The product-containing fractions were combined and concentrated to give a light brown solid (2.3 g). The product was further purified by recrystallization from 15:1 hexane-ethyl acetate (80 mL) to give the title compound (1.48 g) as large white needles. The mother liquor was concentrated and washed with cold hexane (10 mL) to provide additional title compound (0.50 g) as smaller white needles.

$^1$H NMR (CDCl$_3$) δ0.73 (q, SiCH$_2$CH$_3$), 1.03 (t, SiCH$_2$CH$_3$), 5.26 (s, ArCH$_2$), 6.92 (d, ArH-7), 7.53 (dd, ArH-6), 7.59 (d, ArH-5), 7.93 and 7.96 (two d's, ArH-2 and ArH-3)

PREPARATIVE EXAMPLE 6

SYNTHESIS OF ALLYL (1S,5R,6S)-6-[(1R)-(ALLYLOXYCARBONYLOXY)-ETHYL]-1-METHYL-2-[4-(IODOMETHYL)-1,8-NAPHTHOSULTAMYL-METHYL]-CARBAPEN-EM-3-CARBOXYLATE

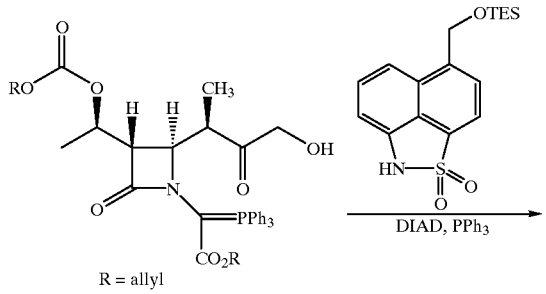

R = allyl

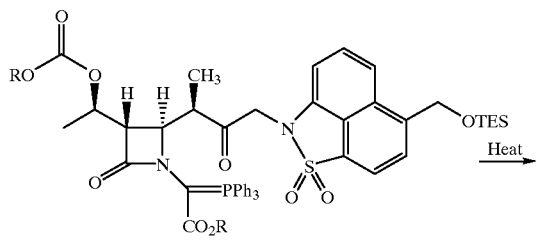

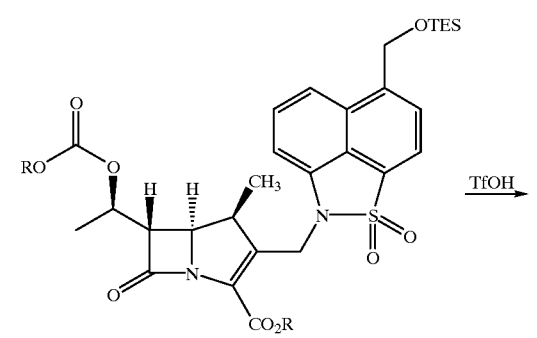

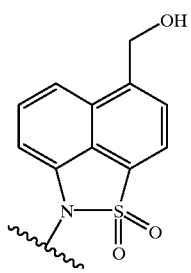

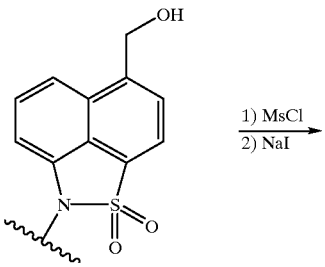

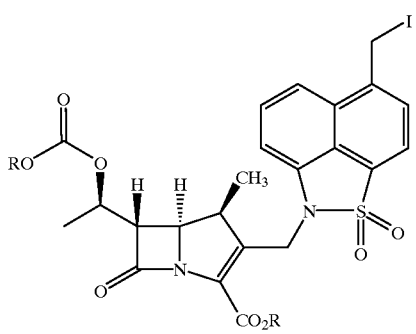

Step 1: Allyl {3-[1(R)-(allyloxycarbonyloxy)-ethyl]-2-[1(R)-methyl-2-oxo-3-[4-(2-triethylsilanyloxy-methyl)-1,8-naphthosultamyl]-propyl}-(2R,3S)-4-oxo-azetidin-1-yl}-(tripthenylphosphoranylidene)-acetate A solution of allyl {3-[1(R)-(allyloxycarbonyloxy)-ethyl]-2-[3-hydroxy-1(R)-methyl-2-oxo-propyl]-(2R,3S)-4-oxo-azetidin-1-yl}-(triphenylphosphoranylidene)-acetate (2.76 g, 4.3 mmol), 4-(2-triethylsilanyloxy-methyl)-1,8-naphthosultam (1.38 g, 3.9 mmol), and triphenyiphosphine (1.53 g, 5.9 mmol) in anhydrous THF (20 mL) was placed under a nitrogen atmosphere and cooled in an ice bath. Diisopropyl azodicarboxylate (1.2 mL, 5.9 mmol) was added over one minute. The resulting orange solution was stirred at 0° C. for 30 minutes and then an additional 30 minutes at room temperature, after which the reaction mixture wad partitioned between ethyl acetate (80 mL) and brine (80 mL). The organic phase then dried over MgSO$_4$ and concentrated. The concentrated solution was stored at 0° C. for 17 hours. The crude product was purified by flash chromatography on EM silica gel 60 (5×15 cm), eluting with 7:3 hexane-ethyl acetate (200 mL) followed by 1:1 hexane-ethyl acetate (1000 mL). The product-containing fractions were combined and concentrated to yield the title compound (3.2 g) as an off-white foam.

Step 2: Allyl (1S,5R,6S)-6-[(1R)-(allyloxycarbonyloxy)-ethyl]-1-methyl-2-[4-(2-triethylsilanyloxy-methyl)-1,8-naphthosultamyl-methyl]-carbapen-2-em-3-carboxylate A solution of allyl {3-[1(R)-(allyloxycarbonyloxy)-ethyl]-2-{1(R)-methyl-2-oxo-3-[4-(2-triethylsilanyloxy-methyl)-1,8-naphthosultamyl]-propyl}-(2R,3S)-4-oxo-azetidin-1-yl}-(triphenylphosphoranylidene)-acetate (3.2 g, 3.3 mmol) in anhydrous toluene (40 mL) was placed under a nitrogen atmoshere and heated at reflux for 2.75 hours. The reaction mixture was allowed to cool to −40° C. and then concentrated to an orange oil. The oil was dissolved in dichloromethane (3 mL) and then stored at 0° C. for 17 hours. The crude product was purified by flash chromatography on EM silica gel 60 (5×15 cm) eluting with 4:1 hexane-ethyl acetate (400 mL) followed by 2:1 hexane-ethyl acetate (850 mL). The product-containing fractions were concentrated to give the title compound (1.6 g) as an off-white foam.

¹H NMR (CDCl₃) δ0.73 (q, SiC$\underline{H}_2$CH₃), 1.02 (t, SiCH₂CO$\underline{H}_3$), 1.31 (d, 1-CH₃), 1.45 (d, C$\underline{H}_3$CHO), 3.40 (dq, H-1), 3.44 (dd, H-6), 4.16 (dd, H-5), 4.59 (m, OCO₂CH₂), 4.67 (d, 2-C$\underline{H}$aHb), 4.88 (m, CO₂CH₂), 5.13 (dq, CH₃C$\underline{H}$O), 5.26 (m, ArCH₂O and 1 vinyl-H), 5.32–5.36 (m, 2 vinyl-H's), 5.40 (d, CHa$\underline{H}$b), 5.50–5.54 (m, vinyl-H), 5.86–5.96 (m, vinyl-H), 6.00–6.10 (m, vinyl-H), 6.72 (dd, Ar H-7), 7.52 (m, Ar H5 and Ar H6), 7.94 and 7.98 (two d's, Ar H2 and Ar H3)

Step 3: Allyl (1S,5R,6S)-6-[(1R)-(allyloxycarbonyloxy)-ethyl]-2-4-(hydroxymethyl)-1,8-naphthosultamyl-methyl]-1-methyl-carbapen-2-em-3-carboxylate A solution of allyl (1S,5R,6S)-6-[(1R)-(allyloxycarbonyloxy)-ethyl]-1-methyl-2-[4-(2-triethylsilanyloxy-methyl)-1,8-naphthosultamyl-methyl]-carbapen-2-em-3-carboxylate (1.50 g, 2.15 mmol) in tetrahydrofuran (32 mL) was diluted with water (16 mL) and treated with 1N aqueous triflouromethanesulfonic acid (301 μL, 0.301 mmol). After stirring at room temperature for 20 minutes the reaction mixture was partitioned between dichloromethane (200 mL) and 5% aqueous bicarbonate (60 mL). The aqueous phase was extracted with dichloromethane (30 mL) and the combined organic phase was concentrated to yield the title compound (1.56 g) as a white foam.

Step 4: Allyl (1S,5R,6S)-6-[(1R)-(allyloxycarbonyloxy)-ethyl]-2-[4-(iodomethyl)-1,8-naphthosultamyl-methyl]-1-methyl-carbapen-2-em-3-carboxylate Allyl (1S,5R,6S)-6-[( 1R)-(allyloxycarbonyloxy)-ethyl]-2-[4-(hydroxymethyl)-1,8-naphthosultamyl-methyl]-1-methyl-carbapen-2-em-3-carboxylate was dissolved in dichloromethane (49 mL) and cooled in an ice bath under an atmosphere of nitrogen. Triethylamine (0.524 mL, 3.8 mmol) followed by methanesulfonyl chloride (0.258 mL, 3.23 mmol) was added and the reaction mixture was allowed to stir at 2° C. for 40 minutes. The reaction mixture was then partitioned between dichloromethane (250 mL) and 0.1 N aqueous HCl (200 mL), and the organic phase dried over MgSO₄ then concentrated and dried under vacuum for 20 hours. The resulting mesylate (1.7 g, quant.) was dissolved in acetone (60 mL) and sodium iodide (1.95 g, 13 mmol) was added. This suspension was stirred for 80 minutes at room temperature under a nitrogen atmosphere. The reaction mixture was then partitioned between dichloromethane (200 mL) and water (200 mL). The aqueous phase was extracted with dichloromethane (50 mL) and the combined organic phase was washed with 5% NaHSO₃ (2×75 mL), dried over MgSO₄ and then concentrated. The resulting yellow oil was lyophilized from benzene (40 mL) to afford the title compound (1.5 g, quant.) as an amorphous yellow solid.

¹H NMR (CDCl₃) 1.28 (d, 1-CH₃), 1.42 (d, C$\underline{H}_3$CHO), 3.36 (dq, H-1), 3.42 (dd, H-6), 4.13 (dd, H-5), 4.42–4.68 (m, OCO₂CH₂), 4.63 (d, 2-C$\underline{H}$aHb), 4.76–4.94 (m, CO₂CH₂), 5.10 (dq, CH₃C$\underline{H}$O), 5.20–5.34 (m, 3 vinyl-H), 5.38 (d, ArCH₂I), 5.38 (d, CHa$\underline{H}$b), 5.49 (m, vinyl-H), 5.80–5.90 (m, vinyl-H), 5.94–6.06 (m, vinyl-H), 6.72 (dd, Ar H-7), 7.60–7.64 (m, Ar H5 and Ar H6), 7.77 and 7.84 (two d's, Ar H2 and Ar H3)

PREPARATIVE EXAMPLE 7
SYNTHESIS OF 3-AZIDO-1(1,4-DIAZONIABICYCLO[2.2.2]OCT-1-YL)-PROPANE TRIFLUOROMETHANESULFONATE

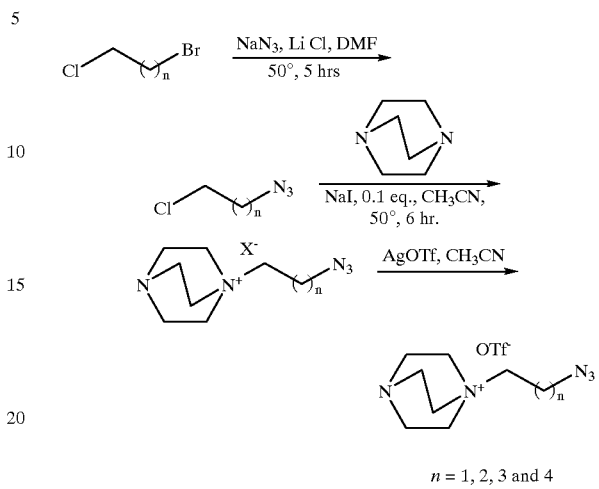

n = 1, 2, 3 and 4

Step 1: 1-Azido-3-chloropropane
Sodium azide (1.43 g, 22 mmol) and lithium chloride (0.93 g, 22 mmol) were added to DMF (10 ml) under nitrogen. To this was added 1,3-bromochloropropane (3.14 g, 2.0 ml, 20 mmol) and the reaction mixture was stirred and heated at 50° for 5 hours. The reaction mixture was diluted with water and extracted with petroleum ether. The organic phase was washed twice with water, dried over MgSO₄ and evaporated to give 1,3-azidochloropropane.

Step 2: 3-Azido-1(1,4-diazoniabicyclo[2.2.2]oct-1-yl)-propane trifluoromethanesulfonate
The azidochloropropane from Step 1 was dissolved in acetonitrile (8 ml) and treated with 1,4-diazabicyclo[2.2.2]octane (1.12 g, 10 mmol). Sodium iodide (0.15 g, 1 mmol) was added and the reaction was stirred under nitrogen at 50° for 6 hr. The solvent was removed under reduced pressure and the residue was triturated with ether, the ether solution was decanted off and the residue was taken up in acetonitrile (10 ml) and treated with silver trifluoromethane sulfonate (2.56 g, 10 mmol). After 10 min. the precipitated silver salts were filtered through a bed of celite and washed with a little acetonitrile. The filtrate and washings were evaporated to give the crude product which was crystallized from EtOH/Et₂O to give the crystalline product.

¹H NMR (D₂O, 300 MHz) δ2.02 (m, CH₂C$\underline{H}_2$CH₂), 3.17 (t, N(C$\underline{H}_2$CH₂)₃N⁺), 3.36 (m, CH₂N₃, CH₂CH₂C$\underline{H}_2$N⁺ and N(CH₂C$\underline{H}_2$)₃N⁺).

Following the procedures of Steps 1 and 2 of Preparative Example 7 and starting with the appropriate chlorobromoalkane, the compounds of Preparative Examples 8 to 10 are obtained.

PREPARATIVE EXAMPLE 8
2-AZIDO-1(1,4-DIAZONIABICYCLO[2.2.2]OCT-1-YL)-ETHANE TRIFLUOROMETHANESULFONATE

¹H NMR (D₂O, 300 MHz) δ3.18 (t, N(C$\underline{H}_2$CH₂)₃N⁺), 3.44 (m, CH₂N₃ and N(CH₂C$\underline{H}_2$)₃N⁺), 3.90 (t, N₃CH₂C$\underline{H}_2$N⁺).

PREPARATIVE EXAMPLE 9
4-AZIDO-1(1,4-DIAZONIABICYCLO[2.2.2]OCT-1-YL)-BUTANE TRIFLUOROMETHANESULFONATE

¹H NMR (D₂O, 500 MHz) δ1.63 and 1.84 (2 m, CH₂C$\underline{H}_2$C$\underline{H}_2$CH₂), 3.18 (t, N(C$\underline{H}_2$CH₂)₃N⁺), 3.27 (m, CH₂N₃), 3.39 (m, CH₂CH₂C$\underline{H}_2$N⁺ and N(CH₂C$\underline{H}_2$)₃N⁺).

PREPARATIVE EXAMPLE 10

5-AZIDO-1(1,4-DIAZONIABICYCLO[2.2.2]OCT-1-YL)-PENTANE TRIFLUOROMETHANESULFONATE $^1$H NMR (D$_2$O, 500 MHz) δ1.38, 1.60 and 1.76 (3 m, CH$_2$CH$_2$CH$_2$CH$_2$), 3.16 (t, N(CH$_2$CH$_2$ )$_3$N$^+$), 3.21 and 3.29 (m, CH$_2$CH$_2$CH$_2$N$^+$ and CH$_2$N$_3$), 3.34 (t, N(CH$_2$CH$_2$)$_3$)N$^+$).

PREPARATIVE EXAMPLE 11

3-AZIDO-1(1,4-DIAZONIABICYCLO[2.2.2]OCT-1-YL)-BUTANE TRIFLUOROMETHANE SULFONATE

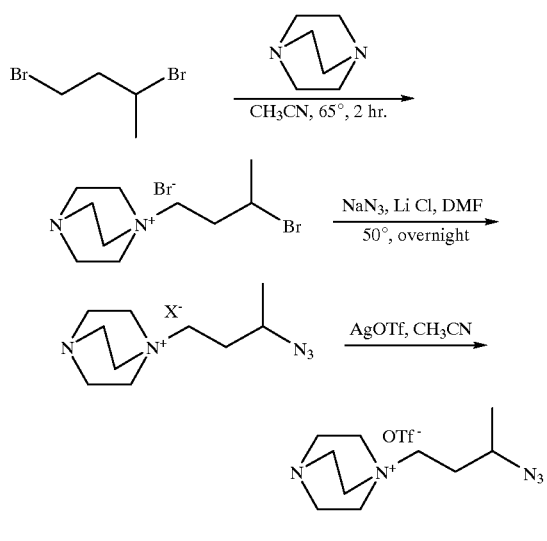

Step 1: 3-Bromo-1(1,4-diazoniabicyclo[2.2.2]oct-1-yl)-butane bromide

1,3-Dibromobutane (2.15 g, 1.2 ml, 10 mmol) was dissolved in acetonitrile (2 ml). DABCO (1.23 g, 11 mmol) was added. The reaction mixture was heated at 65° under nitrogen for 2 hr. The acetonitrile was removed under reduced pressure to give a white solid as the product.

$^1$H NMR (D$_2$O, 300 MHz) δ1.72 (d, CH$_3$), 2.28 (m, CH$_2$CH$_2$CH), 3.16 (t, N(CH$_2$CH$_2$)$_3$N$^+$), 3.4 (m, N(CH$_2$CH$_2$)$_3$N$^+$), 3.5 (m, CHCH$_2$CH$_2$N$^+$) and 4.2 (m, CHBr).

Step 2: 3-Azido-1(1,4-diazoniabicyclo[2.2.2]oct-1-yl)-butane trifluoromethanesulfonate

The product from Step 1 was dissolved in DMF (5 ml). Sodium azide (0.71 g, 11 mmol) and lithium chloride (0.5 g, 11 mmol) were added followed by sodium iodide (0.149 g, 1 mmol). The reaction was stirred at 50°, under nitrogen overnight. The DMF was removed under reduced pressure with an external bath temperature of 40°. The residue was taken up in acetonitrile (5 ml) and methanol (5 ml) and treated with silver triflate (2.8 g, 11 mmol). After 0.5 hr the precipitated silver salts were filtered off through a bed of celite and washed with a little methanol. The filtrate and washings were evaporated to give an oil. Trituration with ether (10 ml) for 1.5 hr gave the crystalline product (0.92 g).

$^1$H NMR (D$_2$O, 300 MHz) δ1.31 (d, CH$_3$), 1.94 (m, CH$_2$CH$_2$CH), 3.16 (t, N(CH$_2$CH$_2$ )$_3$N$^+$), 3.37 (m, N(CH$_2$CH$_2$)$_3$N$^+$), 3.33 (m, CHCH$_2$CH$_2$N$^+$) and 3.62 (m, CHN$_3$).

PREPARATIVE EXAMPLE 12

3-(N,N-DIALLYLOXYCARBONYGUANIDINO)-1(1,4-DIAZONIABICYCLO[2.2.2]OCT-1-YL)-PROPANE TRIFLUOROMETHANESULFONATE

Step 1: N,N-diallyloxycarbonyl-2-methyl-2-thiopseudourea

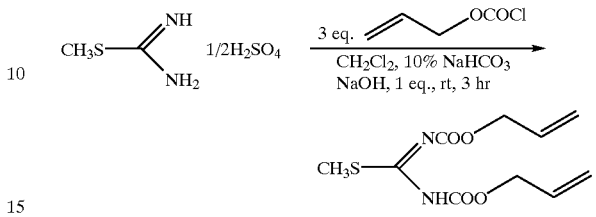

2-methyl-2-thiopseudourea sulfate (2 g) was dissolved in sodium bicarbonate (10% soln., 20 ml. To this was added methylene chloride (20 ml) followed by sodium hydroxide solution (5N, 2.8 ml) and allylchloroformate (4.5 ml) added dropwise over 5 min. The reaction was allowed to stir at room temperature for 3 hr., diluted with methylene chloride and the organic phase was separated. The aqueous phase was extracted once with methylene chloride and the combined organic phase was washed with water, satd. NaCl, and dried over MgSO$_4$ and evaporated to give the product (3.7 g)

$^1$H NMR (CDCl$_3$, 300 MHz) δ2.4 (s, CH$_3$S), 4.62 (m, OCH$_2$), 5.3 (m, CH$_2$=), 5.96 (m, CH=)

Step 2: 3-Amino-1(1,4-diazoniabicyclo[2.2.2]oct-1-yl)-propane chloride

The product from Preparative Example 7, (1 g) was dissolved in methanol (10 ml), 5% Rh/C (0.150 g) was added and the mixture reduced under 1 atm. of hydrogen overnight at room temperature. The catalyst was filtered off and washed with a little methanol. The filtrate and washings were evaporated to give the product (0.96 g).

$^1$H NMR (D$_2$O, 300 MHz) δ1.98 (m, CH$_2$CH$_2$CH$_2$), 2.79 (t, CH$_2$NH$_2$), 3.17 (t, N(CH$_2$CH$_2$ )$_3$N$^+$), 3.28 (m, , CH$_2$CH$_2$CH$_2$N$^+$) and 3.38 (t, N(CH$_2$CH$_2$)$_3$N$^+$).

Step 3: 3-(N,N-diallyloxycarbonyguanidino)-1(1,4-diazoniabicyclo[2.2.2]oct-1-yl)-propane trifluoromethanesulfonate

-continued

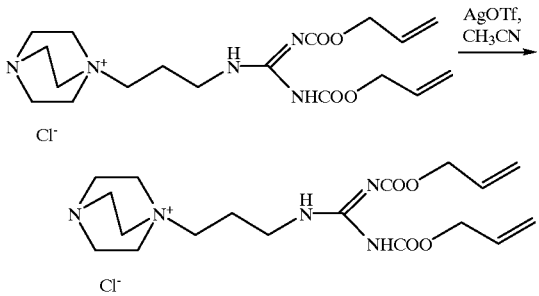

3-Amino-1(1,4-diazoniabicyclo[2.2.2]oct-1-yl)-propane chloride (200 mg,), from Step 2 was dissolved in DMF (2 ml), N,N-diallyloxycarbonyl-2-methyl-2-thiopseudourea (258 mg,) from Step 1 and triethylamine (417 mg, 3 eq.) were added followed by mercuric chloride (271 mg,). The reaction mixture was stirred under nitrogen for 2 hr. at room temperature. The mercury salts were filtered off and the residue washed with acetonitrile (2 ml). The filtrate and washings were evaporated under reduced pressure to remove most of the solvents and excess triethylamine. The residue was taken up in DMF (1 ml), acetonitrile (2 ml) and EtOH (2 ml) and treated with silver triflate (512 mg,). After stirring for 15 min. the silver salts were filtered off through a bed of celite, washed with acetonitrile and the filtrate and washings were evaporated overnight under high vacuum to give the product (560 mg) as a thick oil.

$^1$H NMR (CD$_3$CN, 300 MHz) δ2.0 (m, CH$_2$CH$_2$CH$_2$), 2.13 (s, CH$_3$S), 3.2 (m, N(CH$_2$CH$_2$ )$_3$N$^+$, CH$_2$CH$_2$CH$_n$N$^+$ and N(CH$_2$CH$_2$)$_3$N$^+$). 3.46 (m, CH$_2$NH), 4.55 and 4.67 (2 m, OCH$_2$ ), 5.3 (m, CH$_2$=), 5.97 (m, CH=).

PREPARATIVE EXAMPLE 13
N-(PYRIDIN-2-YL)-1-(4-AZA-1-AZONIA-BICYCLO[2.2.2]OCT-1-YL)ACETAMIDE TRIFLATE

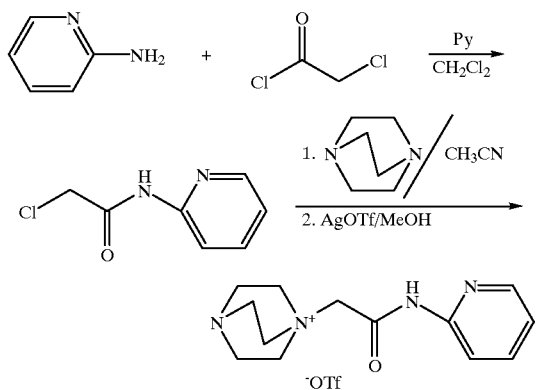

Step 1: N-(Pyridin-2-yl)chloroacetamide

To a solution of 2-aminopyridine (1.88 g, 20 mmol) and Et$_3$N (2.78 mL, 22 mmol) in CH$_2$Cl$_2$ (20 mL) was added chloroacetochloride (1.7 mL, 22 mmmol) slowly at 0° C. and stirred at room temperature for 2 hours. The mixture was washed with water and brine. The organic layer was dried over Na$_2$SO$_4$ and concentrated under vaccum to give the desired product (3.18 g) as a light brown solid.

Step 2: N-(Pyridin-2-yl)-1-(4-aza-1-azonia-bicyclo[2.2.2]oct-1-yl)acetamide triflate A solution of N-(pyridin-2-yl)chloroacetamide (1.0 g, 5.8 mmol), 1,4-diazabicyclo[2.2.2]octane (0.72 g, 6.4 mmol) and acetonitrile (30 mL) was stirred at room temperature overnight. The solvent was then removed. The residue was washed with CH$_2$Cl$_2$/hexane (1:1) and dried under vacuum to give the product (1.05 g, 3.7 mmol) as chloride. The chloride was dissolved in MeOH (10 mL) and treated with a solution of AgOTf (0.906 g, 3.5 mmol) in CH$_3$CN (4 mL). The mixture was stirred for 2 hrs, then filtered to remove the white precipitate. The filter cake was washed with CH$_3$CN. The combined filtrate was concentrated to give the yellow solid product (1.47 g) as a triflate salt.

$^1$H NMR (D$_2$O, 300 MHz) δ3.18 (t, N(CH$_2$CH$_2$)$_3$N$^+$), 3.70 (t, N(CH$_2$CH$_2$)$_3$N$^+$), 4.23 (s, CH$_3$CO), 7.22 (dd, Ar H-4), 7.74 (d, Ar H-5), 7.85 (t, Ar H-3), 8.30 (d, ArH-6).

PREPARATIVE EXAMPLE 14

N-(1-METHYLPYRIDIN-2-IUM)-1-(4-AZA-1-AZONIA-BICYCLO[2.2.2]OCT-1-YL)ACETAMIDE TRIFLATE

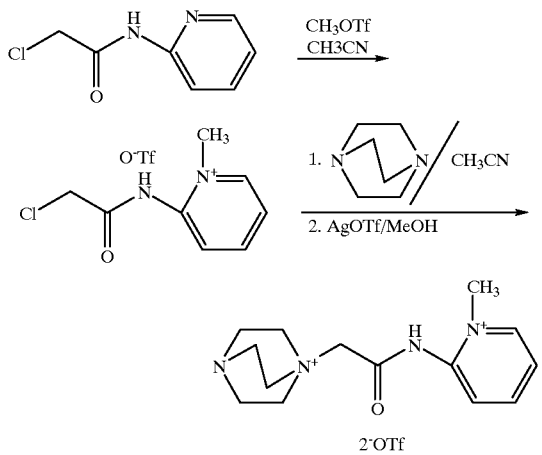

Step 1: N-(1-Methylpyridin-2-ium)chloroacetamide triflate

A solution of N-(pyridin-2-yl)chloroacetamide (0.105 g, 0.61 mmol) in CH$_3$CN (3 mL) was treated with methyl triflate (69 μL, 0.61 mmol). The mixture was then stirred overnight and concentrated to give the desired product (0.2 g).

Step 2: N-(1-Methylpyridin-2-ium)-1-(4-aza-1-azonia-bicvclo [2.2.2]oct-1-yl)acetamide triflate A mixture of N-(1-methylpyridin-2-ium)chloroacetamide triflate (0.2 g, 0.60 mmol), 1,4-diazabicyclo[2.2.2]octane (57 mg, 0.51 mmol), diisopropylethylamine (104 μL, 0.60 mmol) and CH$_3$CN (3 mL) was stirred at room temperature for 2 hrs. The solvent was removed and residue was dissolved in MeOH (2 mL) and treated with a solution of AgOTf (0.13 g, 50 mmol) in CH$_3$CN (1 mL). The mixture was stirred for 0.5 hr, then filtered to remove the white precipitate. The filter cake was washed with CH$_3$CN. The combined filtrate was concentrated to give product which was recrystalized from CH$_3$CN/Et$_2$O to give white crystal (0.18 g) as desired product.

$^1$H NMR (D$_2$O, 300 MHz) δ3.26 (t, N(CH$_2$CH$_2$)$_3$N$^+$), 3.75 (t, N(CH$_2$CH$_2$)$_3$N$^+$), 3.90 (s, CH$_3$N$^+$), 4.02 (s, CH$_2$CO), 6.98 (t, Ar H-4), 7.86 (t, Ar H-5), 8.18 (m, Ar H-3 and ArH-6).

PREPARATIVE EXAMPLE 15
N-(4-AZIDOMETHYLPHENYL)-1-(4-AZA-1-AZONIA-BICYCLO[2.2.2]OCT-1-YL)ACETAMIDE TRIFLATE

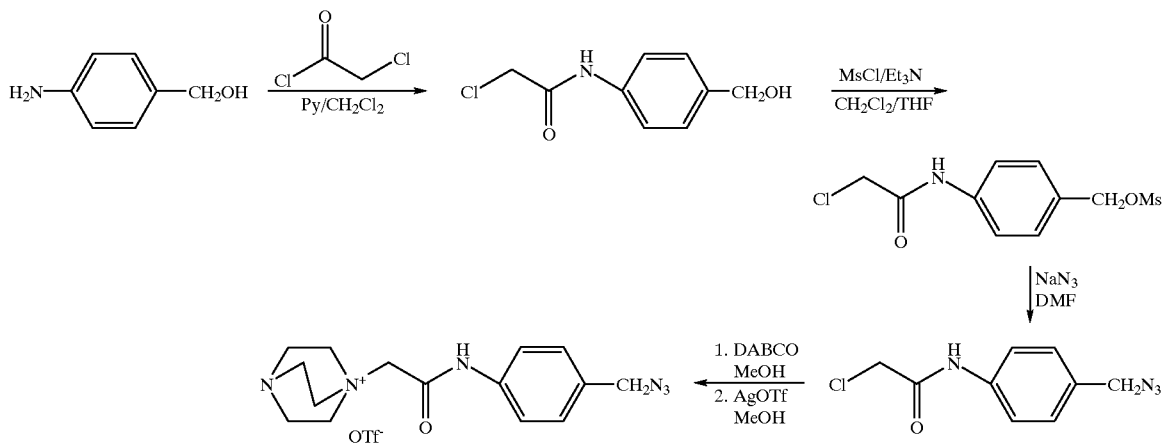

under vacuum. The residue was taken up in ethyl acetate and washed with water 3 times. The organic layer was dried over $Na_2SO_4$ and concentrated. The residue was chromato- Step 1: N-(4-Hydroxymethylphenyl)chloroacetamide A solution of 4-aminobenzyl alcohol (2 g, 16.3 mmol), pyridine (1.3 mL, 16.3 mmol) in $CH_2Cl_2$ (50 mL) was treated with chloroacetochloride (1.29 mL, 16.2 mmol) at 0° C. The mixture was stirred for 0.5 hr and then washed with water, 1N HCl, water and brine. It was dried over $Na_2SO_4$ and concentrated. The residue was chromatographed over silica gel (eluent: hexane:ethyl acetate v/v 2:1) to give the product (0.54 g) as a white solid.

Step 2: 4-(1-Chloroacetamido)benzyl methanesolfonate

A solution of N-(4-hydroxymethylphenyl) chloroacetamide (0.25 g, 1.25 mmol), $Et_3N$ (0.5 mL, 3.46 mmol), solvent $CH_2Cl_2$ (30 mL) and THF (10 mL) was treated with methanesulfonyl chloride (0.1 mL, 1.29 mmol) at 0° C. The mixture was kept at 0° C. for 0.5 hr and more $CH_2Cl_2$ was added. It was then washed with water and brine, dried over $Na_2SO_4$ and concentrated to give the product (0.313 g).

Step 3: N-(4-Azidomethylnhenyl)chloroacetamide

A mixture of 4-(1-chloroacetamido)benzyl methanesolfonate (0.313 g, 1.13 mmol), sodium azide (73 mg, 1.13 mmol), lithium chloride (48 mg, 1.13 mmol), DMF (10 mL) and catalytic amount of sodium iodide was stirred at room temperature for 3 days. Most of the DMF was then removed graphed over silica gel (eluent: Hexane:ethyl acetate v/v 2:1) to give the product (77 mg) as a white solid.

Step 4: N-(4-azidomethylphenyl)-1-(4-aza-1-azonia-bicyclo[2.2.2]oct-1-yl)acetamide triflate A solution of N-(4-azidomethylphenyl)chloroacetamide (77 mg, 0.343 mmol), 1,4-diazabicyclo[2.2.2]octane (35 mg, 0.313 mmol) and $CH_3CN$ (3 mL) was stirred at room temperature for 3 days. The solent was removed and the residue was dried under vacuum to give the product (0.115 g) as chloride. This chloride was dissolved in MeOH (3 mL) and treated with a solution of AgOTf (80 mg, 0.31 mmol) in $CH_3CN$ (0.5 mL). The mixture was stirred for 0.5 hr, then filtered to remove the white precipitate. The filter cake was washed with $CH_3CN$. The combined filtrate was concentrated to give the product (0.13 g) as a triflate salt.

$^1$H NMR ($CD_3CN$, 300 MHz) δ3.45 (t, N($CH_2CH_2$)$_3N^+$), 3.82 (t, N($CH_2CH_2$)$_3N^+$), 4.30 (s, $CH_2N_3$), 4.63 (s, $CH_2$-DABCO), 7.63 and 7.88 (2 d's, Ar-H).

PREPARATIVE EXAMPLE 16
N-(4-(2-(ALLYLOXYCARBONYLAMINO)ETHYL)PHENYL)-1-(4-AZA-1-AZONIA-BICYCLO[2.2.2]OCT-1-YL)ACETAMIDE TRIFLATE

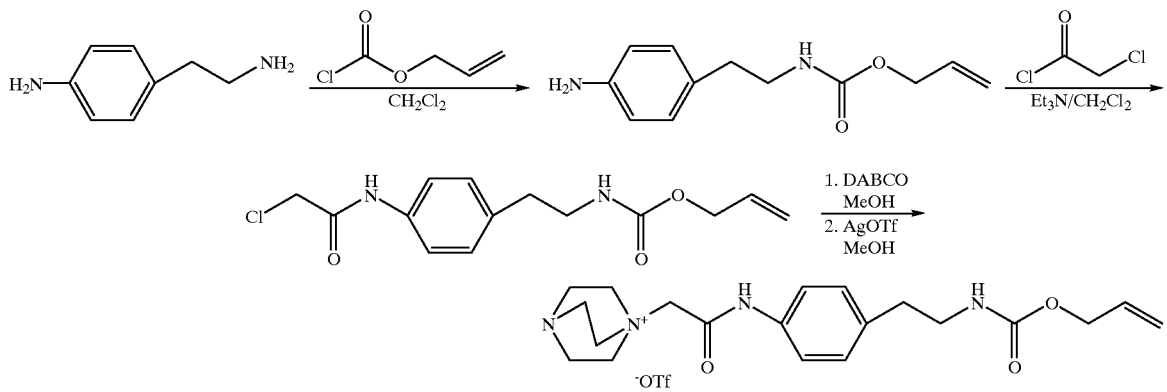

Step 1: N-(4-aminophenethyl)-O-allyl carbamate

To a solution of 4-aminophenethyl amine (2 g, 14.7 mmol) in $CH_2Cl_2$ (20 mL) was added allyl chloroformate (0.533 mL, 4.89 mmol) at 0° C. The mixture was kept at 0° C. for 0.5 hr and more CH$_2$Cl$_2$ was added. It was then washed with 5% NaHCO$_3$, water and brine, dried over Na$_2$SO$_4$ and concentrated. The residue was chromatographed over silica gel (eluent: ethyl acetate:hexane v/v 1:1) to give the product (1.38 g) as a white solid.

Step 2: N-(4-(2-(Allyloxycarbonylamino)ethyl)phenyl) chloroacetamide

A solution of N-(4-aminophenethyl)-O-allyl carbamate (1.38 g, 6.28 mmol), Et$_3$N (1.5 mL, 10.4 mmol) in CH$_2$Cl$_2$ (30 mL) was treated with chloroacetochloride (0.52 mL, 6.53 mmol) at 0° C. The mixture was stirred for 20 min and then washed with water, 1N HCl, water and brine. It was dried over Na$_2$SO$_4$ and concentrated to give the product (1.58) as a white solid.

Step 3 N-(4-(2-(Allyloxycarbonylamino)ethyl)phenyl)-1-(4-aza-1-azonia-bicyclo[2.2.2]oct-1-yl)acetamide triflate A solution of N-(4-(2-(allyloxycarbonylamino)ethyl) phenyl) chloroacetamide (0.5 g, 1.68 mmol), 1,4-diazabicyclo[2.2.2]octane (0.18 g, 1.61 mmol) and CH$_3$CN (10 mL) was stirred at room temperature overnight. The solid was collected by filtration and dried under vacuum to give the white crystal product (0.52 g) as chloride.

$^1$H NMR (CD$_3$OD, 300 MHz) δ2.75 (t, CH$_2$—Ar), 3.30 (m, CH$_2$NH and N(C$\underline{H}_2$CH$_2$)$_3$N$^+$), 3.70 (t, N(CH$_2$C$\underline{H}_2$)$_3$N$^+$), 4.15 (s, CH$_2$-DABCO), 4.49 (d, C$\underline{H}_2$CH=CH$_2$), 5.13 and 5.22 (2 d's, CH=C$\underline{H}_2$), 5.88 (m, C$\underline{H}$=CH$_2$), 7.20 and 7.53 (2 d's, ArH).

This chloride was dissolved in MeOH (10 mL) and treated with a solution of AgOTf (0.31 g, 1.21 mmol) in CH$_3$CN (2 mL). The mixture was stirred for 0.5 hr, then filtered to remove the white precipitate. The filter cake was washed with CH$_3$CN. The combined filtrate was concentrated to give the product (0.6 g) as a triflate salt.

PREPARATIVE EXAMPLE 17

N-(2-ALLYLOXYCARBONYLAMINO)ETHYL)-1-(4-AZA-1-AZONIA-BICYCLO[2.2.2]OCT-1-YL) ACETAMIDE TRIFLATE

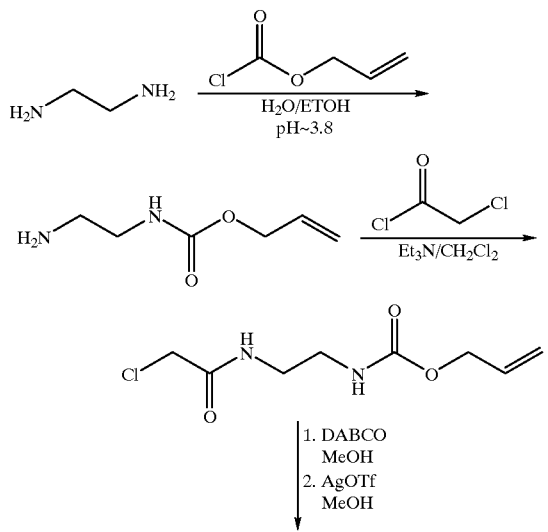

-continued

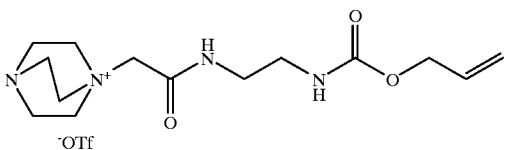

Step 1: N-(2-aminoethyl)-O-allyl carbamate

Ethylene diamine (1.8 g, 30 mmol) was dissolved in water (5.8 mL) with 5 drops of bromocresol green indicator. Methanesulfonyl chloride (c=0.92 g/mL H$_2$O) was added until the solution turned to pale yellow (pH~3.8). The solution was diluted with EtOH (16 mL), vigorously stirred, and treated simutaneously with solutions of allylchloroformate (3.61 g, 30 mmol) in dimethoxyethane (5.8 mL) and potassium acetate (c=50% w/v H$_2$O) by alternate dropwise additions to maintain the pale yellow-green colouration of the indicator. After the additions were complete the mixture was stirred for 1 hr and the volatiles were removed under vacuum. The residue was shaken with warter and filtered to remove small quantities of the bis-derivative. The filtrate was washed with benzene, basified with excess 40% aqueous NaOH, and then extracted with benzene. The organic layer was washed with brine, dried over Na$_2$SO$_4$ and concentrated to give the product (0.6 g) as a yellow oil.

Step 2: N-(2-Allyloxycarbonylaminoethyl)chloroacetamide

A solution of N-(2-aminoethyl)-O-allyl carbamate (0.6 g, 4.17 mmol), Et$_3$N (1.0 mL, 6.93 mmol) in CH$_2$Cl$_2$ (20 mL) was treated with chloroacetochloride (0.35 mL, 4.17 mmol) at 0° C. The mixture was stirred for 20 min and then washed with water, 1NHCl, water and brine. It was dried over Na$_2$SO$_4$ and concentrated to give the product (0.474 g) as a black solid.

Step 3: N-(2-Allyloxycarbonylamino)ethyl)-1-(4-aza-1-azonia-bicyclo[2.2.2]oct-1-yl)acetamide triflate A solution of N-(2-allyloxycarbonylaminoethyl) chloroacetamide (0.47 g, 2.13 mmol), 1,4-diazabicyclo[2.2.2] octane (0.167 g, 1.5 mmol) and CH$_3$CN (20 mL) was stirred at room temperature for 3 days. The solvent was removed and the residue was dried under vacuum to give the black solid product (0.63 g) as chloride.

$^1$H NMR (CD$_3$OD, 300 MHz) δ3.18 (m, N(C$\underline{H}_2$CH$_2$)$_3$N$^+$ and C$\underline{H}_2$NHCOCH$_2$), 3.32 (t, CH$_2$NHCOO), 3.60 (t, N(CH$_2$C$\underline{H}_2$)$_3$N$^+$), 3.94 (s, CH$_2$-DABCO), 4.53 (d, C$\underline{H}_2$CH=CH$_2$), 5.18 and 5.25 (2d's, CH=C$\underline{H}_2$), 5.92 (m, C$\underline{H}$=CH$_2$).

This chloride was dissolved in MeOH (10 mL) and treated with a solution of AgOTf (0.38 g, 1.48 mmol) in CH$_3$CN (2 mL). The mixture was stirred for 0.5 hr, then filtered to remove the white precipitate. The filter cake was washed with CH$_3$CN. The combined filtrate was concentrated to give the product (0.55 g) as a triflate salt.

PREPARATIVE EXAMPLE 18

N-((3-ALLYLOXYCARBONYLAMINO)PROPYL)-1-(4-AZA-1-AZONIA-BICYCLO[2.2.2]OCT-1-YL) ACETAMIDE TRIFLATE

Following the procedure described in Preparative Example 17, steps 1 to 3 and starting from 1,3-propanediamine, the title compound was obtained.

$^1$H NMR of chloride (CD$_3$OD, 300 MHz) δ1.95 (m, CH$_2$C$\underline{H}_2$CH$_2$), 3.40 (m, N(C$\underline{H}_2$CH$_2$)$_3$N$^+$ and C$\underline{H}_2$NHCOCH$_2$), 3.52 (q, CH$_2$NHCOO), 3.79 (t, N(CH$_2$C$\underline{H}_2$)$_3$N$^+$), 3.90 (s, CH$_2$-DABCO), 4.78 (d, C$\underline{H}_2$CH=CH$_2$), 5.43 and 5.55 (2d's, CH=C$\underline{H}_2$), 6.20 (m, C$\underline{H}$=CH$_2$).

PREPARATIVE EXAMPLE 19
N-(3-(2-ALLYLOXYCARBONYLAMINO)ETHYL) PHENYL)-1-(4-AZA-1-AZONIA-BICYCLO[2.2.2]OCT-1-YL)ACETAMIDE TRIFLATE

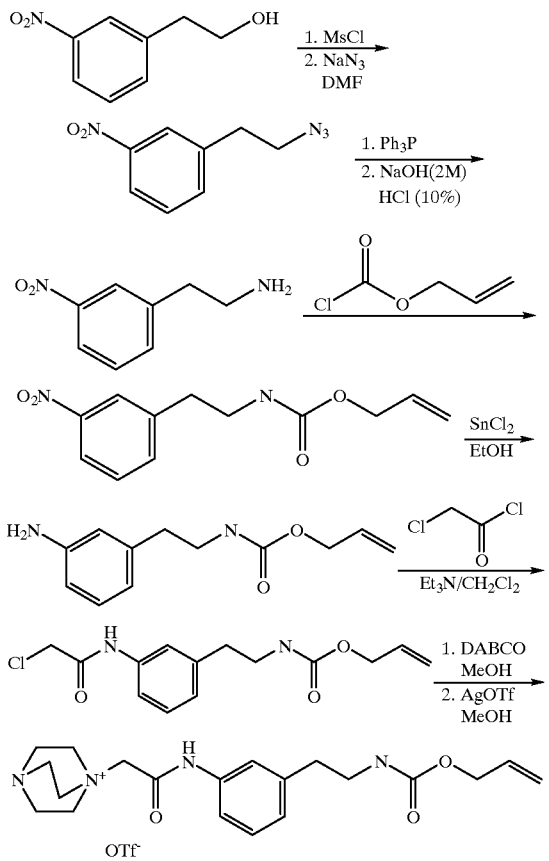

Step 1: 3-Nitrophenethyl azide

To a solution of 3-nitrophenethyl alcohol (2 g, 11.97 mmol), Et$_3$N (3.0 mL, 20.8 mmol) in CH$_2$Cl$_2$ (40 mL) was added methanesulfonyl chloride (1.0 mL, 12.9 mmol) at 0° C. After stirring for 0.5 hr, more CH$_2$Cl$_2$ was added. The solution was washed with water and brine, dried over Na$_2$SO$_4$ and concentrated. The residue was dissolved in DMF (30 mL), sodium azide (0.8 g,12.3 mmol), lithium chloride (0.53 g, 12.5 mmol) and catalytic amount of sodium iodide were added. The mixture was stirred at room temperature overnight. Most of DMF was then removed under vacuum and the residue was washed with water and brine, dried over Na$_2$SO$_4$ and concentrated. The residue was chromatographed over silica gel (eluent: hexane:ethyl acetate v/v 4:1) to give a pale yellow oil (1.8 g) as desired product.

Step 2: 3-Nitrophenethylamine

A mixture of 3-nitrophenethyl azide (0.9 g, 4.69 mmol), triphenyl phosphine (1.22 g, 4.66 mmol) and CH$_2$Cl$_2$ (80 mL) was stirred at room temperature for 3 days. Solvent was removed and the residue was taken up in EtOH (20 mL). The solution was heated to 70° C., added 2M NaOH aqueous solution (10 mL) and stirred at room temperature for 2 hrs. A 10% HCl aqueous solution (20 mL) was then added and refluxed for 2 hrs. After the mixture cool to room temperature, it was washed with benzene, basified with 5N NaOH to pH=12, extracted with ethyl acetate. The organic layer was dried over Na$_2$SO$_4$ and concentrated to give the product (0.63 g) as a yellow oil.

Step 3: N-(2-(3-Nitrophenyl)ethyl)-O-allyl carbamate

To a solution of 3-nitrophenylamine (0.62 g, 3.73 mmol) and Et$_3$N (0.8 mL, 5.54 mmol) in CH$_2$Cl$_2$ (20 mL) was added allyl chloroformate (0.4 mL, 3.77 mmol) at 0° C. The mixture was kept at 0° C. for 0.5 hr and more CH$_2$Cl$_2$ was added. It was then washed with 5% NaHCO$_3$, water and brine, dried over Na$_2$SO$_4$ and concentrated to give the product (0.9 g).

Step 4: N-(2-(3-Aminophenyl)ethyl)-O-allyl carbamate

A mixture of N-(2-(3-Aminophenyl)ethyl)-O-allyl carbamate (0.9 g, 3.6 mmol), tin(II) chloride dihydrate (4.1 g, 18 mmol) in EtOH (50 mL) was heated at 70° C. for 1 hr. The EtOH was removed and the residue was added water, basified with 5N NaOH to pH>10, extrated with CH$_2$Cl$_2$. The organic layer was washed with water and brine, dried over Na$_2$SO$_4$, concerntrated to give the product (0.66 g).

Step 5: N-((3-(2-allyloxycarbonylamino)ethyl)phenyl) chloroacetamide

A solution of N-(2-(3-Aminophenyl)ethyl)-O-allyl carbamate (0.66 g, 3.0 mmol), Et$_3$N (0.65 mL, 4.5 mmol) in CH$_2$Cl$_2$ (20 mL) was treated with chloroacetochloride (0.26 mL, 3.2 mmol) at 0° C. The mixture was stirred for 20 min and then washed with water, 1NHCl, water and brine. It was dried over Na$_2$SO$_4$ and concentrated to give the product (0.62 g).

Step 6: N-(3-(2-Allyloxycarbonylamino)ethyl)phenyl)-1-(4-aza-1-azonia-bicyclo[2.2.2]oct-1-yl)acetamide triflate A solution of N-((3-(2-allyloxycarbonylamino)ethyl) phenyl) chloroacetamide (0.32 g, 1.08 mmol), 1,4-diazabicyclo[2.2.2]octane (0.121 g, 1.08 mmol) and CH$_3$CN (10 mL) was stirred at room temperature overnight. The solvent was removed and the residue was dried under vacuum to give the product as chloride. This chloride was dissolved in MeOH (10 mL) and treated with a solution of AgOTf (0.27 g, 1.08 mmol) in CH$_3$CN (1 mL). The mixture was stirred for 0.5 hr, then filtered to remove the white precipitate. The filter cake was washed with CH$_3$CN. The combined filtrate was concentrated to give the product (0.50 g) as a triflate salt.

$^1$H NMR (CDCl$_3$, 300 MHz) δ2.75 (t, CH$_2$—Ar), 3.16 (t, N(CH$_2$CH$_2$)$_3$N$^+$), 3.38 (q, CH$_2$NH), 3.84 (t, N(CH$_2$CH$_2$)$_3$N$^+$), 4.51 (d, CH$_2$CH=CH$_2$), 4.81 (s, CH$_2$-DABCO), 5.16 and 5.22 (2 d's, CH=CH$_2$), 5.87 (m, CH=CH$_2$), 6.93 (d, ArH-5), 7.19 (t, ArH-2), 7.59 (m, ArH-4 and ArH-6).

PREPARATIVE EXAMPLE 20
N-(2-(2-ALLYLOXYCARBONYLAMINO)ETHYL) PHENYL)-1-(4-AZA-1-AZONIA-BICYCLO[2.2.2]OCT-1-YL)ACETAMIDE TRIFLATE

Following the procedure described in Example 19, step 1 to step 6 starting from 2-nitrophenyl alcohol, the title compound was obtained.

$^1$H H NMR of chloride (CD$_3$CN, 300 MHz) δ3.20 (t, CH$_2$—Ar), 3.42 (t, N(CH$_2$CH$_2$)$_3$N$^+$), 3.58 (q, CH$_2$NH), 3.84 (t, N(CH$_2$CH$_2$)$_3$N$^+$), 4.72 (d, CH$_2$CH=CH$_2$), 4.95 (s, CH$_2$-DABCO), 5.44 and 5.52 (2 d's, CH=CH$_2$), 6.15 (m CH=CH$_2$), 7.50 (m, 3 ArH), 7.94 (d, ArH-4).

PREPARATIVE EXAMPLE 21
1-(ALLYLOXYCARBONYL)-3-(4-AZA-1-AZONIA-BICYCLO[2.2.2]OCT-1-YL)PYRROLIDINE TRIFLATE

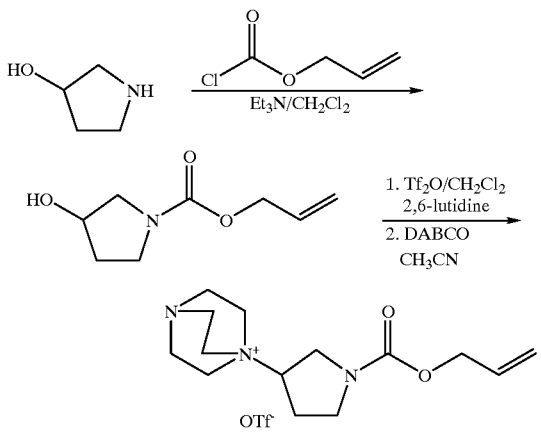

Step 1: 3-Hydroxy-1-allyloxcyarbonylpyrrolidine

To a solution of 3-hydroxypyrrolidine (0.35 g, 4.02 mmol) and Et$_3$N (1.16 mL, 8.04 mmol) in CH$_2$Cl$_2$ (20 mL) was added allyl chloroformate (0.47 mL, 4.43 mmol) at 0° C. The mixture was kept at 0° C. for 0.5 hr and more CH$_2$Cl$_2$ was added. It was then washed with 5% NaHCO$_3$, water and brine, dried over Na$_2$SO$_4$ and concentrated to give the product (0.34 g) as a yellow liquid.

Step 2: 1-(Allyloxycarbonyl)-3-(4-aza-1-azonia-bicyclo[2.2.2]oct-1-yl)pyrrolidine triflate 3-Hydroxy-1-allyloxycarbonylpyrrolidine (0.34 g, 1.99 mmol) was dissolved in CH$_2$Cl$_2$ (40 mL). 2,6-Lutidine (0.7 mL, 6 mmol) was added at –20° C. followed by adding triflic anhydride (0.5 mL, 2.97 mmol). The mixture was kept at –20° C. for 40 min, diluted with CH$_2$Cl$_2$, washed with water, 0.1 N HCl aqueous solution, water and brine, dried over Na$_2$SO$_4$ and concentrated to give the trifalte (0.63 g). The triflate (0.43 g, 1.42 mmol) was reacted with 1,4-diazabicyclo[2.2.2]octane (0.15 g, 1.34 mmol) in CH$_3$CN overnight. The solvent was removed and the residue was dried under vacuum to give the product (0.42 g).

$^1$H NMR (CD$_3$CN, 300 MHz) δ2.20 (m, CHC$\underline{H}_2$CH$_2$N), 3.26 (t, N(C$\underline{H}_2$CH$_2$)$_3$N$^+$), 3.50 (t, N(CH$_2$C$\underline{H}_2$)$_3$N$^+$), 3.72 (m, CH$_2$C$\underline{H}_2$N), 3.80 (m, CHC$\underline{H}_2$N), 4.22 (m, CH$_2$C$\underline{H}$CH$_2$), 4.58 (s, C$\underline{H}_2$CH=CH$_2$), 5.22 and 5.30 (2d's, CH=C$\underline{H}_2$), 5.90 (m, C$\underline{H}$=CH$_2$).

PREPARATIVE EXAMPLE 22
N-(2-((N',N"-DIALLYLOXYCARBONYL)GUANIDINO)ETHYL)-1-(4-AZA-1-AZONIA-BICYCLO[2.2.2]OCT-1-YL)ACETAMIDE TRIFLATE

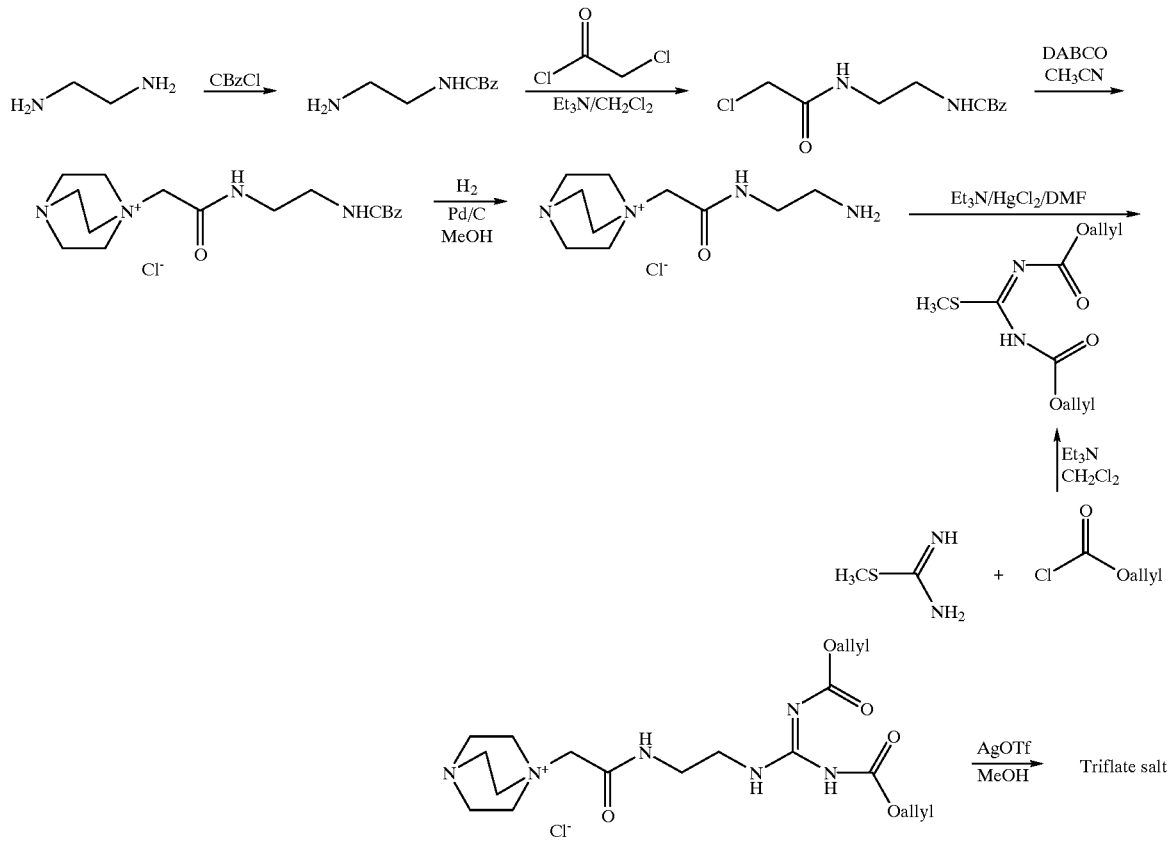

Step 1: N-(2-(Benzylamino)ethyl)-1-(4-aza-1-azonia-bicyclo[2.2.2]oct-1-yl)acetamide chloride Following the procedure described in Preparative Example 17, steps 1 to 3 and starting with ethylene diamine and benzoyl chloride, N-(2-(benzylamino)ethyl)-1-(4-aza-1-azonia-bibcyclo[2.2.2]oct-1-yl)acetamide chloride was obtained.

Step 2: N-(2-Aminoethyl)-1-(4-aza-1-azonia-bicyclo[2.2.2]oct-1-yl)acetamide chloride A solution of N-(2-(benzylamino)ethyl-1-(4-aza-1-azonia-bibcyclo[2.2.2]oct-1-yl)acetamide chloride (0.36 g, 1.02 mmol) in MeOH (50 mL) was subjected hydrogenation with balloon at the presence of Pd on carbon (5% Pd/C, 36 mg) for 2 hrs. Catalyst was filtered off and solvented was evaporated under vacuum to give the product (0.26 g).

Step 3: N-(2-((N',N''-Diallyloxycarbonyl)guanidino)ethyl)-1-(4-aza-1-azonia-bicyclo[2.2.2]oct-1-yl)acetamide triflate A mixture N-(2-Aminoethyl)-1-(4-aza-1-azonia-bibcyclo[2.2.2]oct-1-yl)acetamide chloride (0.26 g, 1.04 mmol) and N,N'-allyloxycarbonyl-2-methyl-2-thiopseudourea (0.29 g, 1.12 mmol) in DMF (2.5 mL) was treated with Et$_3$N (0.45 mL, 3.11 mmol) and HgCl$_2$ (0.31 g, 1.12 mmol), stirred for 2 hrs. The precipitate was filtered and solvent and Et$_3$N were removed under vacuum. The residue was taken up in DMF (2 mL), treated with AgOTf (0.54 g, 2.1 mmol) for 15 min, filtered to remove the white precipitate. The filter cake was washed with CH$_3$CN. The combined filtrate was concentrated to give the product (0.52 g) as a triflate salt.

$^1$H NMR (CD$_3$CN, 300 MHz) δ3.42 (t, N(C$\underline{H}_2$CH$_2$)$_3$N$^+$), 3.75 (t, N(CH$_2$C$\underline{H}_2$)$_3$N$^+$), 4.13 and 4.38 (2 t's, NHC$\underline{H}_2$C $\underline{H}_2$NH), 4.85 and 4.96 (2 d's, OCH$_2$), 5.48–5.70 (m, CH=C $\underline{H}_2$), 6.22–6.35 (m, C$\underline{H}$=CH$_2$).

PREPARATIVE EXAMPLE 23
(S)-(−)-3-AZIDO-1-(4-AZA-1-AZONIA-BICYCLO[2.2.2]OCT-1-YL)-2-METHYLPROPANE TRIFLATE

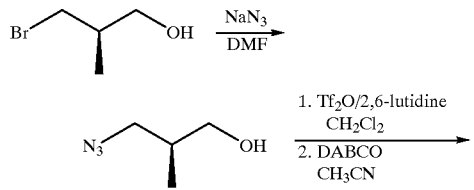

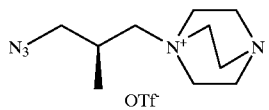

Step 1: (R)-(−)-3-azido-2-methylpropanol

A mixture of (R)-(−)-3-bromo-2-methylpropanol (1 g, 6.53 mmol), sodium azide (0.47 g, 7.23 mmol), lithium chloride (0.31 g, 7.29 mmol) and DMF (10 mL) was heated at 50° C. overnight. most of DMF was then removed. The residue was taken up in ethyl acetate, washed with water and brine, dried over Na$_2$SO$_4$ and concentrated to give the product (0.64 g).

Step 2: (S)-(−)-3-Azido-1-(4-aza-1-azonia-bicyclo[2.2.2]oct-1-yl)-2-methylpropane triflate (R)-(−)-3-azido-2-methylpropanol (0.64 g, 5.56 mmol) was dissolved in CH$_2$Cl$_2$ (40 mL). 2,6-lutidine (1.9 mL, 16.3 mmol) was added at −20° C. followed by adding trifalic anhydride (1.4 mL, 8.32 mmol). The mixture was kept in −20° C. for 40 min, diluted with CH$_2$Cl$_2$, washed with water, 0.1 N HCl aqueous solution, water and brine, dried over Na$_2$SO$_4$ and concentrated to give the trifalte (1.33 g). The triflate (0.7 g, 2.83 mmol) was reacted with 1,4-diazabicyclo[2.2.2]octane (0.31 g, 2.77 mmol) in CH$_3$CN for 3 hrs. The solvent was removed and the residue was dried under vacuum to give the product (1.0 g).

$^1$H NMR (CDCl$_3$, 300 MHz) δ1.22 (d, CH$_3$), 2.48 (m, C $\underline{H}$CH$_3$), 3.24 (t, N(C$\underline{H}_2$CH$_2$)$_3$N$^+$), 3.32 (t, CH$_2$N$_3$), 3.52 (t, N(CH$_2$C$\underline{H}_2$)$_3$N$^+$), 3.63 (m, CH$_2$N$^+$).

PREPARATIVE EXAMPLE 24
(1S,5R,6S)-2-{6-[2-(4-(3-AMMONIOPROPYL)-1,4-DIAZONIA[2.2.2]OCT-1YL)-ETHYL]-1,1-DIOXO-2-H-1-THIA-2-AZA-ACENAPHTHALEN-2-YL-METHYL}-6-[1(R)-HYDROXYETHYL]-1-METHYL-CARBAPEN-2-EM-3-CARBOXYLATE DICHLORIDE

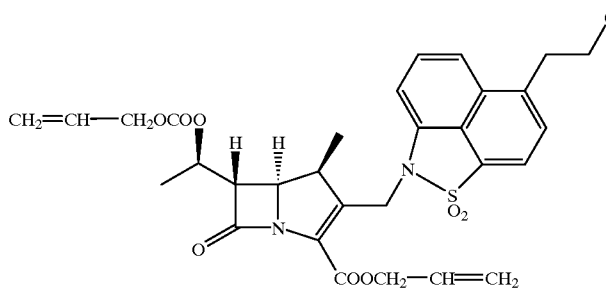

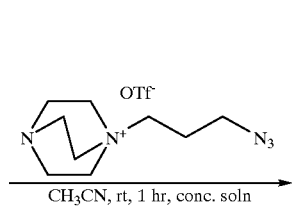

CH$_3$CN, rt, 1 hr, conc. soln

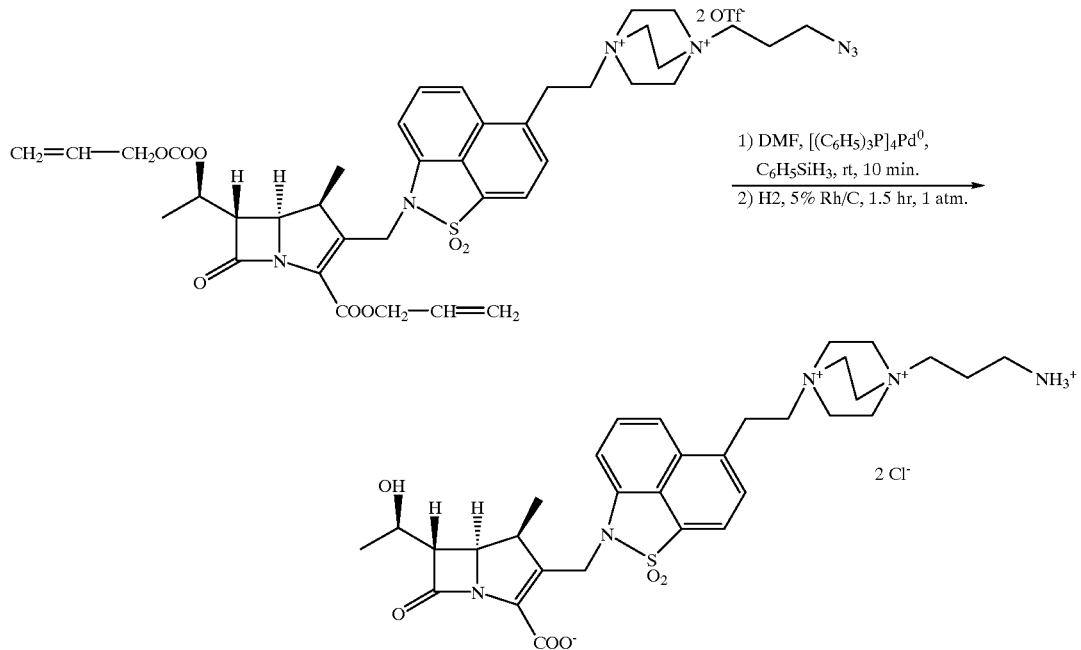

Step 1: Allyl (1S,5R,6S)--6-[(1R)-(allyloxycarbonyloxy)-ethyl]-2-[6-[2-(4-(3-azidopropyl)-1,4-diazonia[2.2.2]oct-1yl]-ethyl-1,1-dioxo-2-H-1-thia-2-aza-acenaphthalen-2-yl-methyl-1-methyl-carbapen-2-em-3-carboxylate bis (trifluoromethanesulfonate)

Allyl (1S,5R,6S)--6-[(1R)-(allyloxycarbonyloxy)-ethyl]-2-[6-(2-trifluoromethanesulfonyloxyethyl)-ethyl]-1,1-dioxo-2H-1-thia-2-aza-acenaphthalen-2-yl-methyl)-1-methyl-carbapen-2-em-3-carboxylate from Step 4, Preparative Example 2, (150 mg,) was dissolved in acetonitrile (1.5 ml), 3-Azido-1(1,4-diazoniabicyclo[2.2.2]oct-1-yl)-propane trifluoromethanesulfonate (85 mg,) from Step 2, Preparative Example 7, was added. The reaction was stirred 5 min. and the solvent was evaporated under vacuum to give a thick oil which was stirred at room temperature for 45 min. The residual solvent was removed to give the product which was used in the next step without purification.

Step 2: (1S,5R,6S)--2-{6-[2-(4-(3-ammoniopropyl)-1,4-diazonia[2.2.2]oct-1yl)-ethyl]-1,1-dioxo-2-H-1-thia-2-aza-acenaphthalen-2-yl-methyl]-6-[1(R)-hydroxyethyl]-1-methyl-carbapen-2-em-3-carboxylate dichloride Allyl (1S,5R,6S)--6-[(1R)-(allyloxycarbonyloxy)-ethyl]-2-{6-[2-(4-(3-ammoniopropyl)-1,4-diazonia[2.2.2]oct-1yl]-ethyl-]-1,1-dioxo-2H-1-thia-2-aza-acenaphthalen-2-yl-methyl)-1-methyl-carbapen-2-em-3-carboxylate bis (trifluoromethanesulfonate) from Step 1 was dissolved in DMF (1.5 ml), Phenylsilane (115 ml) was added, followed by tetrakis(triphenylphosphine)palladium(0) (22.5 mg, 0.019 mmol). The reaction was stirred at room temperature for 10 min. then diluted with ether (5 ml) to precipitate the product. The ether solution was decanted off and the residue washed with 2×7 ml ether. The combined ether solutions were centrifuged and the precipitate combined with the original precipitate was dissolved in acetonitrile/water 1/1 (2 ml). This solution was applied to a column of Macro-Prep CM weak cation exchange resin (5 ml). The column was eluted with 1:1 acetonitrile-water (8 ml) followed by water (10 ml). The resin was eluted with 5% aqueous sodium chloride (75 ml) and collected in 5×15 ml fractions. The first four fractions containing the product were combined and treated with 5% rhodium on carbon (50 mg) and stirred under an atmosphere of hydrogen. After 1 hour the catalyst was filtered off and the filtrate was loaded onto a Rainin Microsorb C18 RP HPLC column (2×30 cm). Gradient elution with acetonitrile/0.12M aqueous ammonium chloride gave pure product containing fractions which were combined and concentrated under vacuum. The concentrated product was applied to a column of Amberchrome CG-161 4 ml) which was eluted with water (10 ml) followed by 1:1 acetonitrile-water (10 ml). The acetonitrile-water eluate was lyophilized to give the product (32 mg).

$^1$H NMR (D$_2$O, 500 MHz) δ1.04(d, 1-CH$_3$), 1.17 (d, C$\underline{H}_3$CHOH), 2.31 (m, CH$_2$C$\underline{H}_2$CH$_2$), 2.97 (m, H-1), 3.14(t, CH$_2$NH$_3$+), 3.36 (d of d, H-6), 3.64 (m, ArCH$_2$), 3.77 (m, ArCH$_2$C$\underline{H}_2$), 3.91 (d of d, H-5), 3.93 (t, CH$_2$CH$_2$C$\underline{H}_2$N$^+$), 4.09 (m, CH$_3$C$\underline{H}$OH), 4.16 and 4.28 (2t, $^+$N(C$\underline{H}_2$C$\underline{H}_2$)$_3$N$^+$), 4.46 (d, 2-C$\underline{H}$aHb), 5.08 (d, 2-CHa$\underline{Hb}$), 6.56 (d, ArH), 7.28 (t, ArH), 7.35 (d, ArH), 7.69 (d, ArH), 7.95 (d, ArH).

PREPARATIVE EXAMPLE 25

(1S,5R,6S)--2-{6-[2-(4-(2-AMMONIOETHYL)-1,4-DIAZONIA[2.2.2]OCT-1YL)-ETHYL]-1,1-DIOXO-2-H-1-THIA-2-AZA-ACENAPHTHALEN-2-YL-METHYL}-6-[1(R)-HYDROXYETHYL]-1-METHYL-CARBAPEN-2-EM-3-CARBOXYLATE DICHLORIDE

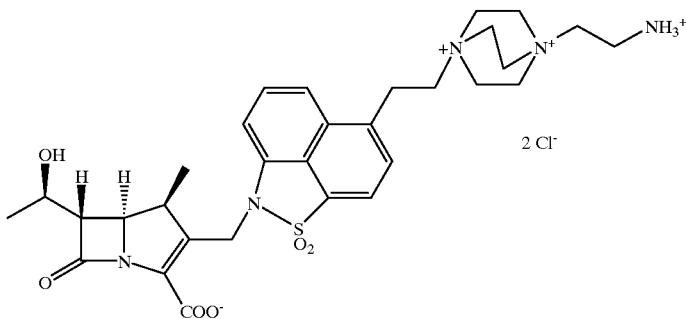

Substituting 2-Azido-1(1,4-diazoniabicyclo[2.2.2]oct-1-yl)-ethane trifluoromethanesulfonate for 3-Azido-1(1,4-diazoniabicyclo[2.2.2]oct-1-yl)-propane trifluoromethanesulfonate in Preparative Example 24, Step 1 above, and following the procedure of Step 2 one obtains the desired product.

$^1$H NMR (D$_2$O, 500 MHz) δ1.07 (d, 1-CH$_3$), 1.18 (d, CH$_3$CHOH), 2.31 (m, CH$_2$CH$_2$CH$_2$), 3.12 (m, H-1,), 3.37 (d of d, H-6), 3.56 (m, ArCH$_2$), 3.68 (m, ArCH$_2$CH$_2$), 3.9 to 4.0 (m, H-5 and +NH$_3$CH$_2$CH$_2$N$^+$), 4.11 (m, CH$_3$CHOH), 4.25 (m, N(CH$_2$CH$_2$)$_3$N$^+$), 4.51 (d, 2-CHaHb), 5.12 (d, 2-CHa Hb), 6.64 (d, ArH), 7.27 (t, ArH), 7.42 (d, ArH), 7.73 (d, ArH), 7.95 (d, ArH).

Substituting 4-Azido-1(1,4-diazoniabicyclo[2.2.2]oct-1-yl)-butane trifluoromethanesulfonate for 3-Azido-1(1,4-diazoniabicyclo[2.2.2]oct-1-yl)-propane trifluoromethanesulfonate in Preparative Example 24, Step 1 above, and following the procedure of Step 2 one obtains the desired product.

$^1$H NMR (D$_2$O, 500 MHz) δ1.09 (d, 1-CH$_3$), 1.19 (d, CH$_3$CHOH), 1.77 and 1.8 (2m, $^+$NH$_3$CH$_2$CH$_2$CH$_2$CH$_2$), 3.02 (m, H-1), 3.09 (t, CH$_2$NH$_3$+), 3.38 (d of d, H-6), 3.68 (m, ArCH$_2$CH$_2$), 3.96 (d of d, H-5), 3.94 (t, CH$_2$CH$_2$CH$_2$N$^+$), 4.12 and 4.24 (2m, CH$_3$CHOH and N(CH$_2$CH$_2$)$_3$N$^+$), 4.52 (d, 2-CHaHb), 5.13 (d, 2-CHaHb), 6.65 (d, ArH), 7.38 (t, ArH), 7.42 (d, ArH), 7.73 (d, ArH), 8.0 (d, ArH).

PREPARATIVE EXAMPLE 26
(1S,5R,6S)--2-{6-[2-(4-(4-AMMONIOBUTYL)-1,4-DIAZONIA[2.2.2]OCT-1YL)-ETHYL]-1,1-DIOXO-2-H-1-THIA-2-AZA-ACENAPHTHALEN-2-YL-METHYL}-6-[1(R)-HYDROXYETHYL]-1-METHYL-CARBAPEN-2-EM-3-CARBOXYLATE DICHLORIDE

PREPARATIVE EXAMPLE 27
(1S,5R,6S)--2-{6-[2-(4-(5-AMMONIOPENTYL)-1,4-DIAZONIA[2.2.2]OCT-1YL)-ETHYL]-1,1-DIOXO-2-H-1-THIA-2-AZA-ACENAPHTHALEN-2-YL-METHYL}-6-[1(R)-HYDROXYETHYL]-1-METHYL-CARBAPEN-2-EM-3-CARBOXYLATE DICHLORIDE

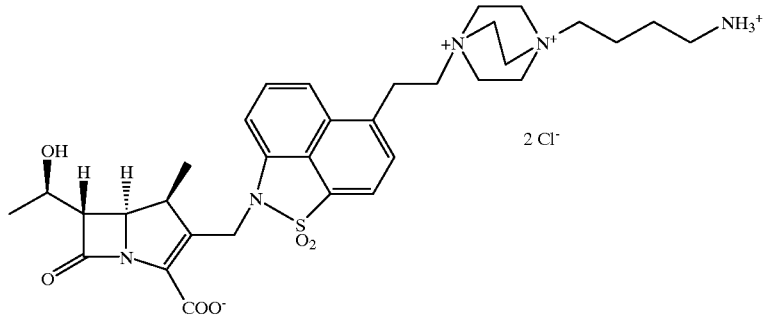

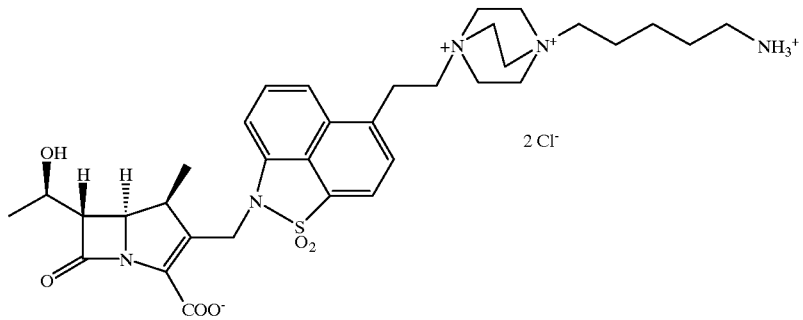

Substituting 5-Azido-1(1,4-diazoniabicyclo[2.2.2]oct-1-yl)-pentane trifluoromethanesulfonate for 3-Azido-1(1,4-diazoniabicyclo[2.2.2]oct-1-yl)-propane trifluoromethanesulfonate in Preparative Example 24, Step 1 above, and following the procedure of Step 2, one obtains the desired product.

$^1$H NMR (D$_2$O, 500 MHz) δ1.13 (d, 1-CH$_3$), 1.20 (d, CH$_3$CHOH), 1.47, 1.75 and 1.92 (3m, $^+$NH$_3$CH$_2$CH$_2$CH$_2$CH$_2$), 3.01 (t, CH$_2$NH$_3^+$), 3.08 (m, H-1), 3.39 (d of d, H-6), 3.63 and 3.72 (2m, ArCH$_2$CH$_2$), 3.96 (t, CH$_2$CH$_2$CH$_2$N$^+$), 4.0 (d of d, H-5), 4.09 (m, N$^+$(CH$_2$CH$_2$)$_3$N$^+$), 4.14 (m, CH$_3$CHOH), 4.22 (m, N$^+$(CH$_2$CH$_2$)$_3$N$^+$), 4.59 (d, 2-CHaHb), 5.18 (d, 2-CHaHb), 6.74 (d, ArH), 7.49(m, ArH), 7.77 (d, ArH), 8.05 (d, ArH).

Substituting 3-Azido-1(1,4-diazoniabicyclo[2.2.2]oct-1-yl)-butane trifluoromethanesulfonate for 3-Azido-1(1,4-diazoniabicyclo[2.2.2]oct-1-yl)-propane trifluoromethanesulfonate in Preparative Example 24, Step 1 above, and following the procedure of Step 2, one obtains the desired product.

$^1$H NMR (D$_2$O, 500 MHz) δ1.11 (d, 1-CH$_3$), 1.19 (d, CH$_3$CHOH), 1.38 (d, CH$_3$CHNH$_3^+$), 2.2 and 2.34 (2m, diastereomeric CH$_2$CH$_2$CH$_2$), 3.06 (m, H-1), 3.39 (d of d, H-6), 3.53 (m, CH$_3$CHNH$_3^+$), 3.69 (m, ArCH$_2$), 3.80 (m, ArCH$_2$CH$_2$), 3.96 (t, CH$_2$CH$_2$CH$_2$N$^+$), 3.98 (d of d, H-5), 4.13 (m, CH$_3$CHOH and $^+$N(CH$_2$CH$_2$)$_3$N$^+$), 4.24 ($^+$N(CH$_2$CH$_2$)$_3$N$^+$), 4.55 (d, 2-CHaHb), 5.16 (d, 2-CHaHb), 6.69 (d, ArH), 7.43 (m, ArH), 7.75 (d, ArH), 8.20 (d, ArH).

PREPARATIVE EXAMPLE 28
(1S,5R,6S)--2-{6-[2-(4-(3-AMMONIO-3-METHYLPROPYL)-1,4-DIAZONIA[2.2.2]OCT-1YL)-ETHYL]-1,1-DIOXO-2-H-1-THIA-2-AZA-ACENAPHTHALEN-2-YL-METHYL}-6-[1(R)-HYDROXYETHYL]-1-METHYL-CARBAPEN-2-EM-3-CARBOXYLATE DICHLORIDE

PREPARATIVE EXAMPLE 29
(1S,5R,6S)-6-(1(R)-HYDROXY-ETHYL)-1-METHYL-2-{6-(2-(4-(3(R)-AMONIO-2-METHYLPROPYL)-1,4-DIAZONIA-BICYCLO[2.2.2]OCT-1-YL)-ETHYL)-1,1-DIOXO- 1H-1-THIA-2-AZA-ACENAPHTHYLEN-2-YL-METHYL}CARBAPEN-2-EM-3-CARBOXYLATE DICHLORIDE

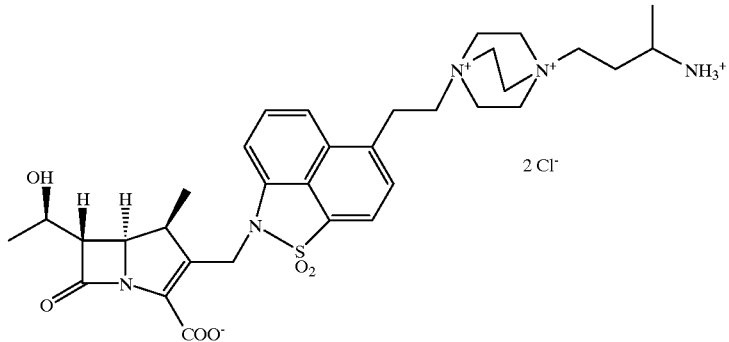

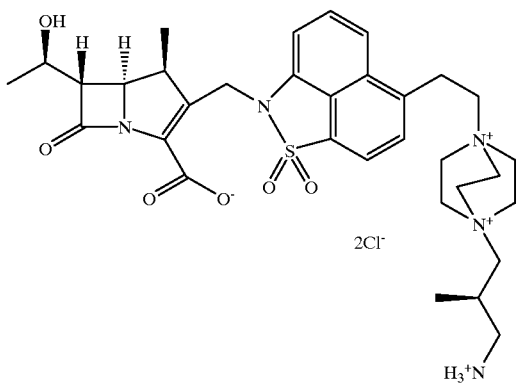

Starting with the product of Preparative Example 23 and following the procedure of steps 1 and 2 of Preparative Example 24 one obtains the title compound.

$^1$H NMR (D$_2$O, 500 MHz) δ1.12 (d, 1-CH$_3$), 1.19 (d, CH$_3$-CHOH), 1.26 (d, CH$_3$CH), 2.50 (m, CHCH$_3$), 2.88 (m, H-1), 3.04 (m, CHCH$_2$NH$_2$), 3.39 (t, H-5), 3.65–3.72 (m, CH$_2$Ar and CHCH$_2$N$^+$), 3.95 (m, H-6 and CH$_2$CH$_2$N$^+$), 4.16 (t, N$^+$(CH$_2$CH$_2$)$_3$N$^+$), 4.23 (t, N$^+$(CH$_2$CH$_2$)$_3$N$^+$), 4.56 and 5.17 (2d's, 2-CHaHb), 6.72 (d, Naphthosultam H-6), 7.47 (m, Naphthosultam H-3, H-5), 7.76 (d, Naphthosultam H-7), 8.03 (d, Naphthosultam H-2).

PREPARATIVE EXAMPLE 30
(1S,5R,6S)--2-{6-[2-(4-(3-METHYLAMMONIOPROPYL)-1,4-DIAZONIA[2.2.2]OCT-1YL)-ETHYL]-1,1-DIOXO-2-H-1-THIA-2-AZA-ACENAPHTHALEN-2-YL-METHYL}-6-[1(R)-HYDROXYETHYL]-1-METHYL-CARBAPEN-2-EM-3-CARBOXYLATE DICHLORIDE

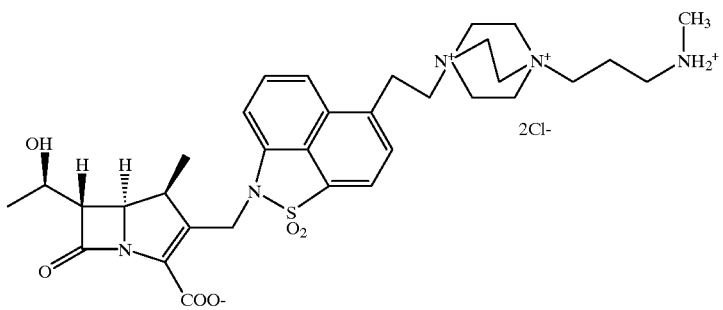

Starting with N-[$^3$-($^4$-aza-1-azonia-bicyclo[2,2,2]oct-1-yl-propyl]N-methylcarbamate and following the procedure of steps 1 and 2 of Preparative Example 24 obtains the title compound.

$^1$H NMR (D$_2$O, 500 MHz) δ1.12 (d, 1-CH$_3$), 1.19 (d, CH$_3$CHOH), 2.32 (m, CH$_2$CH$_2$CH$_2$), 2.75 (s, N—CH$_3$), 3.07 (m, H-1), 3.15 (t, CH$_3$CH$_2$NH$_3$$^+$), 3.39 (d of d, H-6), 3.73 (m, ArCH$_2$ and ArCH$_2$CH$_2$), 3.95 (t, CH$_2$CH$_2$CH$_2$N$^+$), 3.98 (d of d, H-5), 4.13 (m, CH$_3$CHOH and $^+$N(CH$_n$CH$_2$ )$_3$N$^+$), 4.24 ($^+$N(CH$_2$CH$_2$)$_3$N$^+$), 4.56 (d, 2-CHaHb), 5.17 (d, 2-CHaHb), 6.71 (d, ArH), 7.45 (m, ArH), 7.75 (d, ArH), 8.20 (d, ArH).

PREPARATIVE EXAMPLE 31
(1S,5R,6S)-6-(1(R)-HYDROXY-ETHYL)-1-METHYL-2-(6-(2-(4-(3-AMONIOPROPYL)AMINOCARBONYLMETHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL) CARBAPEN-2-EM-3-CARBOXYLATE DICHLORIDE

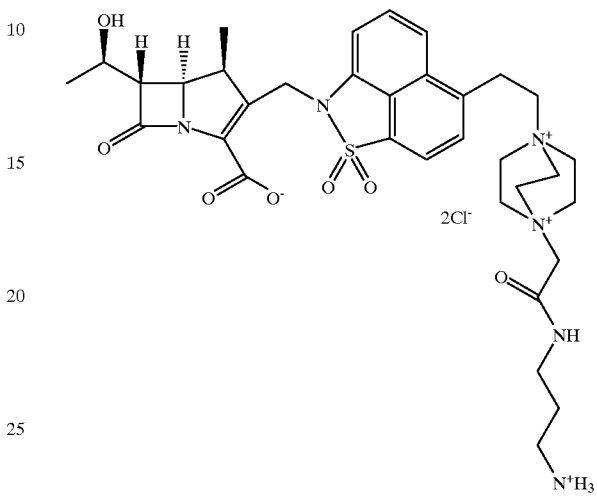

Starting with the product of Preparative Example 17, step 3 and following the procedure of steps 1 and 2 of Preparative Example 24 one obtains the title compound.

$^1$H NMR (D$_2$O, 500 MHz) δ1.09 (d, 1-CH$_3$), 1.19 (d, CH$_3$-CHOH), 1.91 (m, CH$_2$CH$_2$CH$_2$), 3.03 (m, H-1 and CH$_2$CH$_2$CH$_2$NH$_2$), 3.37 (t, H-5 and CH$_2$CH$_2$CH$_2$NH$_2$) 3.67 (m, CH$_2$Ar), 3.94 (m, H-6 and CH$_2$CH$_2$N$^+$), 4.11 (t, CHOH), 4.20 (t, N$^+$(CH$_2$CH$_2$)$_3$N$^+$), 4.36 (t, N$^+$(CH$_2$CH$_2$)$_3$N$^+$), 4.51 and 5.13 (2d's, 2-CHaHb), 6.64 (d, Naphthosultam H-6), 7.40 (m, Naphthosultam H-3, H-5), 7.73 (d, Naphthosultam H-7), 8.08 (d, Naphthosultam H-2).

PREPARATIVE EXAMPLE 32
(1S,5R,6S)-6-(1(R)-HYDROXY-ETHYL)-1-METHYL-2-{6-(2-(4-(2-AMONIOETHYL)AMINOCARBONYLMETHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL}CARBAPEN-2-EM-3-CARBOXYLATE DICHLORIDE

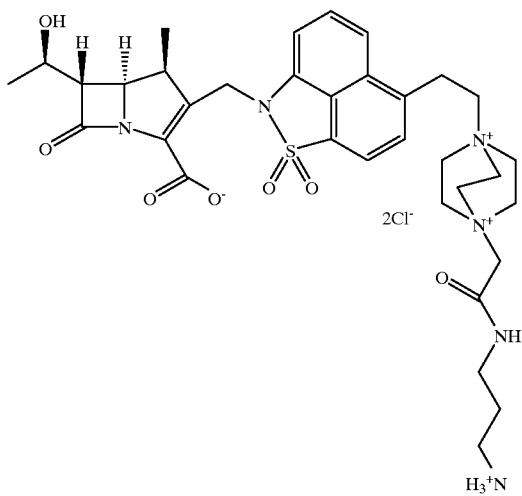

Starting with the product of Preparative Example 18, step 3 and following the procedure of steps 1 and 2 of Preparative Example 24 one obtains the title compound.

$^1$H NMR (D$_2$O:CD$_3$CN 10:1, 500 MHz) δ1.24 (d, 1-CH$_3$), 1.30 (d, C$\underline{H}_3$-CHOH), 3.20 (t, H-1), 3.26 (t, C$\underline{H}_2$CH$_2$NH$_2$) 3.47 (dd, H-5), 3.68 (t, CH$_2$N$\underline{H}_2$), 3.79 (m, CH$_2$C$\underline{H}_2$Ar), 4.03 (t, CH$_2$CH$_2$N$^+$), 4.11 (dd, H-6), 4.24 (t, C$\underline{H}$OH), 4.32 (t, N$^+$(C$\underline{H}_2$CH$_2$)$_3$N$^+$), 4.45 (t, N$^+$(CH$_2$C$\underline{H}_2$)$_3$N$^+$), 4.56 (s, C$\underline{H}_2$CONH), 4.67 and 5.37 (2d's, 2-CHaHb), 6.89 (d, Naphthosultam H-6), 7.62 (m, Naphthosultam H-3, H-5), 7.89 (d, Naphthosultam H-7), 8.16 (d, Naphthosultam H-2).

PREPARATIVE EXAMPLE 33
SYNTHESIS OF (1S,5R,6S)-2-(3-(2-[4-(3-AMMONIO-PROPYL)-1,4-DIAZONIA-BICYCLO[2.2.2]OCT-1-YL]-ETHYL}-1,8-NAPHTHOSULTAMYL-METHYL)-6-[(1R)-HYDROXY-ETHYL]-1-METHYL-CARBAPEN-2-EM-3-CARBOXYLATE DICHLORIDE

Step 1: Allyl (1S,5R,6S)-6-[(1R)-(allyloxycarbonyloxy)-ethyl]-2-(3-{2-[4-(3-azido-propyl)-1,4-diazonia-bicyclo[2.2.2]oct-1-yl]-ethyl}-1,8-naphthosultamyl-methyl)-1-methyl-carbapen-2-em-3-carboxylate bis (trifluorometianesulfonate)

A solution of allyl (1S,5R,6S)-6-[(1R)-(allyloxycarbonyloxy)-ethyl]-1-methyl-2-(3-[2-(trifluoromethanesulfonyloxy)-ethyl]-1,8-naphthosultamyl-methyl}-carbapen-2-em-3-carboxylate (0.141 mmol) in anhydrous acetonitrile (1.0 mL) was added to 1-(3-azido-propyl)-1-azonia-4-aza-biyclo[2.2.2]octane trifluoromethanesulfonate (51 mg, 0.144 mmol). The solution was concentrated under vacuum to approximately 0.2 mL and let stand at room temperature for 2 hours. The oil was triturated with diethyl ether, the solvent decanted, and the residue dried under vacuum to afford the title compound as an amorphous solid. It was used in the next step without further purification.

Step 2: (1S,5R,6S)-2-(3-{2-[4-(3-Ammonio-propyl)-1,4-diazonia-bicyclo[2.2.2]oct-1-yl]-ethyl}-1,8-naphthosultamyl-methyl)-6-[(1R)-hydroxy-ethyl]-1-methyl-carbapen-2-em-3-carboxylate dichloride A solution of crude allyl (1S,5R,6S)-6-[(1R)-(allyloxycarbonyloxy)-ethyl]-2-(3-{2-[4-(3-azido-propyl)-1,4-diazonia-bicyclo[2.2.2]oct-1-yl]-ethyl}-1,8-naphthosultamyl-methyl)-1-methyl-carbapen-2-em-3-carboxylate bis(trifluoromethanesulfonate) (0.141 mmol) in anhydrous dimethylformamide (1.4 mL) was treated with 5,5-dimethyl-1,3-cyclohexanedione (dimedone, 59 mg, 0.423 mmol), triphenylphosphine (5.5 mg, 0.021 mmol) and tetrakis(triphenylphosphine)palladium(0) (8.1 mg, 0.007 mmol). The mixture was placed under a nitrogen atmosphere, treated with N,N-diisopropylethylamine (0.074 mL, 0.423 mmol), and stirred at room temperature. After 20 minutes, the mixture was added to diethyl ether (13 mL) and centrifuged. The supernatant was decanted from the orange colored solid which was washed with more ether (14 mL) and dried under vacuum to afford crude (1S,5R,6S)-2-(3-{2-[4-(3-azido-propyl)-1,4-diazonia-bicyclo[2.2.2]oct-1-yl]-ethyl]-1,8-naphthosultamyl-methyl)-6-[(1R)-hydroxy-ethyl]-1-methyl-carbapen-2-em-3-carboxylate trifluromethanesulfonate.

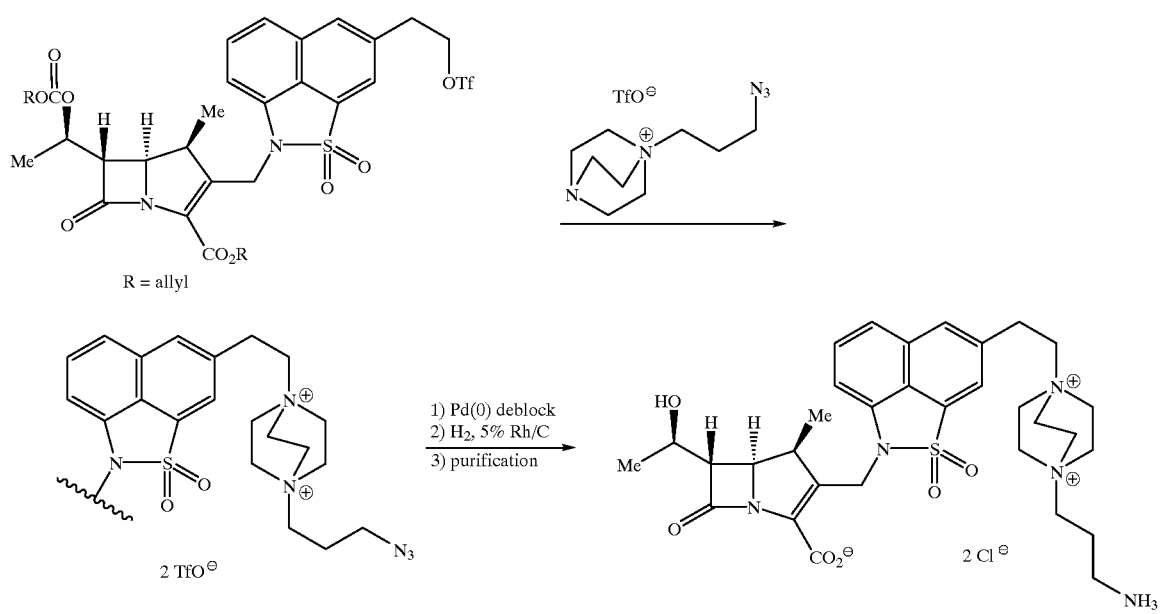

The deallylated product was dissolved in tetrahydrofuran (2 mL), water (4 mL) and ethanol (3 mL), treated with 5% rhodium on carbon (17 mg), and stirred under an atmosphere of hydrogen. After 65 minutes, the mixture was filtered and the filtrate applied to a column of Macro-Prep CM weak cation exchange resin (3 mL). The column was eluted with 1:1 acetonitrile-water (10 mL), water (12 mL), and 5% aqueous sodium chloride (40 mL). The saline fractions were concentrated under vacuum to 9 mL and loaded onto a Ranin Microsorb $C_{18}$ RP HPLC column (2×30 cm) which was gradiently eluted with acetonitrile in 0.12M aqueous ammonium chloride. The product containing fractions were concentrated under vacuum then applied to a column of Amberchrom CG-161 which was eluted with water (25 mL) followed by 20% isopropanol in water. The product eluted sharply with isopropanol-water. The product containing fractions diluted with water, concentrated under vacuum to 4 mL, and lyophilized to afford the title compound (36.5 mg) as a pale yellow, amorphous solid.

$^1$H NMR (D$_2$O) δ1.08 (d, 1-CH$_3$), 1.18 (d, C$\underline{H}_3$CHOH), 2.31 (m, CH$_2$C$\underline{H}_2$CH$_2$), 3.08 (dq, H-1), 3.14 (t, C$\underline{H}_2$NH$_3$), 3.38–3.42 (m, ArC$\underline{H}_2$CH$_2$N and H-6), 3.72–3.78 (m, NC$\underline{H}_2$CH$_2$CH$_2$NH$_3$), 3.87–3.94 (m, ArCH$_2$C$\underline{H}_2$N), 4.06 (dd, H-5), 4.11–4.23 (m, DABCO and CH$_3$C$\underline{H}$OH), 4.41 (d, 2-CH$\underline{a}$Hb), 4.75 (HOD), 5.07 (d, 2-CHaH$\underline{b}$), 6.38 (m, Ar H-7), 7.03 (m, Ar H-6 and Ar H-5), 7.77 and 7.86 (two s's, Ar H-2 and Ar H-4).

PREPARATIVE EXAMPLE 34
SYNTHESIS OF (1S,5R,6S)-6-[(1R)-HYDROXY-ETHYL]-1-METHYL-2-(3-(2-[4-(3-METHYLAMMONIO-PROPYL)-1,4-DIAZONIA-BICYCLO[2.2.2]OCT-1-YL]-ETHYL}-1,8-NAPHTHOSULTAMYL-METHYL)-CARBAPEN-2-EM-3-CARBOXYLATE DICHLORIDE

Step 1: Allyl (1S,5R,6S)-2-[3-(2-{4-[4-(allyloxycarbonyl]-4-aza-pent-1-yl]-1,4-diazonia-bicyclo[2.2.2]oct-1-yl}-ethyl)-1,8-naphthosultamyl-methyl]-6-[(1R)-(allyloxycarbonyloxy)-ethyl]-1-methyl-carbapen-2-em-3-carboxylate bis(trifluoromethanesulfonate)

A solution of allyl (1S,5R,6S)-6-[(1R)-(allyloxycarbonyloxy)-ethyl]-1-methyl-2-{3-[3-(trifluoromethanesulfonyloxy)-propyl]-1,8-naphthosultamyl-methyl}-carbapen-2-em-3-carboxylate (0.172 mmol) in anhydrous acetonitrile (0.9 mL) was treated with allyl N-[3-(4-aza-1-azonia-bicyclo[2.2.2]oct-1-yl)-propyl]-N-methyl-carbamate trifluoromethanesulfonate (76 mg, 0.188 mmol). The solution kept at room temperature for one hour then stored in a freezer at −10° C. for 3.5 days. The solvent was evaporated under vacuum. The residual oil was triturated with diethyl ether, the solvent decanted, and the residue dried under vacuum to afford the title compound as an amorphous solid. It was used in the next step without further purification.

Step 2: (1S,5R,6S)-6-[(1R)-Hydroxy-ethyl]-1-methyl-2-[3-{2-[4-(3-methylammonio-propyl)-1,4-diazonia-bicyclo[2.2.2]oct-1-yl]-ethyl}-1,8-naphthosultamyl-methyl)-carbapenem-2-em-3-carboxylate dichloride A solution of crude allyl (1S,5R,6S)-2-[3-(2-{4-[4-(allyloxycarbonyl]-4-aza-pent-1-yl]-1,4-diazonia-bicyclo[2.2.2]oct-1-yl}-ethyl)-1,8-naphthosultamyl-methyl]-6-[(1R)-(allyloxycarbonyloxy)-ethyl]-1-methyl-carbapen-2-em-3-carboxylate bis(trifluoromethanesulfonate) (0.172 mmol) and tetrakis(triphenylphosphine)palladium(0) (10.0 mg, 0.086 mmol) in anhydrous dimethylformamide (0.86 mL) was placed under a nitrogen atmosphere and treated with phenylsilane (0.191 mL, 1.55 mmol). After stirring for 20 minutes at room temperature, the dark solution was added to diethyl ether (12 mL) to give a brown precipitate. The supernatant was decanted and the residue dried under vacuum to give a solid (246 mg).

The solid was dissolved in 1:1 acetonitrile-water (3 mL) and applied to a column of Macro-Prep CM weak cation

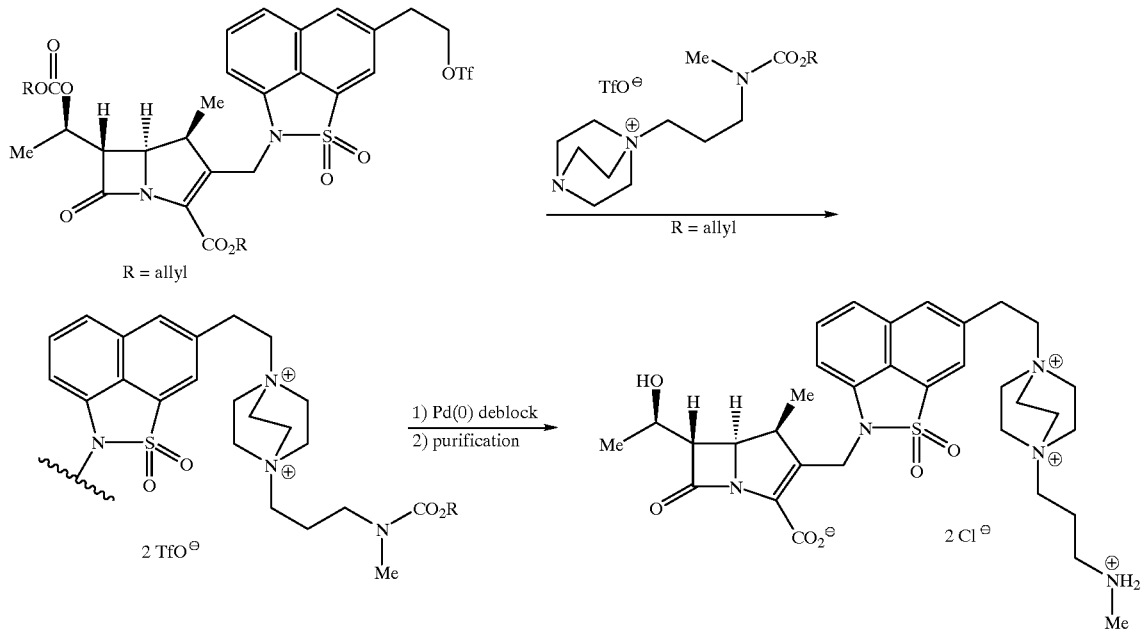

exchange resin (4 mL). The column was eluted with 1:1 acetonitrile-water (7 mL), water (18 mL), 5% aqueous NaCl (9 mL), and 1:1 isopropanol-10% aqueous NaCl (10 mL). The product containing fractions (5% NaCl and 1:1 iPrOH-10% NaCl) wre combined and concentrated under vacuum to remove isopropanol. The resulting solution was applied to a column of Amberchrom CG-161 resin (5 mL) which was eluted with water (20 mL) followed by 20% isopropanol in water (6 mL). The product containing fractions (20% iPrOH) were concentrated under vacuum, diluted with water, reconcentrated, filtered, and lyophilized to give a pale yellow, amorphous solid (43 mg). This material was further purified by HPLC on a Ranin Microsorb $C_{18}$ RP column (2×30 cm) which was gradiently eluted with acetonitrile (0–30%) in 0.12M aqueous ammonium chloride. The product containing fractions (30% MeCN in 0.12M $NH_4Cl$) were desalted on Amberchrom CG-161 (5 mL) as described above and the final aqueous solution lyophilized to provide the title compound (8.0 mg) as an amorphous, white solid.

$^1H$ NMR ($D_2O$) δ1.14 (d, 1-$CH_3$), 1.21 (d, C$\underline{H}$-$_3$CHOH), 2.33 (m, $CH_2C\underline{H}_2CH_2$), 2.76 (s, $NCH_3$), 3.17 (m, C$\underline{H}_2NH_2CH_3$), 3.41–3.45 (m, Ar$C\underline{H}_2CH_2N$, H-1, and H-6), 3.75 (m, $NC\underline{H}_2CH_2CH_2NH_2CH_3$), 3.93 (m, $ArCH_2C\underline{H}_2N$), 4.09 (dd, H-5), 4.1–4.3 (m, DABCO and $CH_3C\underline{H}OH$), 4.66 (d, 2-C$\underline{H}$aHb), 4.75 (HOD), 5.14 (d, 2-CHa$\underline{H}$b), 6.50 (m, Ar H-7), 7.17 (m, Ar H-5 and Ar H-6), 7.86 and 7.91 (two s's, Ar H-2 and Ar H-4).

PREPARATIVE EXAMPLE 35

SYNTHESIS OF 1-(3-AZIDO-PROPYL)-1,4-DIMETHYL-PIPERAZINIUM TRIFLUOROMETHANE-SULFONATE

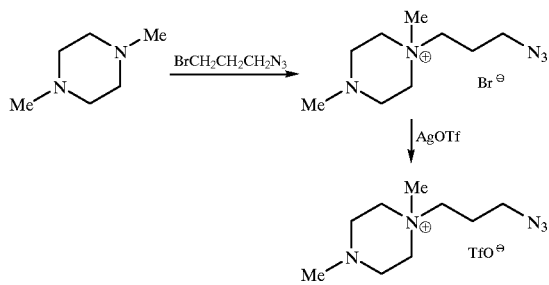

Step 1: 1-(3-Azido-propyl)-1,4-dimethyl-piperazinium bromide

A solution of 1,4-diemthyl-piperazine (0.81 mL, 6 mmol) in anhydrous acetonitrile (10 mL) was treated with 1-azido-3-bromo-propane (0.82 g, 5 mmol). The resulting mixture was srirred at room temperature for 16 hours and then diluted with diethyl ether (30 mL). The insoluble product was washed with ether and dried under vacuum to afford the title compound.

Step 2: 1-(3-Azido-propyl)-1,4-dimethyl-piperazinium trifluoromethanesulfonate

The crude bromide salt from step 1 (5 mmol) was dissolved in metrhanol (25 mL) and the solution was treated with silver trifluoromethanesulfonate (1.30 g, 4.89 mmol). The resulting mixture was stirred at room temperature and in the dark for 30 minutes. The mixture was filtered through a methanol washed pad of celite and the filtrate was evaporated under vacuum. The residue was triturated with diethyl ether and dried under vacuum to provide the title compound.

PREPARATIVE EXAMPLE 36

(1S,5R,6S)-6-(1(R)-HYDROXY-ETHYL)-1-METHYL-2-{6-(2-(4-(4-AMONIOMETHYLPHENYL) AMINOCARBONYL)METHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL) CARBAPEN-2-EM-3-CARBOXYLATE DICHLORIDE

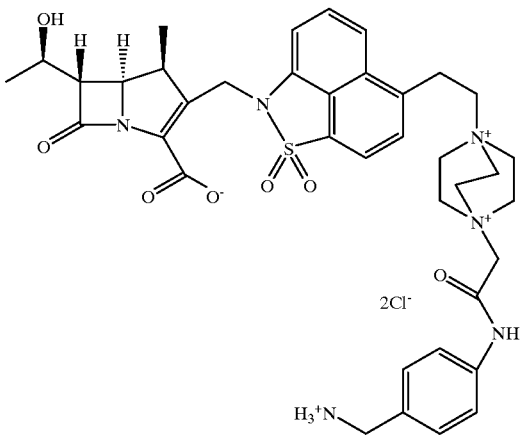

Step 1: Allyl (1S,5R,6S)--6-[(1R)-(allyloxycarbonyloxy)-ethyl]-1-methyl-2-[6-(2-(4-(4-azidomethylphenyl) aminocarbonyl)methyl)-1,4-diazonia-bicyclo[2.2.2]oct-1-yl)-ethyl)-1,1-dioxo-1H-1-thia-2-aza-acenaphthylen-2-yl-methyl]carbapen-2-em-3-carboxylate bis-trifluormethylsulfonate Starting with N-(4-azidomethylphenyl)-1-(4-aza-1-azonia-bicyclo[2.2.2]oct-1-yl)acetamide triflate (18.5 mg) from preparative example and reacting it with Allyl (1S,5R, 6S)--6-[(1R)-(allyloxycarbonyloxy)-ethyl]-2-[6-(2-trifluoromethanesulfonyloxyethyl)-ethyl]-1,1-dioxo-2H-1-thia-2-aza-acenaphthalen-2-yl-methyl}-1-methyl-carbapen-2-em-3-carboxylate (30 mg) from Step 4, Preparative Example 2, according to the procedure of Preparative Example 24, one obtains the title product, which is used in the next step without further purification.

Step 2. (1S,5R,6S)-6-(1(R)-hydroxy-ethyl)-1-methyl-2-[6-(2-(4-(4-amoniomethylphenyl)aminocarbonyl)methyl)-1,4-diazonia-bicyclo[2.2.2]oct-1-yl)-ethyl)-1,1-dioxo-1H-1-thia-2-aza-acenaphthylen-2-yl-methyl]carbapen-2-em-3-carboxylate dichloride The product from Step 1 was dissolved in DMF (0.2 ml), Phenylsilane (30 μl) was added, followed by tetrakis (triphenylphosphine) palladium(0) (2 mg). The reaction was stirred at room temperature for 15 min. then diluted with ether (2 ml) to precipitate the product. The ether solution was decanted off and the residue washed with 2×2 ml ether. The combined ether solutions were centrifuged and the precipitate combined with the original precipitate was dissolved in acetonitrile/water 1/1 (1 ml). This solution was applied to a column of Macro-Prep CM weak cation exchange resin (1.5 ml). The column was eluted with 1:1 acetonitrile-water (3 ml) followed by water (3 ml). The resin was eluted with 5% aqueous sodium chloride (6 ml) and collected in 1 ml fractions. The fractions containing the product were combined and treated with 5% rhodium on carbon (10 mg) and stirred under an atmosphere of hydrogen. After 1.5 hour more catalyst (5 mg) was added and the reduction continued for 1 hr. The catalyst was filtered off and the filtrate was loaded onto a Rainin Microsorb C18 RP HPLC column (2×30 cm). Gradient elution with acetonitrile/

0.12M aqueous ammonium chloride gave pure product containing fractions which were combined and concentrated under vacuum. The concentrated product was applied to a column of Amberchrome CG-161 1.5 ml) which was eluted with water (5 ml) followed by 1:1 acetonitrile-water (5 ml). The acetonitrile-water eluate was lyophilized to give the product (2.5 mg).

$^1$H NMR (D$_2$O, 500 MHz) δ1.13 (d, 1-CH$_3$), 1.19 (d, CH$_3$-CHOH), 3.07 (t, H-1), 3.39 (dd, H-5), 3.72 (t, CH$_n$Ar), 3.97 57 (t, CH$_2$CH$_2$N$^+$), 4.14 (s, CH$_2$—NH$_2$), 4.27 (t, N$^+$(CH$_2$CH$_2$),N$^+$), 4.44 (t, N$^+$(CH$_2$CH$_2$)$_3$N$^+$), 4.57 and 5.18 (2d's, 2-CHaHb), 6.74 (d, Naphthosultam H-6), 7.50 (m, Naphthosultam H-3, H-5 and Ph-H ), 7.78 (m, Naphthosultam H-7), 8.05 (d, Naphthosultam H-2).

PREPARATIVE EXAMPLE 37

(1S,5R,6S)-6-(1(R)-HYDROXY-ETHYL)-1-METHYL-2-{6-(2-(4-(4-(2-AMONIOETHYL)PHENYL) AMINOCARBONYL)METHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL}CARBAPEN-2-EM-3-CARBOXYLATE DICHLORIDE

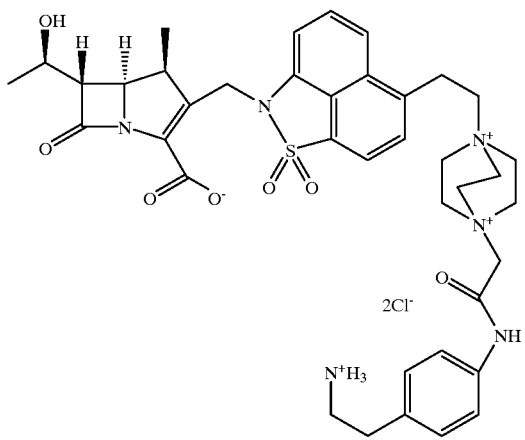

Starting with the product of Preparative example 16 and following the procedure of steps 1 and 2 of Preparative Example 36, one obtains the title compound.

$^1$H NMR (D$_2$O, 500 MHz) δ1.11 (d, 1-CH$_3$), 1.19 (d, CH$_3$-CHOH), 2.98 (m, CH$_2$CH$_2$NH$_2$), 3.45 (t, H-1), 3.66 (dd, H-5), 4.02 (t, CH$_n$Ar), 4.10 (t, CH$_2$CH$_2$NH$_2$), 4.23 (t, CH$_2$CH$_2$N$^+$), 4.38 (t, N$^+$(CH$_2$CH$_2$)$_3$N$^+$), 4.44 (t, N$^+$(CH$_2$CH$_2$)$_3$N$^+$), 4.98 (m, CHOH), 4.93 and 5.67 (2d's, 2-CHaHb), 7.23 (d, Naphthosultam H-6), 7.95 (m, Naphthosultam H-3, H-5), 8.09 and 8.28 (m, Ph-H), 8.14 (d, Naphthosultam H-7), 8.40 (d, Naphthosultam H-2).

PREPARATIVE EXAMPLE 38

(1S,5R,6S)-6-(1(R)-HYDROXY-ETHYL)-1-METHYL-2-{6-(2-(4-(2-(2-AMONIOETHYL)PHENYL) AMINOCARBONYL)METHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL}CARBAPEN-2-EM-3-CARBOXYLATE DICHLORIDE

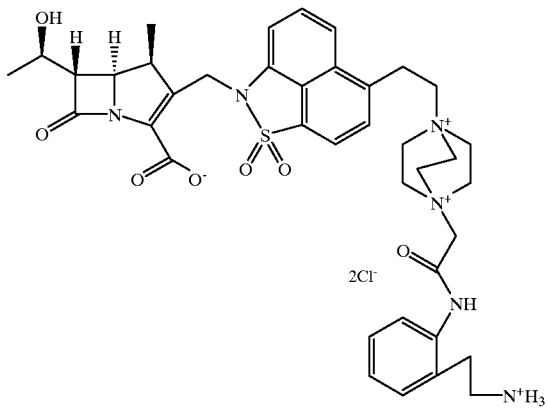

Starting with the product of Preparative example 20 and following the procedure of steps 1 and 2 of Preparative Example 36, one obtains the title compound.

1H NMR (D$_2$O, 500 MHz) δ1.12 (d, 1-CH$_3$), 1.19 (d, CH$_3$-CHOH), 2.95 (m, CH$_2$CH$_2$NH$_2$), 3.07 (t, H-1), 3.22 (t, CH$_2$CH$_2$NH$_2$), 3.39 (dd, H-5), 3.70 (t, CH$_2$Ar), 3.97 (t, H-6 and CH$_2$CH$_2$N$^+$), 4.12 (m, CHOH), 4.28 (t, N$^+$(CH$_2$CH$_2$)$_3$N$^+$), 4.45 (t, N$^+$(CH$_2$CH$_2$)$_3$N$^+$), 4.56 and 5.17 (2d's, CH$_2$C-2), 6.72 (d, Naphthosultam H-6), 7.34 (m, Naphthosultam H-3), 7.42 and 7.47 (m, Ph-H), 7.75 (d, Naphthosultam H-7), 8.03 (d, Naphthosultam H-2).

PREPARATIVE EXAMPLE 39

(1S,5R,6S)-6-(1(R)-HYDROXY-ETHYL)-1-METHYL-2-(6-(2-(4-(3-(2-AMONIOETHYL)PHENYL) AMINOCARBONYL)METHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL) CARBAPEN-2-EM-3-CARBOXYLATE DICHLORIDE

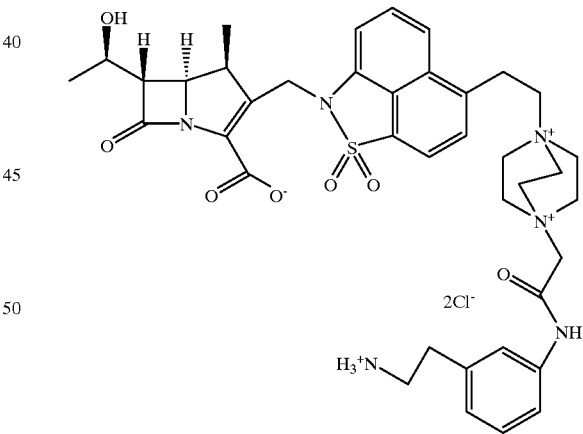

Starting with the product of Preparative example 19 and following the procedure of steps 1 and 2 of Preparative Example 36, one obtains the title compound.

$^1$H NMR (D$_2$O, 500 MHz) δ1.12 (d, 1-CH$_3$), 1.20 (d, CH$_3$-CHOH), 3.00 (m, CH$_2$CH$_2$NH$_2$), 3.05 (t, H-1), 3.27 (t, CH$_2$CH$_2$NH$_2$), 3.38 (dd, H-5), 3.71 (t, CH$_2$Ar), 3.96 (t, H-6 and CH$_2$CH$_2$N$^+$), 4.11 (m, CHOH), 4.28 (t, N$^+$(CH$_2$CH$_2$)$_3$N$^+$), 4.44 (t, N$^+$(CH$_2$CH$_2$),N$^+$), 4.54 and 5.16 (2d's, 2-CHaHb), 6.70 (d, Naphthosultam H-6), 7.21 (m, Naphthosultam H-3), 7.41–7.49 (m, Ph-H), 7.76 (d, Naphthosultam H-7), 8.03 (d, Naphthosultam H-2).

PREPARATIVE EXAMPLE 40
SYNTHESIS OF (1S,5R,6S)-2-{3-[2-(4-{[4-(2-AMMONIO-ETHYL)-PHENYLCARBAMOYL]-METHYL}-1,4-DIAZONIA-BICYCLO[2.2.2]OCT-1-YL)-ETHYL]-1,8-NAPHTHOSULTAMYL-METHYL}-6-[(1R)-HYDROXY-ETHYL]-1-METHYL-CARBAPENEM-2-EM-3-CARBOXYLATE DICHLORIDE

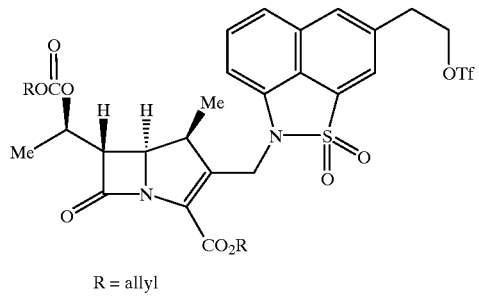

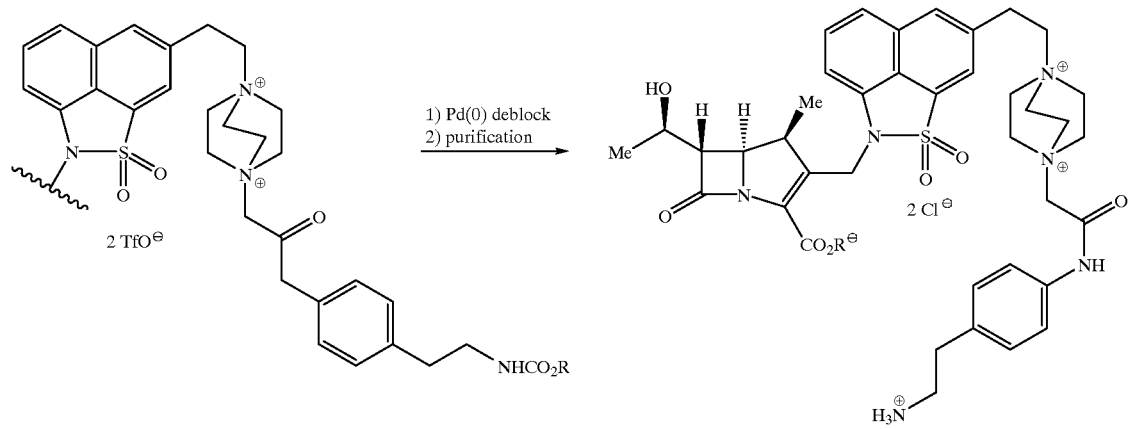

Step 1: Allyl (1S,5R,6S)-2-{3-[2-(4-{[4-(2-allyloxycarbonylamino-ethyl)-phenylcarbamoyl]-methyl}-1,4-diazonia-bicyclo[2.2.2]oct-1-yl)-ethyl]-1,8-naphthosultamyl-methyl}-6-[(1R)-allyloxycarbonyloxy-ethyl]-1-methyl-carbapenem-2-em-3-carboxylate bis(trifluoromethanesulfonate)

A solution of allyl (1S,5R,6S)-6-[(1R)-(allyloxycarbonyloxy)-ethyl]-1-methyl-2-{3-[3-(trifluoromethanesulfonyloxy)-propyl]-1,8-naphthosultamyl-methyl}-carbapen-2-em-3-carboxylate (0.172 mmol) in anhydrous acetonitrile (0.9 mL) was treated with allyl N-(2-{4-[2-(4-aza-1-azonia-bicyclo[2.2.2]oct-1-yl)-acetylamino]-phenyl}-ethyl)-carbamate trifluoromethanesulfonate (98 mg, 0.188 mmol). The solution kept at room temperature for one hour then stored in a freezer at −10° C. for 4.5 days. The solvent was evaporated under vacuum. The residual oil was triturated with diethyl ether, the solvent decanted, and the residue dried under vacuum to afford the title compound as a foam. It was used in the next step without further purification.

Step 2: (1S,5R 6S)-2-{3-[2-(4-{[4-(2-ammonio-ethyl)-phenylcarbamoyl]-methyl}-1,4-diazonia-bicyclo[2.2.2]oct-1-yl)-ethyl]-1,8-naphthosultamyl-methyl}-6-[(1R)-hydroxy-ethyl]-1-methyl-carbapenem-2-em-3-carboxylate dichloride A solution of crude allyl (1S,5R,6S)-2-{3-[2-(4-{[4-(2-allyloxycarbonylamino-ethyl)-phenylcarbamoyl]-methyl}-1,4-diazonia-bicyclo[2.2.2]oct-1-yl)-ethyl]-1,8-naphthosultamyl-methyl}-6-[(1R)-allyloxycarbonyloxy-ethyl]-1-methyl-carbapenem-2-em-3-carboxylate bis(trifluoromethanesulfonate) (0.172 mmol) and tetrakis(triphenylphosphine)palladium(0) (10.0 mg, 0.086 mmol) in anhydrous dimethylformamide (0.86 mL) was placed under a nitrogen atmosphere and treated with phenylsilane (0.191 mL, 1.55 mmol). After stirring for 20 minutes at room temperature, the solution was added to diethyl ether (13 mL) to give a precipitate. The supernatant was decanted and the solid residue dried under vacuum.

The solid was dissolved in 1:1 acetonitrile-water (3 mL) with added tetrahydrofuran (4 mL) and water (0.5 mL) and applied to a column of Macro-Prep CM weak cation exchange resin (2.5 mL). The column was eluted with 1:1 acetonitrile-water (7 mL), water (12 mL), and 1:1 isopropanol-10% aqueous NaCl (8 mL). The product containing fractions (1:1 iPrOH-10% NaCl) were concentrated under vacuum to a hazy suspension and applied to a column of Amberchrom CG-161 resin (4 mL). The column was eluted with water (15 mL) followed by 20% isopropanol in water (6 mL). The product containing fractions (20% iPrOH) were concentrated under vacuum and lyophilized to give the title compound as a white amorphous solid (53 mg).

$^1$H NMR (D$_2$O) δ1.00 (d, 1-CH$_3$), 1.14 (d, C$\underline{H}_3$CHOH), 2.95 (t, C$\underline{H}_2$CH$_2$NH$_3$), 3.01 (dq, H-1), 3.24 (t, CH$_2$C$\underline{H}_2$NH$_3$), 3.32 (dd, H-6), 3.43 (m, ArC$\underline{H}_2$CH$_2$N), 3.95 (m, ArCH$_2$C$\underline{H}_2$N), 3.99 (dd, H-5), 4.12 (m, CH$_3$C$\underline{H}$OH), 4.28 (m, DABCO), 4.35 (d, 2-CH$\underline{a}$Hb), 4.44 (m, DABCO), 4.63 (s, NC$\underline{H}_2$CONH), 4.75 (HOD), 5.06 (d, 2-CHaH$\underline{b}$), 6.37 (m, Ar H-7), 7.03 (m, Ar H-5 and Ar H-6), 7.29 and 7.42 (two d's, C$_6$H$_4$), 7.81 and 7.89 (two s's, Ar H-2 and Ar H-4).

EXAMPLE 1

(1S,5R,6S)--2-{6-[2-(4-(3-GUANIDINOPROPYL)-1,4-DIAZONIA-BICYCLO[2.2.2]OCT-1-YL)-ETHYL]-1,1-DIOXO-2-H-1-THIA-2-AZA-ACENAPHTHALEN-2-YL-METHYL}-6-[1(R)-HYDROXYETHYL]-1-METHYL-CARBAPEN-2-EM-3-CARBOXYLATE DICHLORIDE

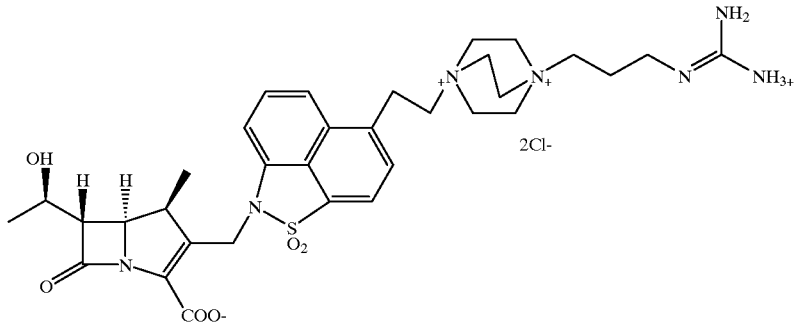

Step 1: Allyl (1S,5R,6S)--6-[(1R)-(allyloxycarbonyloxy)-ethyl]-2-{6-[2-(4-(3-N,N-diallyloxycarbonylguanidinopropyl)-1,4-diazonia-bicyclo[2.2.2]oct-1-yl]-ethyl-1,1-dioxo-2-H-1-thia-2-aza-acenaphthalen-2-yl-methyl}-1-methyl-carbapen-2-em-3-carboxylate bis (trifluoromethanesulfonate)

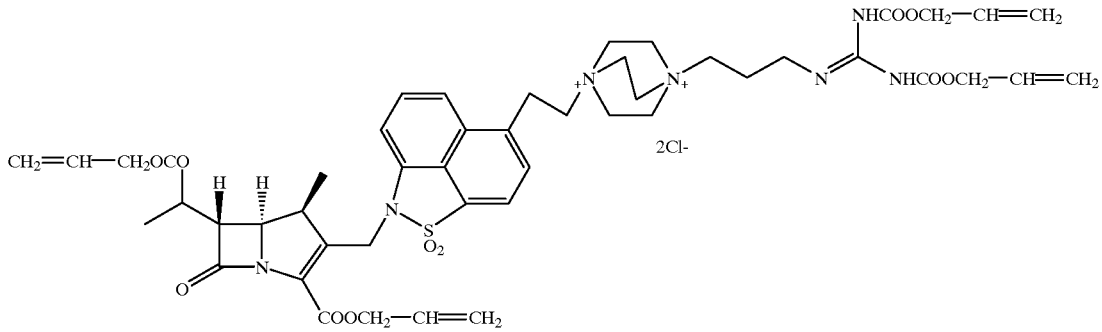

Allyl (1S,5R,6S)--6-[(1R)-(allyloxycarbonyloxy)-ethyl]-2-[6-(2-trifluoromethanesulfonyloxyethyl)-ethyl]-1,1-dioxo-2H-1-thia-2-aza-acenaphthalen-2-yl-methyl}-1-methyl-carbapen-2-em-3-carboxylate from Step 4, Preparative Example 2, (30 mg, 0.041 mmol) was dissolved in acetonitrile (0.5 ml), 3-(N,N-diallyloxycarbonylguanidino-1(1,4-diazoniabicyclo[2.2.2]oct-1-yl)-propane trifluoromethanesulfonate (31 mg, 0.049 mmol) from Step 3, Preparative Example 12, was added. The reaction was stirred 5 min. and the solvent was evaporated under vacuum to give a thick oil which was stirred at room temperature for 1 hr. The residual solvent was removed to give the product which was used in the next step without purification.

Step 2: (1S,5R,6S)--2-{6-[2-(4-(3-guanidiniopropyl)-1,4-diazonia-bicyclo[2.2.2]oct-1-yl)-ethyl]-1,1-dioxo-2-H-1,1-thia-2-aza-acenaphthalen-2-yl-methyl}-6-[1(R)-hydroxyethyl]-1-methyl-carbapen-2-em-3-carboxylate dichloride The product from Step 1 was dissolved in DMF (0.2 ml), Phenylsilane (30 μl, 0.24 mmol) was added, followed by tetrakis((triphenylphosphine) palladium(0) (4 mg, 0.0034 mmol). The reaction was stirred at room temperature for 10 min. then diluted with ether (3 ml) to precipitate the product. The ether solution was decanted off and the residue washed with 2×3 ml ether. The combined ether solutions were centrifuged and the precipitate combined with the original precipitate was dissolved in acetonitrile/water 1/1 (1.0 ml). This solution was applied to a column of Macro-Prep CM weak cation exchange resin (0.5 ml). The column was eluted with 1:1 acetonitrile-water (2 ml) followed by water (2 ml). The resin was eluted with 5% aqueous sodium chloride (16 ml). The eluate containing the product was loaded onto a Rainin Microsorb C18 RP HPLC column (2×30 cm). Gradient elution with acetonitrile/0.12M aqueous ammonium chloride gave pure product containing fractions which were combined and concentrated under vacuum. The concentrated product was applied to a column of Amberchrome CG-161, 1 ml) which was eluted with water (3 ml) followed by 1:1 acetonitrile-water (10 ml). The acetonitrile-water eluate was lyophilized to give the product (2 mg).

$^1$H NMR (D$_2$O, 500 MHz) δ1.13 (d, 1-CH$_3$), 1.20 (d, C<u>H</u>$_3$CHOH), 2.19 (m, CH$_2$C<u>H</u>$_2$CH$_2$), 3.09 (m, H-1), 3.37 (t, CH$_2$NH$_3$$^+$), 3.4 (d of d, H-6), 3.71 (m, ArC<u>H</u>$_2$CH$_2$), 3.96 (t, CH$_2$CH$_2$C<u>H</u>$_2$N$^+$), 4.0 (d of d, H-5), 4.13 (m, CH$_3$C<u>H</u>OH and $^+$N(C<u>H</u>$_2$CH$_2$)$_3$N$^+$), 4.23 (m, $^+$N(CH$_2$C<u>H</u>$_2$)$_3$N$^+$), 4.56 (d, 2-C<u>H</u>aHb), 5.18 (d, 2-CHaH<u>b</u>), 6.75 (d, ArH), 7.5 (m, ArH), 7.77 (d, ArH), 8.03 (d, ArH).

EXAMPLE 2

(1S,5R,6S)-6-(1(R)-HYDROXY-ETHYL)-1-METHYL-2-{6-(2-(4-(3-GUANIDINIUMPROPYL)AMINOCARBONYLMETHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL}CARBAPEN-2-EM-3-CARBOXYLATE DICHLORIDE

113

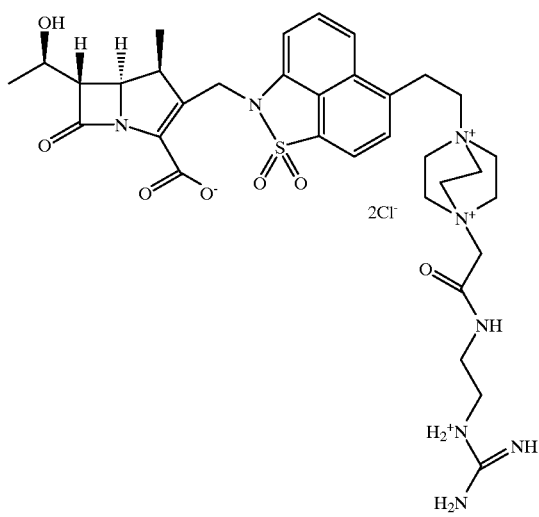

114

Starting with the product of Preparative Example 22 and following the procedure of steps 1 and 2 of Example 1, one obtains the title compound.

$^1$H NMR (D$_2$O, 500 MHz) δ1.09 (d, 1-CH$_3$), 1.19 (d, CH$_3$-CHOH), 3.04 (m, H-1), 3.38 and 3.47 (2t's, NHCH$_2$CH$_2$NH), 3.65 (m, CH$_2$Ar), 3.94 (m, H-5 and CH$_2$CH$_2$N$^+$), 4.11 (m, H-6), 4.15 (m, CHOH), 4.25 (t, N$^+$(CH$_2$CH$_2$)$_3$N$^+$), 4.36 (t, N$^+$(CH$_2$CH$_2$)$_3$N$^+$), 4.45 (s, CH$_2$CO), 4.51 and 5.14 (2d's, 2-CHaHb), 6.64 (d, Naphthosultam H-6), 7.34–7.40 (m, Naphthosultam H-3, H-5), 7.71 (d, Naphthosultam H-7), 7.98 (d, Naphthosultam H-2).

EXAMPLE 3

SYNTHESIS OF (1S,5R,6S)-2-(4-{2-[4-(3-FORMIMIDINIOAMINO-PROPYL)-1,4-DIAZONIA-BICYCLO[2.2.2]OCT-1-YL]-ETHYL}-1,8-NAPHTHOSULTAMYL-METHYL)-6-[(1R)-HYDROXY-ETHYL]-1-METHYL-CARBAPENEM-2-EM-3-CARBOXYLATE DICHLORIDE

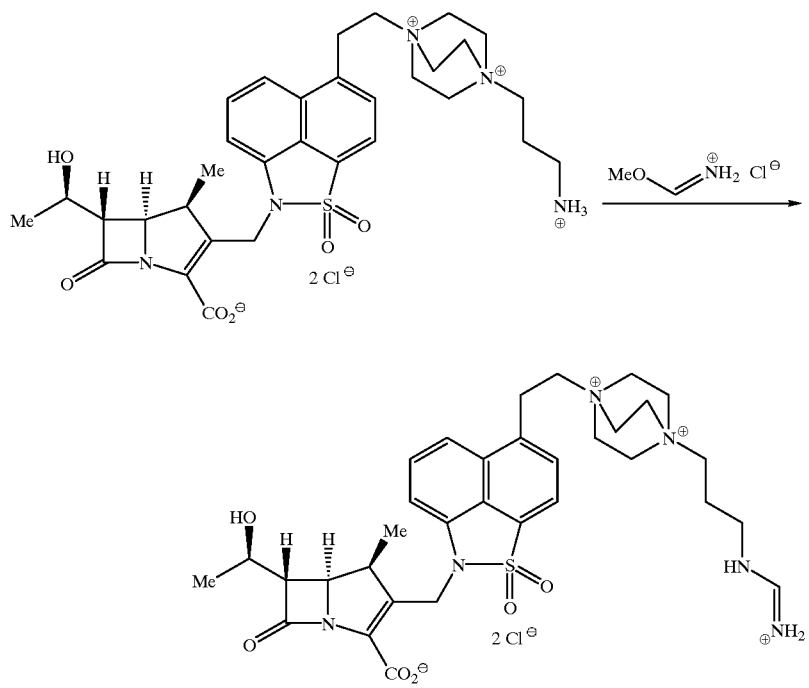

A solution of (1S,5R,6S)-2-(4-(2-[4-(3-ammonio-propyl)-1,4-diazonia-bicyclo[2.2.2]oct-1-yl]-ethyl]-1,8-naphthosultamyl-methyl)-6-[(1R)-hydroxy-ethyl]-1-methyl-carbapenem-2-em-3-carboxylate dichloride (21 mg, 0.03 mmol) from Preparative Example 24 in 0.1M pH 7.0 phosphate buffer (2.0 mL) was cooled in an ice-bath and stirred. The pH was brought to 8.5 by careful addition of 1N sodium hydroxide solution and, at pH 8.5, the solution was treated with methyl formimidate hydrochloride (44 mg, 0.46 mmol). The pH was readjusted to 8.5 and, after 3 minutes, treated with more methyl formimidate hydrochloride (40 mg, 0.42 mmol). The pH was again brought to 8.5 and the reaction mixture was stirred in the cold for 10 minutes. The mixture was brought to pH 7.0 by addition of 1N hydrochloric acid and then added to a column of Amberchrom CG-161 resin (0.9×8 cm). The column was eluted with water (16 mL) followed by 20% aqueous isopropanol. The product eluted sharply in the first 5 mL of aqueous isopropanol. The product containing fractions were diluted with water, concentrated under vacuum to remove isoprpanol, and lyophilized to provide the title compound (7.2 mg) as an amorphous solid.

Following the above procedure and starting with the products of Preparative Examples 24 to 34. one obtains the formamidinium compounds listed in Tables I–III.

EXAMPLE 4

(1S,5R,6S)-6-(1(R)-HYDROXY-ETHYL)-1-METHYL-2-{6-(2-(4-((PYRID-2-IUM)AMINOCARBONYL)METHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL}CARBAPEN-2-EM-3-CARBOXYLATE DICHLORIDE

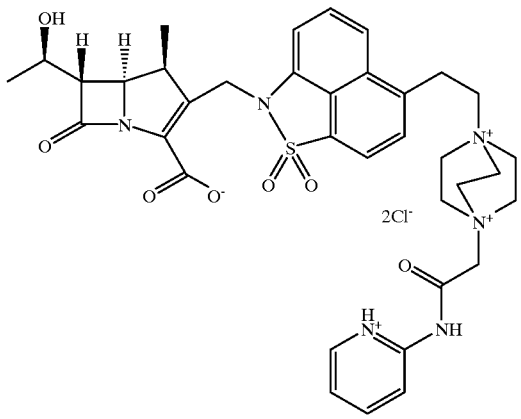

Starting with the product of Preparative example and following the procedure of steps 1 and 2 of Example one obtains the title compound.

$^1$H NMR (D$_2$O: CD$_3$CN 2:1, 500 MHz) δ1.40 (d, 1-CH$_3$), 1.43 (d, CH$_3$CHOH), 3.36 (t, H-1), 3.58 (dd, H-5), 3.95 (m, CH$_2$—Ar), 4.17 (m, CH$_2$CH$_2$—N$^+$), 4.26 (dd, H-6), 4.38 (t, CH—OH), 4.44 and 4.62 (2 t's, N$^+$(CH$_2$CH$_2$)$_3$N$^+$), 4.84 and 5.58 (2d's, CH$_2$—C2), 7.14 (d, Naphthosultam H-6), 7.53 (t, Py C4–H), 7.85 (m, Naphthosultam H-3 and H-6), 8.06 (d, Naphthosultam H-7), 8.11 and 8.15 (m, Py H-3 and H-5), 8.33 (d, Naphthosultam H-2), 8.58 (d, Py H-6).

EXAMPLE 5

(1S,5R,6S)-6-(1(R)-HYDROXY-ETHYL)-1-METHYL-2-{6-($^2$-($^4$-(($^2$-METHYLPYRID-2-IUM)AMINOCARBONYL)METHYL)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL}CARBAPEN-2-EM-3-CARBOXYLATE DICHLORIDE

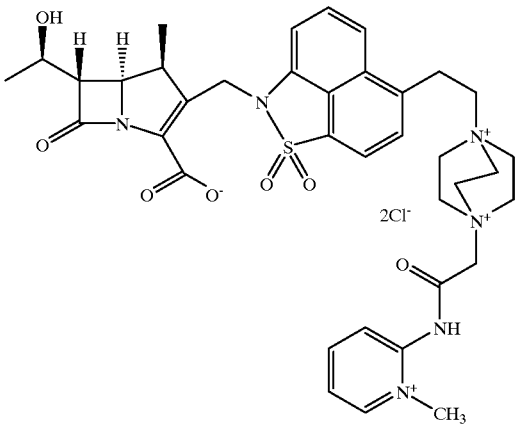

Starting with the product of Preparative example 14 and following the procedure of steps 1 and 2 of Example 1, one obtains the title compound.

$^1$H NMR (D$_2$O, 500 MHz) δ1.06 (d, 1-CH$_3$), 1.17 (d, CH$_3$—CHOH), 2.98 (t, H-1), 3.34 (dd, H-5), 3.66 (m, CH$_2$—Ar), 3.92 (m, ArCH$_2$CH$_2$—N$^+$), 3.94 (s, CH$_3$N$^+$), 4.09 (dd, H-6), 4.28 (t, N$^+$(CH$_2$CH$_2$)$_3$N$^+$), 4.45 (m, N$^+$(CH$_2$CH$_2$)$_3$N$^+$ and CHOH), 5.08 (d, 2-CHaHb), 6.59 (d, Naphthosultam H-6), 7.22 (t, Py H-3), 7.33 and 7.40 (m, Naphthosultam H-3 and H-5), 7.75 (m, Py C4-H and H-5), 7.98 (d, Naphthosultam H-7), 8.05 (d, Py H-6), 8.23 (d, Naphthosultam, H-2).

EXAMPLE 6

(1S,5R,6S)-6-(1(R)-HYDROXY-ETHYL)-1-METHYL-2-{6-(2-(4-(PYRROLIDIN-3-IUM)-1,4-DIAZONIA-BICYCLO[2.2.2]OCT-1-YL)-ETHYL)-1,1-DIOXO-1H-1-THIA-2-AZA-ACENAPHTHYLEN-2-YL-METHYL}CARBAPEN-2-EM-3-CARBOXYLATE DICHLORIDE

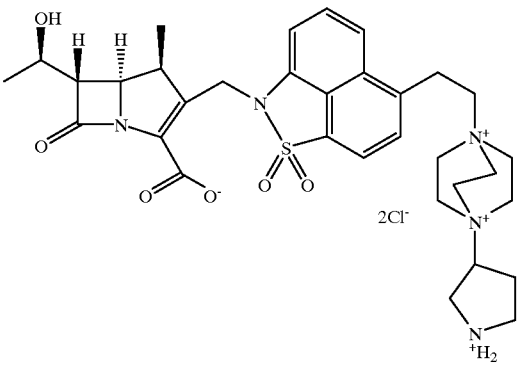

Starting with the product of Preparative example 21 and following the procedure of steps 1 and 2 of Example 1, one obtains the title compound.

$^1$H NMR (D$_2$O, 500 MHz) δ1.09 (d, 1-CH$_3$), 1.19 (d, CH$_3$—CHOH), 2.36 and 2.50 (m, CH$_2$CH$_2$NH), 3.04 (m, H-1), 3.18 (m, CHCH$_2$NH), 3.37 (t, H-5), 3.59 (m, CH$_2$NHCH$_2$) 3.67 (m, CH$_2$Ar), 3.90 (m, H-6), 3.95 (m, CH$_2$CH$_2$N$^+$), 4.16 (t, N$^+$(CH$_2$CH$_2$)$_3$N$^+$), 4.23 (t, N$^+$(CH$_2$CH$_2$)$_3$N$^+$), 4.53 and 5.15 (2d's, 2-CHaHb), 6.67 (d, Naphthosultam H-6), 7.43 (m, Naphthosultam H-3, H-5), 7.74 (d, Naphthosultam H-7), 8.01 (d, Naphthosultam H-2).

EXAMPLE 7
SYNTHESIS OF (1S,5R,6S)-2-(4-{2-[4-(3-FORMIMIDINIOAMINO-PROPYL)-1,4-DIMETHYL-PIPERAZIN-1-IO]-ETHYL}-1,8-NAPHTHOSULTAMYL-METHYL)-6-[(1R)-HYDROXY-ETHYL]-1-METHYL-CARBAPENEM-2-EM-3-CARBOXYLATE DICHLORIDE

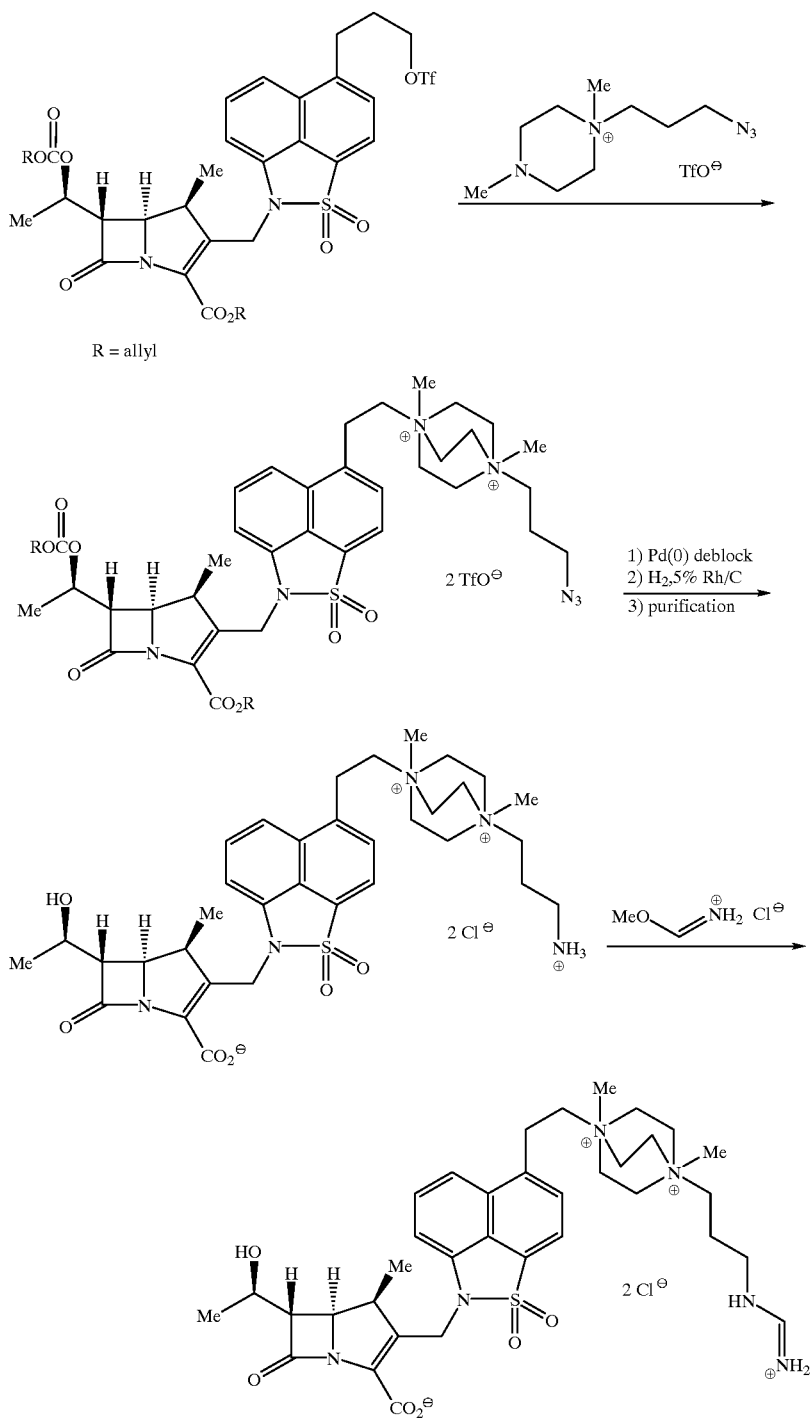

Step 1: Allyl (1S,5R,6S)-6-[(1R)-allyloxycarbonyloxy-ethyl]-2-(4-[2-[4-(3-azido-propyl)-1,4-dimethyl-piperazin-1-iol -ethyl}-1,8-naphthosultamyl-methyl)-1-methyl-carbapen-2-em-3-carboxylyate bis(trifluoromethanesulfonate)

A solution of allyl (1S,5R,6S)-6-[(1R)-(allyloxycarbonyloxy)-ethyl]-1-methyl-2-{4-[2-(trifluoromethanesulfonyloxy)-ethyl]-1,8-naphthosultamyl-methyl}-carbapen-2-em-3-carboxylate (0.125 mmol) in anhydrous acetonitrile (1.0 mL) was added to 1-(3-azido-propyl)-1,4-dimethyl-piperazinium trifluoromethane-sulfonate (52 mg, 0.15 mmol). The solution was stirred at room temperature for 90 minutes, then evaporated under vacuum and the residue stored at room temperature for an additional 90 minutes. The gum was triturated with three portions of diethyl ether to afford the title compound as an insoluble residue. This material was used in the next step without further purification.

Step 2: (1S,5R,6S)-2-{4-[2-[4-(3-Ammonio-propyl)-1,4-dimethyl-piperazin-1-io]-ethyl}-1,8-naphthosultamyl-methyl)-6-[(1R)-hydroxy-ethyl]-1-methyl-carbapen-2-em-3-carboxylate dichloride Crude allyl (1S,5R,6S)-6-[(1R)-allyloxycarbonyloxy-ethyl]-2-(4-{2-[4-(3-azido-propyl)-1,4-dimethyl-piperazin-1-iol -ethyl}-1,8-naphthosultamyl-methyl)-1-methyl-carbapen-2-em-3-carboxylate bis(trifluoromethanesulfonate) (0.125 mmol), 5,5-dimethyl-1,3-cyclohexanedione (dimedone, 53 mg, 0.378 mmol), triphenylphosphine (4.9 mg, 0.019 mmol) and tetrakis(triphenylphosphine)palladium(0) (7.2 mg, 0.006 mmol) were dissolved in anhydrous dimethylformamide (1.3 mL). The mixture was placed under a nitrogen atmosphere, treated with N,N-diisopropylethylamine (0.065 mL, 0.373 mmol), and stirred at room temperature. After 15 minutes, the mixture was added to diethyl ether (10 mL) and centrifuged. The insoluble portion was washed with more diethyl ether (10 mL) and dried under vacuum to afford crude (1S,5R,6S)-2-(4-{2-[4-(3-azido-propyl)-1,4-dimethyl-piperazin-1-io]-ethyl}-1,8-naphthosultamyl-methyl)-6-[(1R)-hydroxy-ethyl]-1-methyl-carbapen-2-em-3-carboxylate trifluromethanesulfonate.

The deallylated product was dissolved in tetrahydrofuran (2 mL), water (4 mL) and ethanol (3 mL), treated with 5% rhodium on carbon (15 mg), and stirred under an atmosphere of hydrogen. After two hours, the mixture was filtered and the filtrate applied to a column of Macro-Prep CM weak cation exchange resin (3 mL). The column was eluted with 1:1 acetonitrile-water (10 mL), water (15 mL), and 5% aqueous sodium chloride (40 mL). The product containing NaCl fractions were cooled in an ice bath and then loaded onto a column of Amberchrom CG-161 resin (4 mL). The column was eluted with ice-cold water (20 mL) followed by 20% isopropanol in water. The product eluted with isopropanol-water. The product containing fractions were diluted with water, concentrated under vacuum to remove the isopropanol, and lyophilized to afford the title compound as an amorphous solid.

Step 3: (1S,5R,6S)-2-(4-55 2-[4-(3-Formimidinioamino-propyl)-1,4-dimethyl-piperazin-1-io]-ethyl]-1,8-naphthosultamyl-methyl)-6- [(1R)-hydroxy-ethyl]-1-methyl-carbapen-2-em-3-carboxylate dichloride A solution of (1S,5R,6S)-2-(4-{2-[4-(3-ammonio-propyl)-1,4-dimethyl-piperazin-1-io]-ethyl}-1,8-naphthosultamyl-methyl)-6-[(1R)-hydroxy-ethyl]-1-methyl-carbapen-2-em-3-carboxylate dichloride (35 mg, 0.05 mmol) in 0.1M pH 7.0 phosphate buffer (3.5 mL) was cooled in an ice-bath and stirred. The pH of the solution was brought to 8.5 by careful addition of 1N sodium hydroxide solution. Methyl formimidate hydrochloride (143 mg, 1.5 mmol) was added in three portions over a period of 5 minutes, care being taken to maintain the pH at 8.5 by addition of more 1N sodium hydroxide. After stirring an additional 10 minutes at 0° C., the rection mixture was brought to pH 7.0 by addition of 1N hydrochloric acid and then added to a column of Amberchrom CG-161 resin (3 mL). The column was eluted with water (15 mL) followed by 20% aqueous isopropanol. The product was eluted with aqueous isoprpanol. The product containing fractions were diluted with water, concentrated under vacuum to remove isopropanol, and lyophilized to afford the title compound as an amorphous solid.

What is claimed is:

1. A compound represented by formula I:

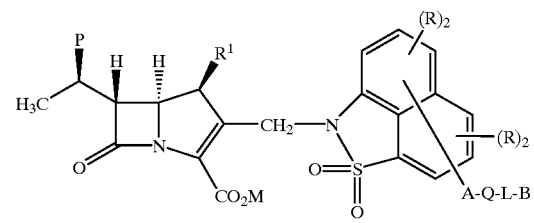

or a pharmaceutically acceptable salt thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

A-Q-L-B represents a side chain wherein:

A is a $C_{1-6}$ alkylene group, straight or branched, and optionally interrupted or terminated by 1–2 of —O—, —S—, $NR^a$—, —C(O)— and —CH=CH—;

Q is

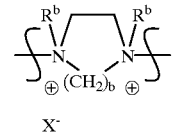

in which:

a is 1, 2 or 3;

b is 2 or 3;

and $X^-$ is a charge balancing counterion;

L represents a bond or a $C_{1-8}$ alkylene group, unsubstituted or substituted with 1–3 $R^c$ groups, uninterrupted, interrupted or terminated by 1–3 of —CH=CH—, —C(O)—, —C(O)$NR^d$—, —Het($R^e$)—, —C(O)—Het($R^e$)—, —C(O)$NR^a$—Het($R^e$)—, —O—, —S—, —S(O)—, —$SO_2$—, —$CO_2$—, —$NR^a$—, —$N^+(R^a)_2$—, Het is a heteroaryl group;

B represents a member selected from the group consisting of:

1) 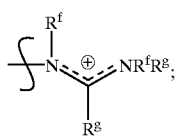

2) 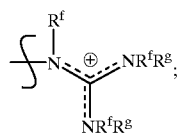

3) 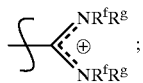

4) a 4–7 membered, N-containing heterocycle selected from:

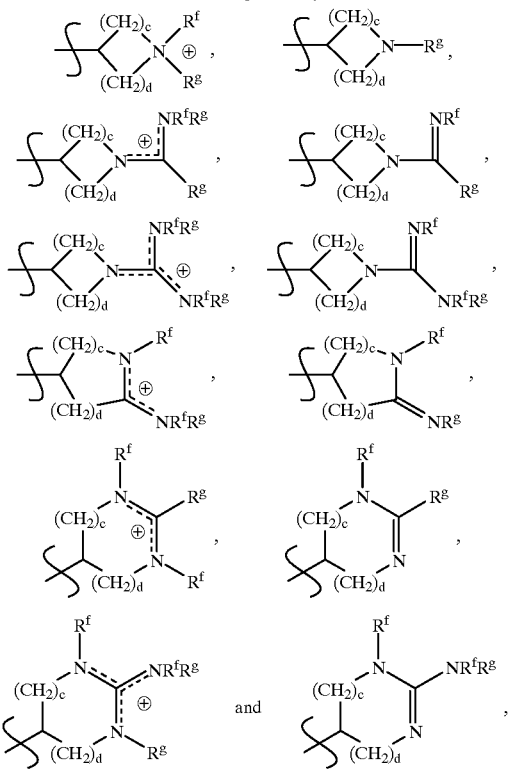

wherein c and d are independently 0–4, such that c+d equals from 2–5, and said heterocycle is optionally substituted on carbon atoms with 1–2 $R^f$ or $R^g$ groups, and is optionally interrupted by O, S, $NR^f$ or $NR^g$;

5) 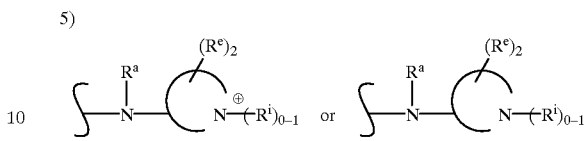

wherein

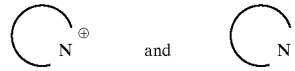

represent quaternary and non-quaternary 5–10 membered mono- or bicyclic, N-containing heteroaryl groups, respectively, optionally containing 1–4 additional heteroatoms selected from O, S and N;

6) 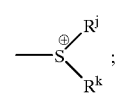

$R^a$ is H or $C_{1-6}$ alkyl;

$R^b$ is independently selected from $NH_2$ and $C_{1-6}$ alkyl unsubstituted or substituted with 1–3 groups selected from halo, OH, CN and $C(O)NH_2$;

$R^c$ is independently selected from halo, $OR^a$, $SR^a$, $OC(O)R^a$, $CO_2R^a$, CN, $C(O)N(R^a)_2$ and $C(O)R^a$, $R^d$ is H or $C_{1-3}$ alkyl, or $R^c$ and $R^d$ taken together with any intervening atoms represent a 4–6 membered ring;

$R^e$ is H; $R^c$; $NO_2$, $N(R^a)_2$, $SO_2N(R^a)_2$ or $C_{1-4}$ alkyl, unsubstituted or substituted with 1–3 groups selected from halo, OH and $C(O)NH_2$ $R^f$, $R^g$ and $R^h$ are independently selected from H; $C_{1-6}$ straight or branched chain alkyl, unsubstituted or substituted with 1–3 $R^c$ groups; $C_{3-6}$ cycloalkyl, unsubstituted or substituted with 1–3 $R^c$ groups; phenyl, unsubstituted or substituted with 1–3 $R^e$ groups and Het, unsubstituted or substituted with 1–3 $R^e$ groups, or $R^f$ and $R^g$ taken together with the intervening N atom form a 4–6 membered ring, optionally interrupted by 1–2 of O, S, C(O) or $NR^h$, and optionally substituted by 1–3 $R^c$ groups;

$R^i$ is H or $R^b$;

$R^j$ and $R^k$ are $C_{1-4}$ alkyl or $R^j$ and $R^k$ taken together with the intervening S atom are a 5–6 membered ring;

and each R independently represents H; $R^c$; $NO_2$; $N(R^a)_2$; $SO_2N(R^a)_2$ or $C_{1-4}$ alkyl, unsubstituted or substituted with 1–3 groups selected from halo, OH and $C(O)NH_2$, or R together with A of the group -A-Q-L-B and any intervening atoms represent a 5–6 membered carbocyclic ring.

2. A compound in accordance with claim 1 wherein $R^1$ represents methyl.

3. A compound in accordance with claim 1 wherein $CO_2M$ represents a carboxylate anion.

4. A compound in accordance with claim 1 wherein P represents hydroxyl or hydroxyl protected by a hydroxyl protecting group.

5. A compound in accordance with claim 1 wherein A represents $C_{1-3}$ alkylene.

6. A compound in accordance with claim 1 wherein L is a bond or $C_{1-5}$ alkylene, optionally interrupted or terminated by —C(O)NR$^d$—, —C(O)NR$^a$—Het(R$^e$)—, —NR$^a$—, —N$^+$(R$^a$)$_2$ or

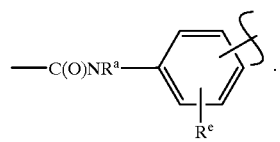

7. A compound in accordance with claim 1 wherein B is selected from:

1) 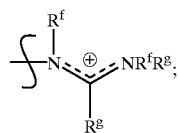

2) 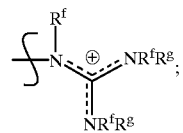

3) 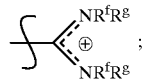

4) a 4–7 membered, N-containing heterocycle selected from

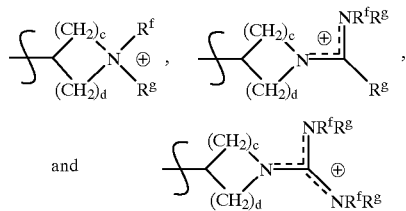

wherein c and d independently 0–4, such that c+d equals from 2–4, and said heterocycle is optionally substituted on carbon atoms with 1–2 $R^f$ or $R^g$ groups, and is optionally interrupted by $NR^f$ or $NR^g$;

and

5)

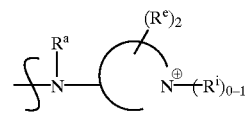

wherein

represents a quaternary 5–10 membered mono- or bicyclic, N-containing heteroaryl group, optionally containing 1–4 additional heteroatoms selected from O, S and N.

8. A compound represented by one of Tables I–III

TABLE I
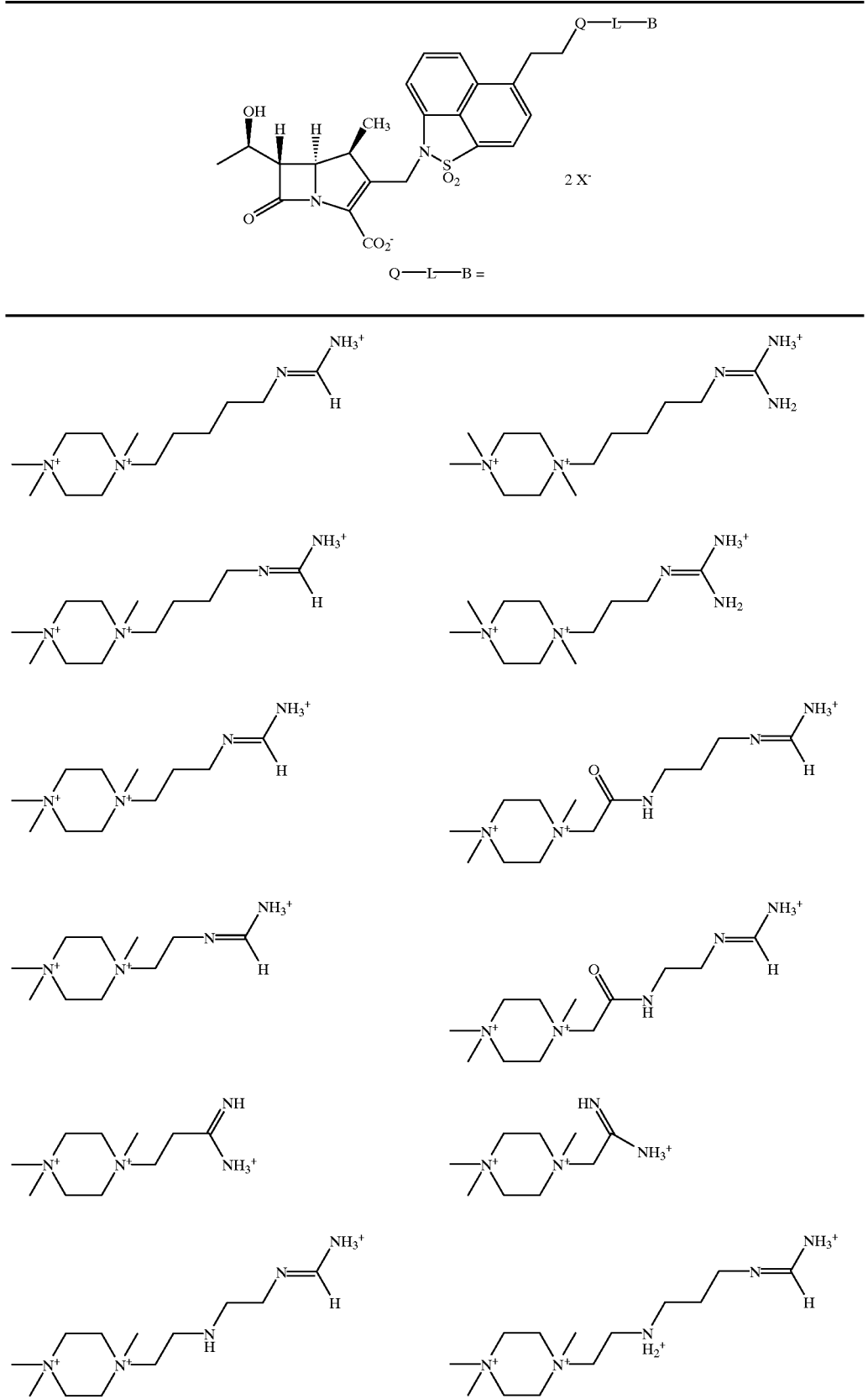

TABLE I-continued
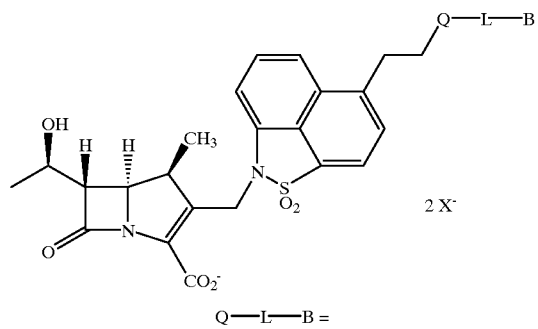
2 X⁻
Q—L—B =
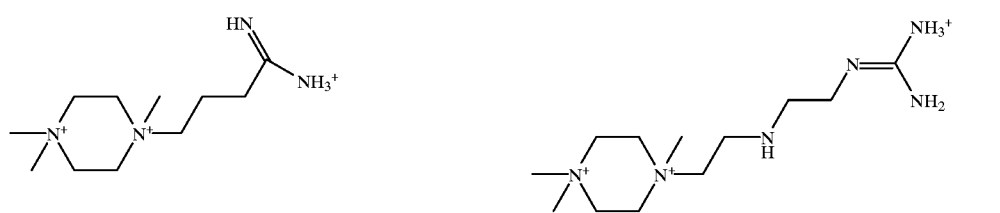
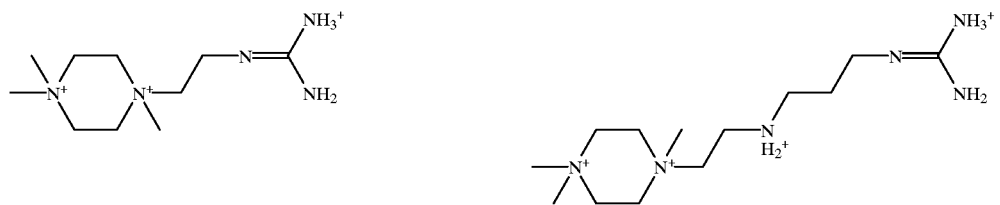
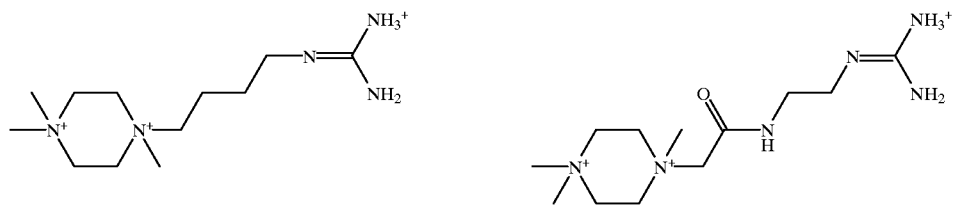
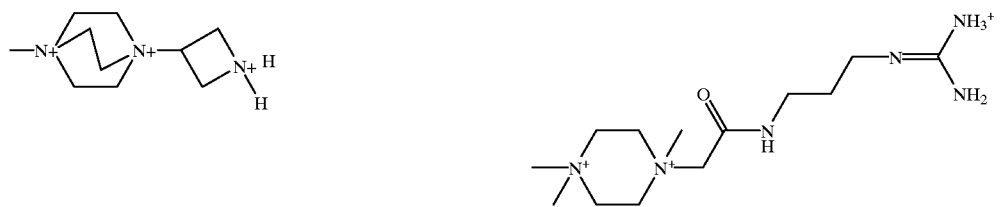
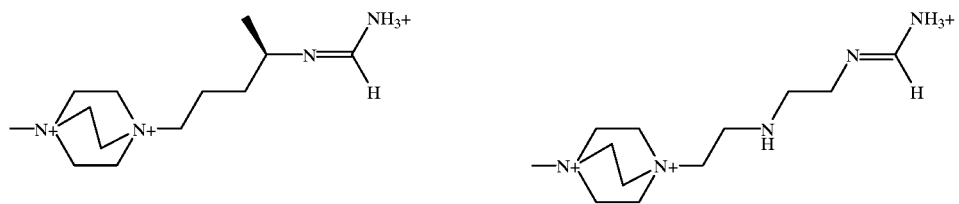

TABLE I-continued
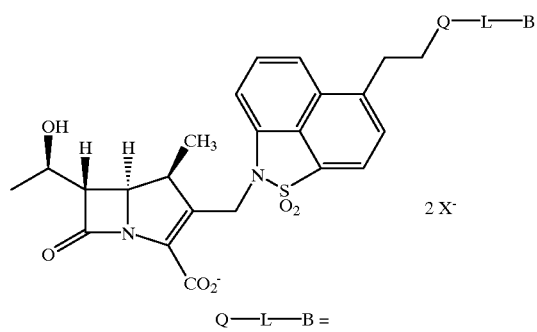
Q—L—B =
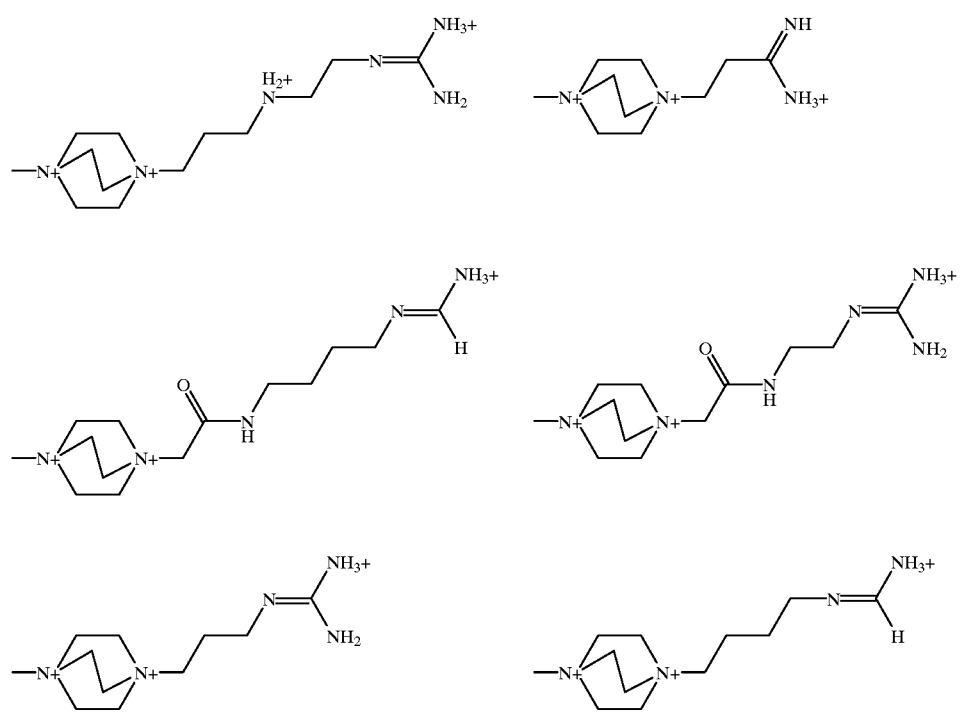

TABLE II
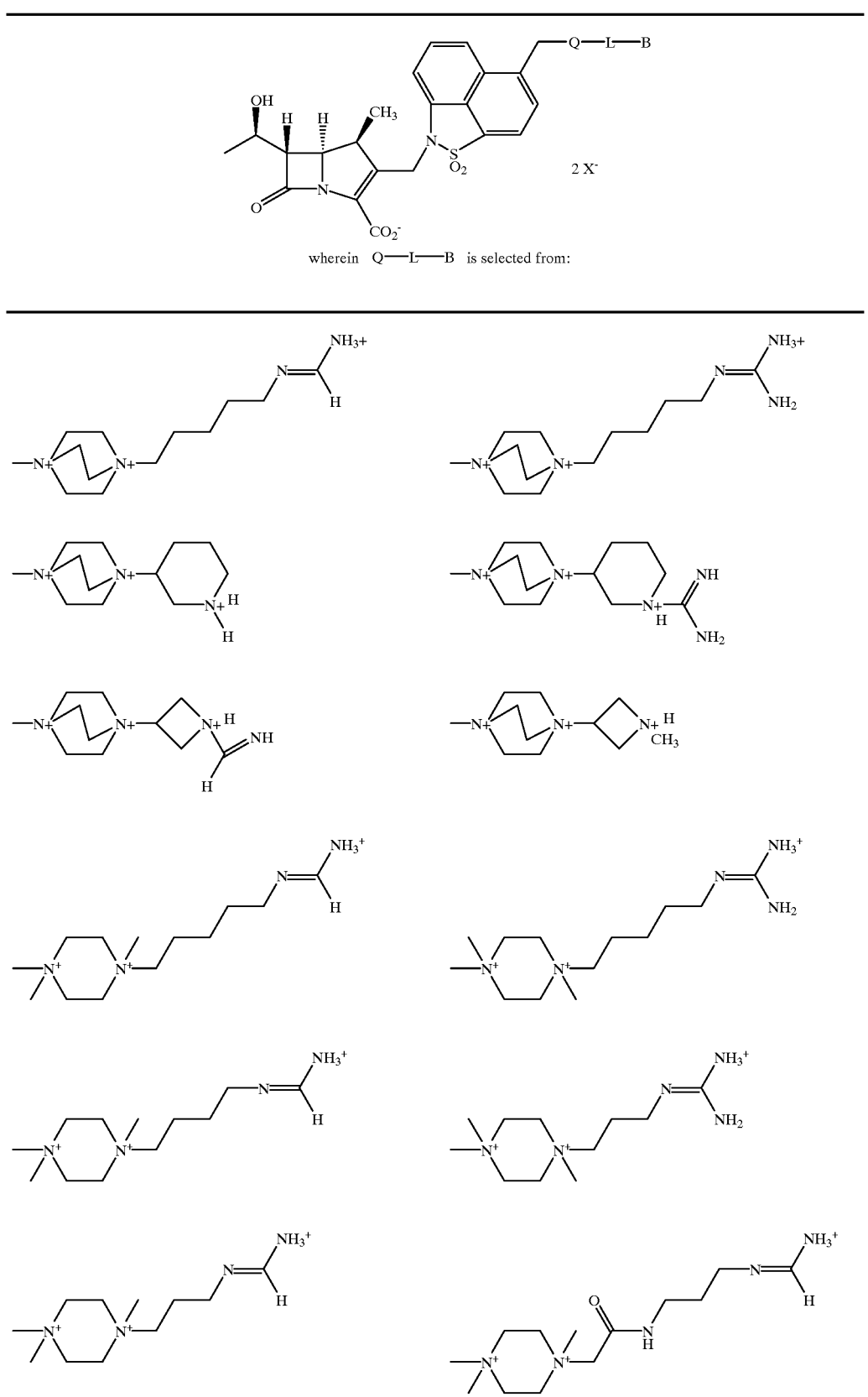
wherein Q—L—B is selected from:

TABLE II-continued
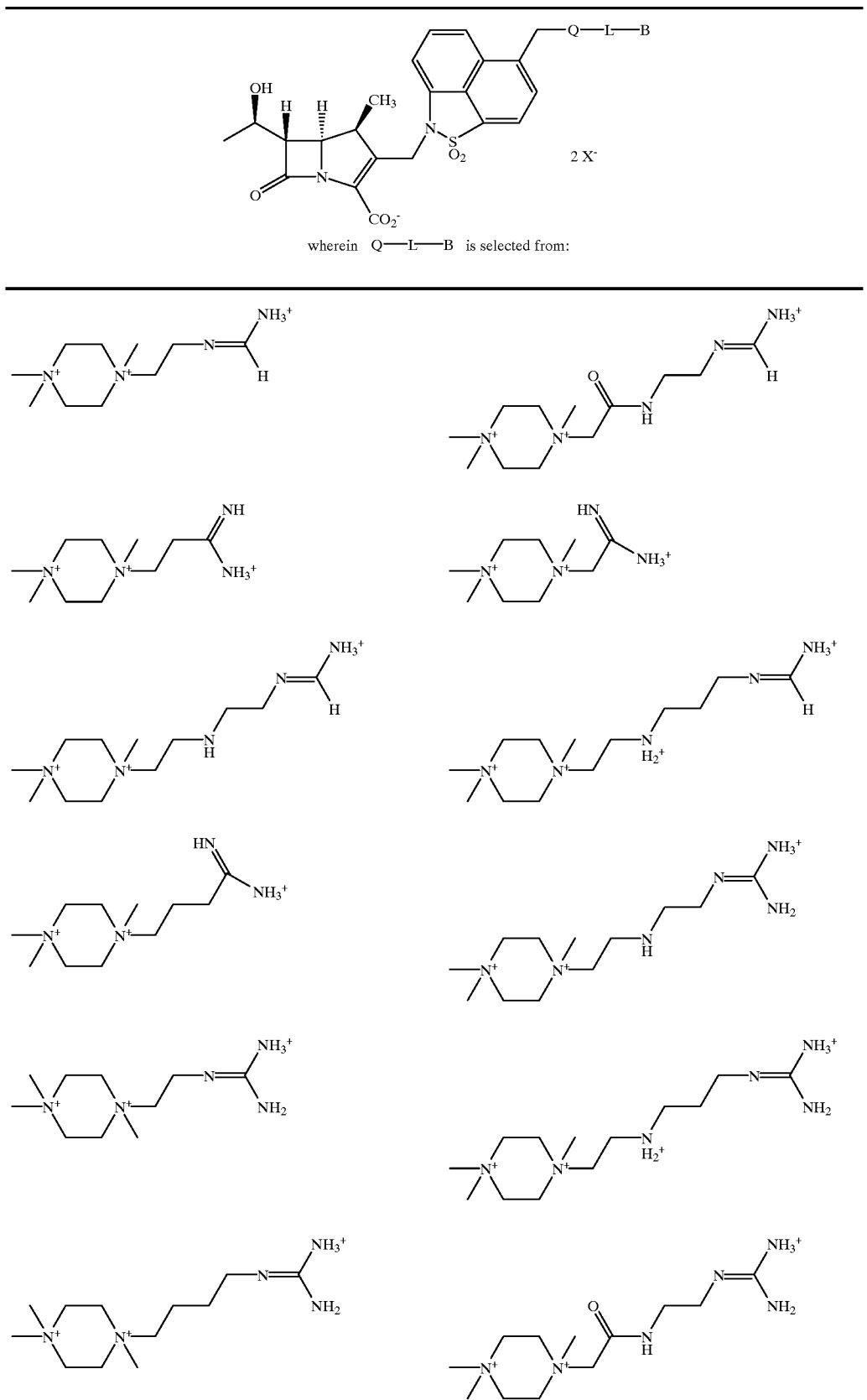
wherein Q—L—B is selected from:

TABLE II-continued
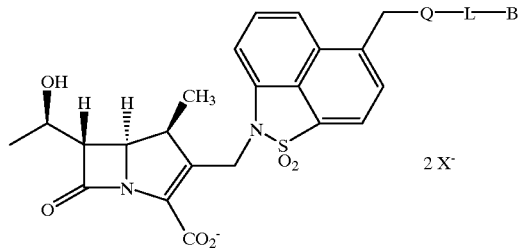
wherein Q—L—B is selected from:
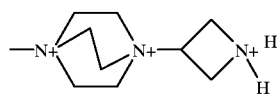
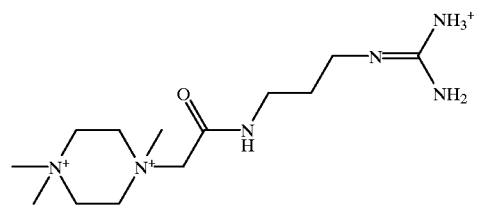
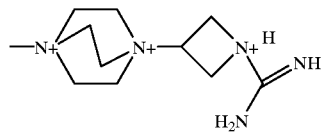
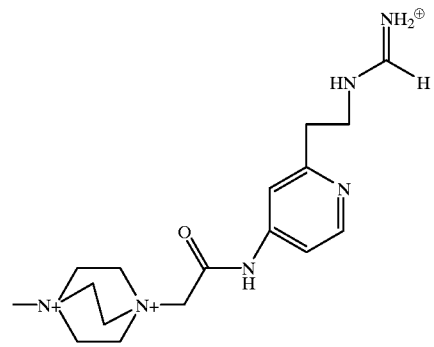
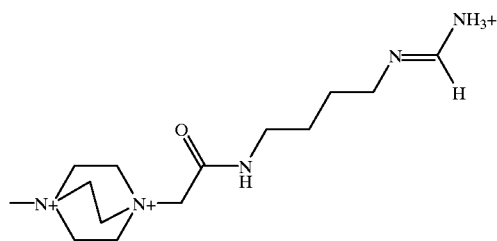
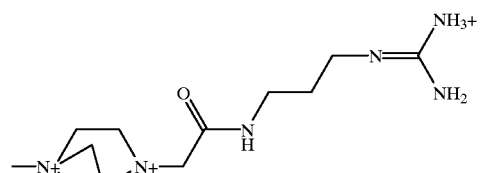
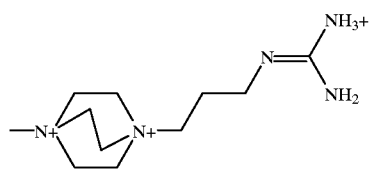
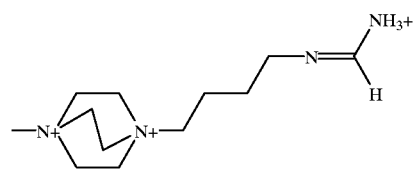

TABLE III
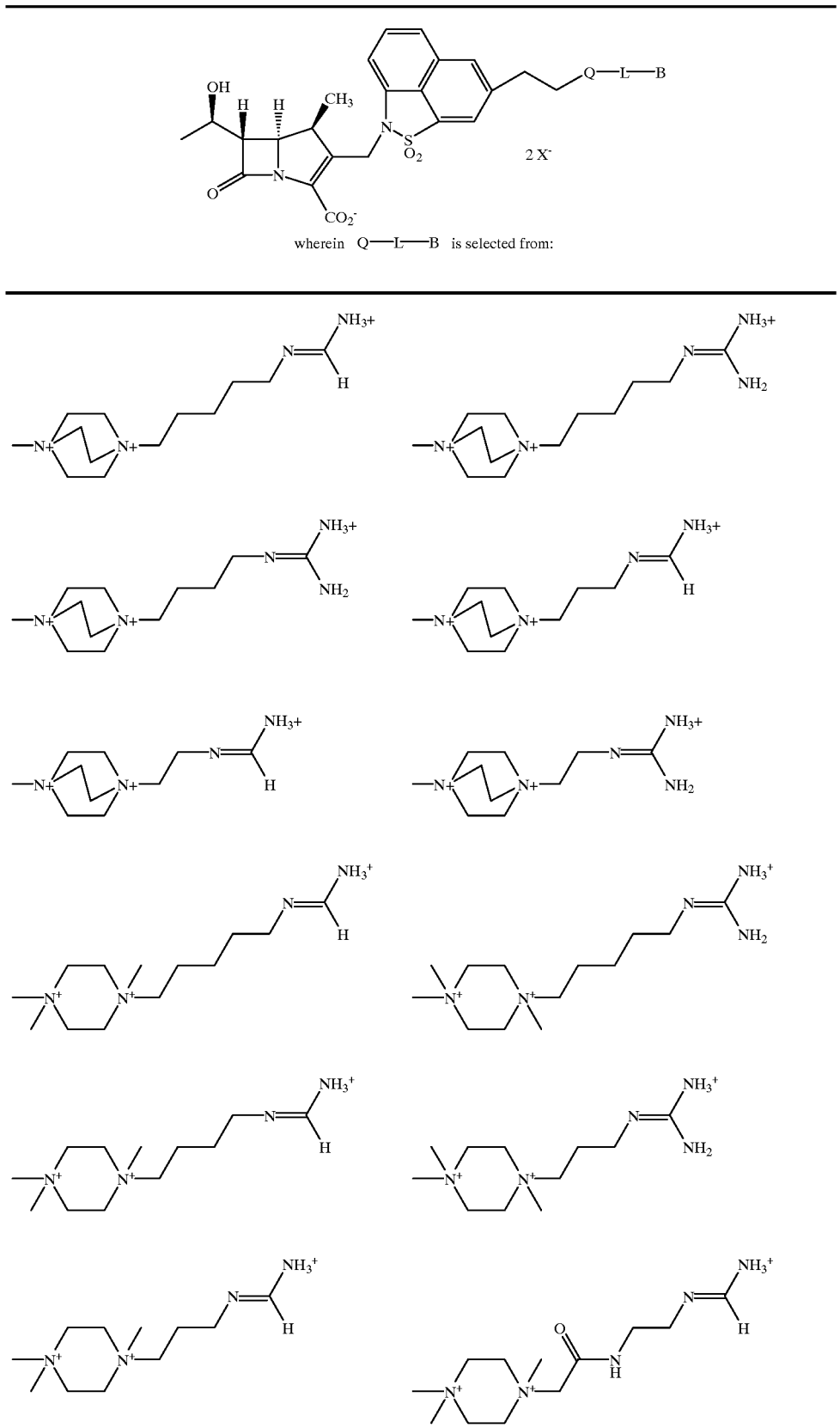
wherein Q—L—B is selected from:

TABLE III-continued
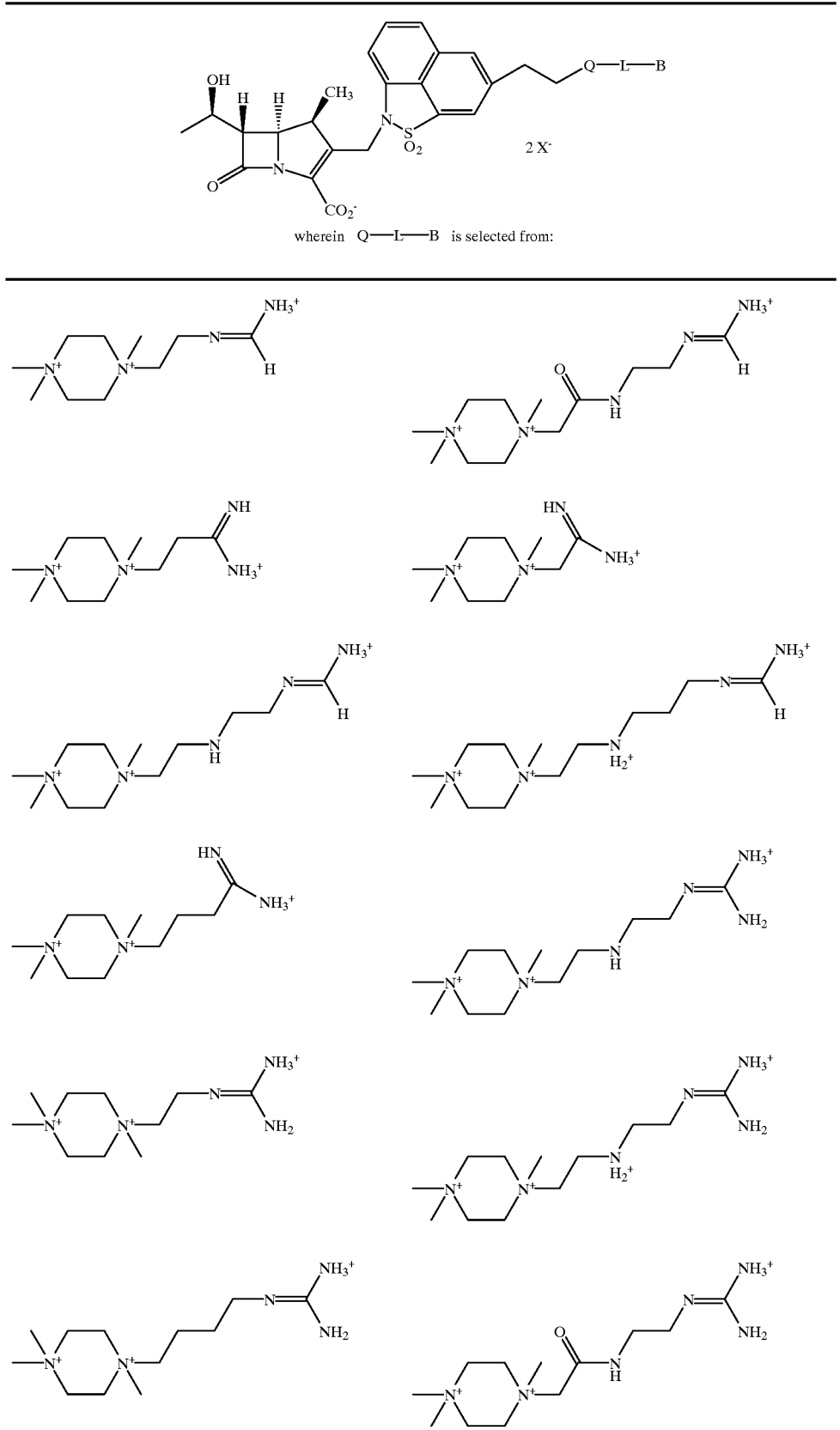

TABLE III-continued

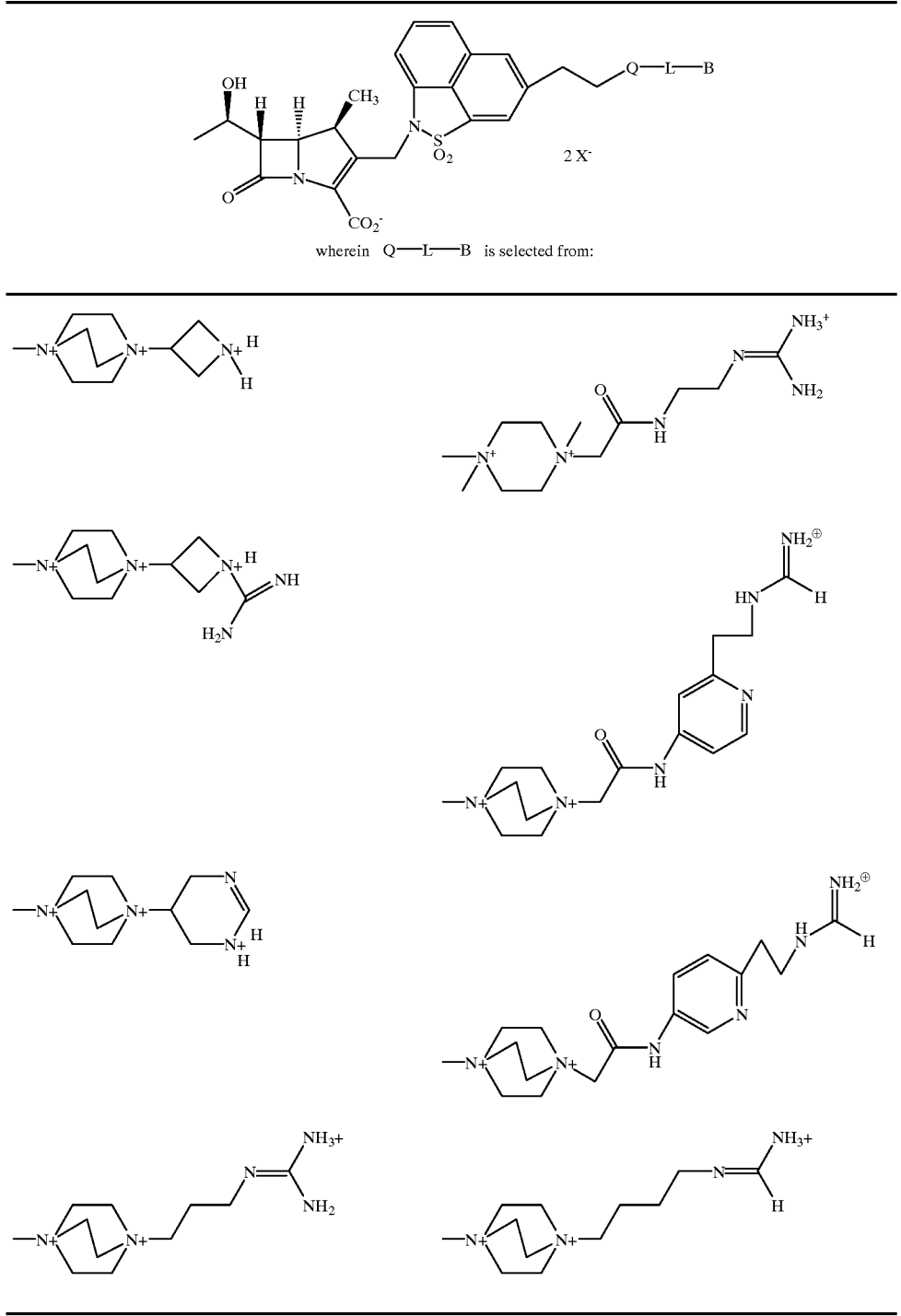

wherein X⁻ represents a counterion.

9. A A pharmaceutical composition which is comprised of a compound in accordance with claim 1 in combination with a carrier.

10. A method of treating or preventing a bacterial infection in a mammalian patient in need thereof, comprising administering to said patient an antibacterially effective amount of a compound as described in claim 1.

UNITED STATES PATENT AND TRADEMARK OFFICE
CERTIFICATE OF CORRECTION

PATENT NO.   : 6,140,318
DATED        : October 31, 2000
INVENTOR(S)  : Lovji D. Cama, Robert R. Wilkening, Ronald W. Ratcliffe, Kenneth J. Wildonger and Wanying Sun It is certified that error appears in the above-identified patent and that said Letters Patent is hereby corrected as shown below:

Column 122, claim 1,
Line 23, should read as follows, -- oms selected from O, S and N; and -- .

Column 124, claim 7,
Line 14, should read as follows, -- wherein c and d are independently 0-4, such that c+d equals -- .

Column 127, claim 8,
Delete the last two structures;

Column 128, claim 8,
Delete the last structure;

Columns 129, claim 8,
Delete all structures;

Columns 131-132, claim 8,
Delete the first five structures;

Column 134, claim 8,
Structure 5 should be as follows:

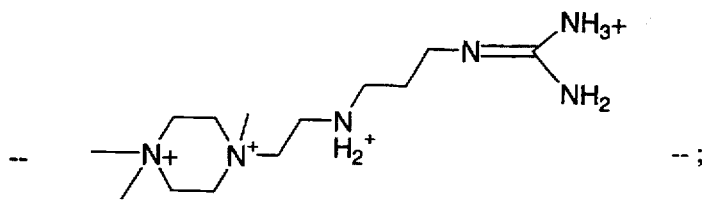

UNITED STATES PATENT AND TRADEMARK OFFICE
CERTIFICATE OF CORRECTION

PATENT NO.    : 6,140,318
DATED         : October 31, 2000
INVENTOR(S)   : Lovji D. Cama, Robert R. Wilkening, Ronald W. Ratcliffe, Kenneth J. Wildonger and Wanying Sun It is certified that error appears in the above-identified patent and that said Letters Patent is hereby corrected as shown below:

Column 135, claim 8,
Delete all structures;

Column 136, claim 8,
Delete structures 2, 3 and 4;

Columns 137-138, claim 8,
Remove the first three structures;

Column 138, claim 8,
The last structure should be as follows:

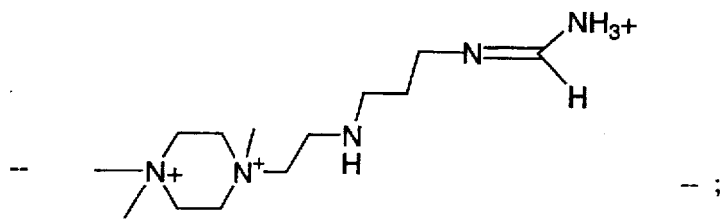

Column 140, claim 8,
The first structures should be as follows:

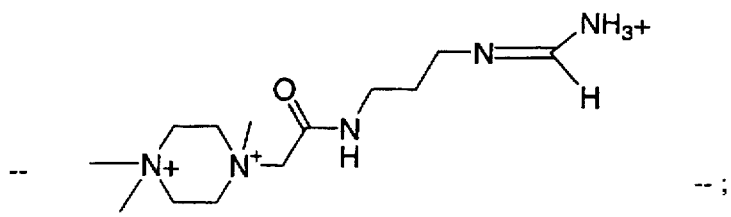

UNITED STATES PATENT AND TRADEMARK OFFICE
CERTIFICATE OF CORRECTION

PATENT NO. : 6,140,318  
DATED : October 31, 2000  
INVENTOR(S) : Lovji D. Cama, Robert R. Wilkening, Ronald W. Ratcliffe, Kenneth J. Wildonger and Wanying Sun It is certified that error appears in the above-identified patent and that said Letters Patent is hereby corrected as shown below:

Column 140, claim 8,
The fifth structure should be as follows:

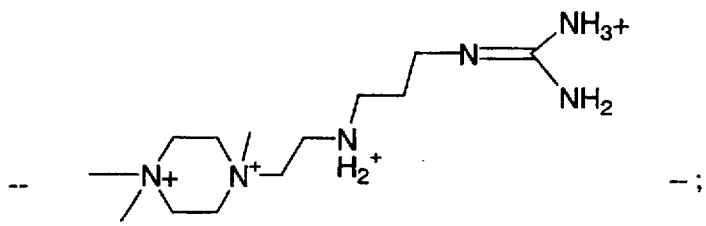

Column 141, claim 8,
Delete structures 1, 2 and 3;

Column 142, claim 8,
The first structure should be as follows:

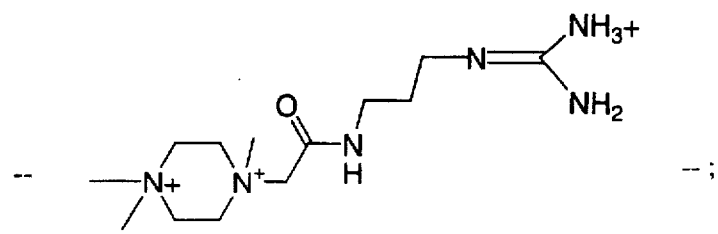

UNITED STATES PATENT AND TRADEMARK OFFICE
CERTIFICATE OF CORRECTION

PATENT NO. : 6,140,318
DATED : October 31, 2000
INVENTOR(S) : Lovji D. Cama, Robert R. Wilkening, Ronald W. Ratcliffe, Kenneth J. Wildonger and Wanying Sun It is certified that error appears in the above-identified patent and that said Letters Patent is hereby corrected as shown below:

Column 142, claim 8,
Delete structures 2 and 3;

Column 141, claim 9,
Line 60, should read as follows,
-- 9. A pharmaceutical composition which is comprised of -- .

Signed and Sealed this

Twenty-seventh Day of November, 2001

*Attest:*

NICHOLAS P. GODICI
*Attesting Officer*   Acting Director of the United States Patent and Trademark Office